US007468185B2

(12) United States Patent
Hardham et al.

(10) Patent No.: US 7,468,185 B2
(45) Date of Patent: *Dec. 23, 2008

(54) VACCINE FOR PERIODONTAL DISEASE

(75) Inventors: John Morgan Hardham, Gales Ferry, CT (US); Kendall Wayne King, Waterford, CT (US); Rajendra Krishnan, Portage, MI (US); Kimberly Jean Dreier, Oakdale, CT (US); David Ross McGavin, Portage, MI (US)

(73) Assignee: Pfizer Inc., New York, NY (US)

(*) Notice: Subject to any disclaimer, the term of this patent is extended or adjusted under 35 U.S.C. 154(b) by 36 days.

This patent is subject to a terminal disclaimer.

(21) Appl. No.: 10/323,069

(22) Filed: Dec. 18, 2002

(65) Prior Publication Data

US 2003/0228328 A1 Dec. 11, 2003

Related U.S. Application Data

(60) Provisional application No. 60/342,999, filed on Dec. 21, 2001.

(51) Int. Cl.
*A61K 39/02* (2006.01)
*C07H 21/04* (2006.01)
*C12P 21/02* (2006.01)
*C12N 1/12* (2006.01)
*C07K 14/195* (2006.01)

(52) U.S. Cl. ............ 424/190.1; 424/50; 435/69.1; 435/252.3; 435/320.1; 530/350; 536/23.7

(58) Field of Classification Search ............. 424/234.1, 424/190.1, 50; 435/69.1, 252.3, 320.1; 535/23.7; 530/350; 536/23.7
See application file for complete search history.

(56) References Cited

U.S. PATENT DOCUMENTS

| 4,661,350 | A | 4/1987 | Tsurumizu et al. |
| 5,536,497 | A | 7/1996 | Evans et al. |
| 6,160,087 | A | 12/2000 | Ogawa |
| 6,444,799 | B1 * | 9/2002 | Ross .................. 536/23.1 |

FOREIGN PATENT DOCUMENTS

| JP | 61-140527 | 6/1986 |
| WO | WO 95/09181 | 4/1995 |
| WO | WO 95/10612 | 4/1995 |
| WO | WO 01/83530 A1 | 11/2001 |

OTHER PUBLICATIONS

Fournier et al 2001, International Journal of Systemic and Evolutionary Microbiology, vol. 51: 1179-1189.*
Bailey et al 1995, International Journal of Systemic Bacteriology, vol. 45: 246-249.*
Evans et al Infect Immun. 1992,60(7): 2926-2935.*
Rumpf RW, et al , Clin Microbiol. Aug. 1999;37(8):2723-5.*
J.Clin Microbiol. Mar. 2002; 40(3): 1044-1047.*
Kesavalu L, Infect Immun. Apr. 1992;60(4):1455-64.*
Dickinson D.P. et al., "Molecular Cloning and Sequencing of the Gene Encoding the Fimbrial Subunit Protein of *Bacteroides gingivalis*", *Journal of Bacteriology* 170(4):1658-1665 (1988).
Evans R.T. et al., "Immunization with *Porphyromonas (Bacteroides) gingivalis* Fimbriae Protects against Periodontal Destruction", *Infection and Immunity* 60(7):2926-2935 (1992).
Collins M.D. et al., "Phylogenetic Analysis of Members of the Genus *Porphyromonas* and Description of *Porphyromonas cangingivalis* sp. nov. and *Porphyromonas cansulci* sp. nov.", *International Journal of Systematic Bacteriology* 44(4):674-679 (1994).
Harvey C.E. et al., "Subgingival Bacteria-Comparison of Culture Results in Dogs and Cats With Gingivitis", *J. Vet. Dent.* 12(4):147-150 (1995).
Allaker R.P. et al., "Prevalence of *Porphyromonas* and *Prevotella* species in the dental plaque of dogs" *The Veterinary Record* 140 (6):147-148 (1997).
Norris J.M. et al., "Associations amongst three feline *Porphyromonas* species from the gingival margin of cats during periodontal health and disease", *Veterinary Microbiology* 65 :195-207 (1999).
Sharma A. et al., "Oral Immunization with Recombinant *Streptococcus gordonii* Expressing *Porphyromonas gingivalis* FimA Domains", *Infection and Immunity* 69 (5):2928-2934 (2001).
Ross B.C. et al., "Identification of vaccine candidate antigens from a genomic analysis of *Porphyromonas gingivalis*", *Vaccine* 19:4135-4142 (2001).
Carl R. Woese, "Bacterial Evolution," Microbiological Reviews, Jun. 1987, vol. 51, No. 2, pp. 221-271.

* cited by examiner

*Primary Examiner*—Robert B Mondesi
*Assistant Examiner*—Padma V Baskar
(74) *Attorney, Agent, or Firm*—Lorraine B. Ling; Bruce S. Weintraub; E. Victor Donahue

(57) ABSTRACT

The present invention relates to novel bacterial isolates identified by their 16S rRNA DNA, that cause periodontal disease in companion animals, polynucleotide sequences contained therein, polypeptides encoded by such polynucleotide sequences and vaccines comprising such bacteria, polynucleotides, or polypeptides. Also provided are methods for treating and preventing periodontal disease and kits for detecting and treating periodontal disease kits for detecting and preventing periodontal disease.

4 Claims, 14 Drawing Sheets

VACCINE FOR PERIODONTAL DISEASE

CROSS-REFERENCE TO RELATED APPLICATION

This application claims the benefit of U.S. Provisional Patent Application No. 60/342,999 filed Dec. 21, 2001, the contents of which are hereby incorporated by reference in its entirety.

FIELD OF THE INVENTION

The present invention relates to novel bacterial isolates identified by their 16S rRNA DNA, that cause periodontal disease in companion animals, polynucleotide sequences contained therein, polypeptides encoded by such polynucleotide sequences and vaccines comprising such bacterial isolates that have been inactivated or attenuated, polynucleotides or polypeptides. Also provided are methods for treating and preventing periodontal disease and kits for detecting, treating, and preventing periodontal disease.

BACKGROUND ART

The vast majority of experimental data concerning periodontal diseases is based on studies of humans or bacteria isolated from humans. Relatively little is known with respect to periodontal disease in non-human animals, such as companion animals, and in particular, dogs and cats.

Periodontal disease comprises a group of infections involving supporting tissues of the teeth. These range in severity from mild and reversible inflammation of the gingiva (gum) to chronic destruction of periodontal tissues (gingiva, periodontal ligament, and alveolar bone) with eventual exfoliation of teeth.

From a microbiological standpoint, several features of this disease are of interest. The bacterial etiology is complex, with a variety of organisms responsible for the initiation and progression of disease in humans. Many, if not all, of these organisms may also be present in periodontally healthy individuals and can exist in commensal harmony with the host. Thus, disease episodes may ensue from a shift in the ecological balance between bacterial and host factors, as a result of, for example, alteration in the absolute or relative numbers of certain organisms, changes in pathogenic potential, or modulation of particular host factors. The local environment imposes a variety of unique constraints upon the constituent microbiota of the supragingival tooth surface and the subgingival crevice (the channel between the tooth root and the gingiva that deepens into a periodontal pocket as disease progresses).

Both the calcified hard tissues of the tooth and the epithelial cells of the gingival are available for colonization. These tissues are exposed to host salivary secretions and gingival crevicular fluid (a serum exudate), both of which contain molecules that interact directly with bacteria and alter prevailing environmental conditions. In addition, it is known that in humans, successful colonizers of the teeth and subgingival area must coexist with many (over 600) other species of bacteria that inhabit these regions. Study of the pathogenesis of periodontal diseases in humans is thus complicated by the ecological intricacy of the microenvironment.

The classification of the various manifestations of periodontal disease in humans is continually changing, and it will suffice to mention that diseases range in severity, rate of progression, and number of teeth affected and that different age groups can be susceptible following the eruption of primary teeth. The nature of the pathogenic agents varies among these disease entities, as well as among human patients and even between different disease sites within a patient. In general, however, severe forms of the disease are associated with a number of gram-negative anaerobic bacteria. Of this group, in humans, most evidence points to a pathogenic role for *Porphyromonas* (formerly *Bacteroides*) *gingivalis*. The presence of this organism, acting either alone or as a mixed infection with other bacteria, and possibly in concert with the absence of beneficial species and certain immunological responses in the host, appears to be essential for disease activity.

Colonization of the oral cavity requires that the bacteria first enter the mouth and then localize at and attach to the available surfaces. Host factors which function to prevent bacterial colonization include the mechanical shearing forces of tongue movement along with saliva and gingival crevicular fluid flow. Successful oral colonizers therefore possess a variety of attributes to overcome host protective mechanisms. The sessile plaque biofilm that subsequently accumulates on the hard and soft tissues of the mouth is a dynamic system composed of diverse microbial species. In humans, *P. gingivalis* is usually among the late or secondary colonizers of the oral cavity, requiring antecedent organisms to create the necessary environmental conditions.

Initial entry of *P. gingivalis* into the human oral cavity is thought to occur by transmission from infected individuals. Other vectors would therefore also appear to be operational. These studies indicate that individuals are colonized by a single (or at least a predominant) genotype, regardless of site of colonization or clinical status. Strains of many different clonal origins, in contrast, are present in different individuals. This supports the concept that *P. gingivalis* is essentially an opportunistic pathogen, with virulence not being restricted to a particular clonal type.

The human oral cavity provides a variety of surfaces to which *P. gingivalis* can adhere. There are the mineralized hard tissues of the teeth, along with mucosal surfaces including those of the gingiva, cheek, and tongue.

While a great deal is known about periodontal disease in humans, as described above, very little is known about the same disease in companion animals. Fournier, D. et al., "*Porphyromonas gulae* sp. nov., an Anaerobic, Gram-negative, Coccibacillus from the Gingival Sulcus of Various Animal Hosts", International Journal of a Systematic and Evolutionary Microbiology (2001), 51, 1179-1189 describe several strains isolated from various animal hosts, including a strain, *P. gulae* spp. nov., designated ATCC 57100. The authors hypothesize that strains for the animal biotype of *P. gingivalis* represent a *Porphyromonas* species that is distinct from *P. gingivalis*. There is no mention of a vaccine useful in treating periodontal disease in companion animals. Hirasawa and Takada, in "*Porphyromonas gingivicanis* sp. nov. and *Porphyromonas crevioricanis* sp. nov., Isolated from Beagles", International Journal of Systemic Bacteriology, pp. 637-640, (1994), describe two bacterial species isolated from gingival crevicular fluids of beagles. These species are described in U.S. Pat. Nos. 5,710,039 and 5,563,063. Nowhere do the authors suggest the use of these species in a vaccine to treat periodontal disease. International Application PCT/AU98/01023, having publication number WO 99/29870, described various *P. gingivalis* polypeptides and nucleotides. However, no evidence of vaccines effective in preventing periodontal disease in companion animals is provided. Even though there is a great amount of information known about the human disease, little has been accomplished by way of preventing or treating the disease, even in humans.

There remains a need for a safe and effective vaccine for treating and preventing periodontal disease in companion animals.

SUMMARY OF THE INVENTION

The present invention provides an isolated pigmented anaerobic bacteria having a 16S rRNA DNA sequence comprising a nucleotide sequence selected from the group consisting of SEQ ID NOS: 86 to 94, provided that the bacteria is not a strain of *Porphyromonas gingivalis* designated as dog 20B.

In one embodiment, the bacteria is selected from the group consisting of *Porphyromonas gulae* B43, *P. cansulci* B46, *P. circumdentaria* B52, *P. gulae* B69, *P. circumdentaria* B97, *P. cangingivalis* B98, *P. salivosa* B104, *P. denticanis* B106 and *P. endodontalis* B114, provided that the bacteria is not a strain of *Porphyromonas gingivalis* designated as dog 20B.

In another embodiment, the present invention provides an isolated pigmented anaerobic bacteria which causes, either directly or in combination with other pathogenic agents, periodontal disease in companion animals, wherein the bacteria can be used to prepare a vaccine for treating or preventing periodontal disease in companion animals, wherein the vaccine comprises an immunologically effective amount of at least one bacteria which has been inactivated or attenuated, provided that the bacteria is not a strain of *P. gulae* sp. nov. designated ATCC 51700. Preferably, the bacteria has a 16S rRNA DNA sequence at least about 95% homologous to any of the sequences depicted in SEQ ID NOS: 86 to 94. More preferably, the bacteria has a 16S rRNA DNA sequence comprising a nucleotide sequence selected from the group consisting of SEQ ID NOS: 86 to 94.

In another embodiment, the present invention provides an isolated pigmented anaerobic bacteria which causes, either directly or in combination with other pathogenic agents, periodontal disease in companion animals, wherein the bacteria can be used to prepare a vaccine for treating or preventing periodontal disease in companion animals, wherein the vaccine comprises an isolated polypeptide immunologically effective as a vaccine for preventing or treating periodontal disease in companion animals, wherein the polypeptide is encoded by a polynucleotide molecule isolated from the bacteria provided that the bacteria is not a strain of *P. gulae* sp. nov. designated ATCC 51700. Preferably, the bacteria has a 16S rRNA DNA sequence at least about 95% homologous to any of the sequences depicted in SEQ ID NOS: 86 to 94. More preferably, the bacteria has a 16S rRNA DNA sequence comprising a nucleotide sequence selected from the group consisting of SEQ ID NOS: 86 to 94.

In a further embodiment, the present invention provides an isolated pigmented anaerobic bacteria which causes, either directly or in combination with other pathogenic agents, periodontal disease in companion animals, wherein the bacteria can be used to produce a vaccine for treating or preventing periodontal disease in companion animals, wherein the vaccine comprises an isolated polynucleotide molecule which encodes a polypeptide immunologically effective as a vaccine for preventing or treating periodontal disease in companion animals, wherein the polynucleotide molecule is isolated from the bacteria, provided that the bacteria is not a strain of *P. gulae* sp. nov. designated ATCC 51700. Preferably, the bacteria has a 16S rRNA DNA sequence at least about 95% homologous to any of the sequences depicted in SEQ ID NOS: 86 to 94. More preferably, the bacteria has a 16S rRNA DNA sequence comprising a nucleotide sequence selected from the group consisting of SEQ ID NOS: 86 to 94.

The companion animal is preferably a dog or a cat.

In another aspect, the present invention provides isolated polynucleotide molecule comprising a nucleotide sequence isolated from a bacteria selected from the group consisting of a bacterium having the identifying characteristics of *Porphyromonas gulae* B43, *P. cansulci* B46, *P. circumdentaria* B52, *P. gulae* B69, *P. circumdentaria* B97, *P. cangingivalis* B98, *P. salivosa* B104, *P. denticanis* B106 and *P. endodontalis* B114 provided that the bacteria is not a strain of *P. gulae* sp. nov. designated ATCC 51700.

In one embodiment, the isolated polynucleotide molecule is isolated from a bacterium, wherein the bacterium is selected from the group consisting of *Porphyromonas gulae* B43, *P. cansulci* B46, *P. circumdentaria* B52, *P. gulae* B69, *P. circumdentaria* B97, *P. cangingivalis* B98, *P. salivosa* B104, *P. denticanis* B106 and *P. endodontalis* B114.

In another embodiment, the isolated polynucleotide according to claim 15 or 16 wherein the polynucleotide encodes for a polypeptide.

In yet another embodiment, the isolated polynucleotide according to claim 15 or 16 wherein, the polynucleotide encodes ribosomal RNA or transfer RNA.

In yet a further embodiment, the present invention provides an isolated polynucleotide molecule comprising any of the nucleotide sequences selected from the group consisting of SEQ ID NOS: 86 to 94 and homologues having at least 95% homology thereto, provided that the nucleotide sequence is not the 16S rRNA DNA from bacteria *P. gulae* sp. nov. designated ATCC 51700.

Preferably, the isolated polynucleotide molecule comprising any of the nucleotide sequences selected from the group consisting of SEQ ID NOS: 95 to 102 and 111-119, (fimA or oprF, respectively), which sequence encodes a polypeptide immunologically effective as a vaccine for preventing or treating periodontal disease in companion animals, or complements thereto.

Also preferred is the isolated polynucleotide molecule comprises any of the nucleotide sequences depicted in SEQ ID NOS: 95 to 102 and 111-119, homologues having at least 95% homology thereto, which sequence encodes a polypeptide immunologically effective as a vaccine for preventing or treating periodontal disease in companion animals, or complements thereto.

In a further embodiment, the isolated polynucleotide molecule comprises any of the nucleotide sequences depicted in SEQ ID NOS: 95 to 102 and 111-119 or fragments or variants thereof, which sequence encodes a polypeptide immunologically effective as a vaccine for preventing or treating periodontal disease in companion animals, or complements thereto.

In yet a further embodiment, the isolated polynucleotide molecule comprises a nucleotide sequence which hybridizes under conditions of high stringency to any of the sequences depicted in SEQ ID NOS: 95 to 102 and 111-119, or complements thereto. Preferably, the isolated polynucleotide sequence, wherein said sequence comprises the sequence of fimA, selected from any of the sequences depicted in SEQ ID NOS: 95 to 102, a fragment or variant thereof, which fragment or variant has at least about 95%, 98% or 99% sequence identity thereto. Also preferred is the isolated polynucleotide molecule, wherein said sequence comprises the sequence of oprF, selected from, selected from any of the sequences depicted in SEQ ID NOS, 111 to 119, a fragment or variant thereof, which fragment or variant has at least about 95%, 98% or 99% sequence identity thereto.

Preferably, the fragment or variant of the polynucleotide molecule according to the present invention is at least about 98% homologous thereto.

In another embodiment, the present invention provides an isolated polynucleotide molecule, comprising a nucleotide sequence that hybridizes under conditions of high stringency to fimA, selected from any of the sequences depicted in SEQ ID NOS, 95 to 102, or the complement thereof.

In yet another embodiment, the present invention provides isolated polynucleotide molecule, comprising a nucleotide sequence that hybridizes under conditions of high stringency to oprF, selected from any of the sequences depicted in SEQ ID NOS, 111 to 119, or the complement thereof.

The present invention also provides an isolated polynucleotide molecule comprising a nucleotide sequence of about 30 nucleotides, which hybridizes under highly stringent conditions to a DNA molecule having a nucleotide sequence encoding a polypeptide having a sequence of at least about 10 contiguous amino acids of any of the polypeptides encoded by any of the nucleotide sequences of SEQ ID NOS: 95 to 102 and 109 to 119, or its complement. Preferably, the isolated polynucleotide molecule comprises at least about 90 nucleotides, which hybridizes under conditions of high stringency to a DNA molecule having a nucleotide sequence encoding a polypeptide having a sequence of at least about 30 contiguous amino acids of any of the polypeptides encoded by any of the nucleotide sequences of SEQ ID NOS: 95 to 102 and 111 to 119, or its complement.

In another aspect, the present invention provides the isolated polynucleotide according to the present invention operably linked to a heterologous promoter. The isolated polynucleotide can further comprise an origin of replication active in a prokaryotic or eukaryotic cell.

In another aspect, the present invention provides a recombinant expression vector comprising a polynucleotide selected from the group consisting of any of the nucleotide sequences SEQ ID NOS: 95 to 102 and 111 to 119, fragments or variants thereof, operably linked to a promoter sequence.

In yet another aspect, the present invention provides a plasmid comprising a polynucleotide selected from the group consisting of any of the nucleotide sequences SEQ ID NOS: 95 to 102 and 111 to 119, fragments or variants thereof, operably linked to a promoter sequence.

In a further aspect, the present invention provides a host cell comprising the isolated polynucleotide sequence, vector or plasmid according to the present invention.

Preferably, the host cell is E. coli BL21 and said polynucleotide further comprises the expression vector pBAD/HisA or a λ expression plasmid.

In a further aspect, the present invention provides, a method for the production of recombinant FimA or, OprF, selected from any of the sequences depicted in SEQ ID NOS: 103 to 110 or 120 to 128, or fragments or variants thereof, said method comprising (1) growing the cells of claim 36 under conditions in which a polypeptide comprising FimA, OprF, or fragments or variants thereof is expressed, and (2) recovering said polypeptide. The polypeptide can be recovered in soluble or insoluble form.

In another aspect, the isolated polypeptide of the present invention is immunologically effective as a vaccine for preventing or treating periodontal disease in companion animals and comprises an amino acid sequence depicted in SEQ ID NOS: 103 to 110 and 120 to 128.

In one embodiment, the isolated polypeptide immunologically effective as a vaccine for preventing or treating periodontal disease in companion animals comprises an amino acid sequence depicted in SEQ ID NOS: 103 to 110 and 120 to 128 and homologues having at least 95%, 98%, or 99% sequence identity thereto.

In another embodiment, the isolated polypeptide immunologically effective as a vaccine for preventing or treating periodontal disease in companion animals comprises an amino acid sequence depicted in SEQ ID NOS: 103 to 110 and 120 to 128, or fragments or variants thereof.

In yet another embodiment, the isolated polypeptide immunologically effective as a vaccine for preventing or treating periodontal disease in companion animals having an amino acid sequence encoded by a DNA molecule comprises a nucleotide sequence which hybridizes under conditions of high stringency to any of the sequences depicted in SEQ ID NOS: 95 to 102 and 111 to 119.

In yet a further embodiment, the isolated polypeptide immunologically effective as a vaccine for preventing or treating periodontal disease in companion animals, which polypeptide comprises at least about 10 contiguous amino acids comprises a fragment of any of the polypeptide sequences of SEQ ID NOS: 103 to 110 and 120 to 128, which polypeptide is immunologically effective, either alone or linked to a carrier, as a vaccine for preventing or treating periodontal disease in companion animals. Preferably, the isolated polypeptide comprises at least about 25 amino acids.

Preferably, the isolated polypeptide, for preventing or treating periodontal disease in companion animals, encoded by a DNA molecule comprising a nucleotide sequence which comprises the sequence of fimA (SEQ ID NOS: 95 to 102).

Also preferred, the isolated polypeptide, for preventing or treating periodontal disease in companion animals, encoded for by a DNA molecule comprising a nucleotide sequence which comprises the sequence of oprF (SEQ ID NOS: 111 to 119).

In a preferred embodiment, the isolated polypeptide is a recombinantly expressed polypeptide, which polypeptide is selected from the group consisting of FimA (SEQ ID NOS: 103 to 110) and OprF (SEQ ID NOS: 120 to 128).

In another embodiment, the recombinantly expressed polypeptide is fused to a carrier polypeptide. The fusion polypeptide is preferably essentially a poly-histidine or poly-threonine sequence.

In a further aspect, the present invention provides a vaccine for treating or preventing periodontal disease in companion animals comprising an immunologically effective amount of at least one inactivated pigmented anaerobic bacteria according to the present invention, and a pharmaceutically acceptable carrier.

In another aspect, the present invention provides a vaccine for treating or preventing periodontal disease in companion animals comprising an immunologically effective amount of at least one polynucleotide molecule according to the present invention, and a pharmaceutically acceptable carrier.

In yet another aspect, the present invention provides vaccine for treating or preventing periodontal disease in companion animals comprising an immunologically effective amount of at least one polypeptide according to the present invention, and a pharmaceutically acceptable carrier.

Preferably, the vaccine for treating or preventing periodontal disease in companion animals comprises an immunologically effective amount of FimA and a pharmaceutically acceptable carrier.

Also preferred is a vaccine for treating or preventing periodontal disease in companion animals comprising an immunologically effective amount of OprF and a pharmaceutically acceptable carrier.

The bacteria for use in the vaccines of the present invention may be selected from the group consisting of *Porphyromonas gulae* B43, *P. cansulci* B46, *P. circumdentaria* B52, *P. gulae* B69, *P. circumdentaria* B97, *P. cangingivalis* B98, *P. salivosa* B104, *P. denticanis* B106 and *P. endodontalis* B114.

In still another embodiment, the present invention provides a vaccine composition for treating or preventing periodontal disease in companion animals comprising an immunologically effective amount of at least one inactivated isolated pigmented anaerobic bacteria according to the present invention, a pharmaceutically acceptable carrier, and optionally an adjuvant.

In yet another embodiment, the present invention provides a vaccine composition for treating or preventing periodontal disease in companion animals comprising an immunologically effective amount of at least one polynucleotide molecule according to the present invention, a pharmaceutically acceptable carrier, and optionally, an adjuvant.

In still a further embodiment, the present invention provides a vaccine composition for treating or preventing periodontal disease in companion animals comprising an immunologically effective amount of at least one polypeptide according to the present invention, a pharmaceutically acceptable carrier, and optionally, an adjuvant.

In another aspect the present invention provides a method for treating or preventing periodontal disease in companion animals comprising administering to a companion animal in need thereof, a vaccine composition according to the present invention.

In another aspect the present invention provides a method for diagnosing periodontal disease in companion animals by analyzing a sample for bacteria, polypeptides or polynucleotides of the present invention, wherein the presence of the bacteria, polypeptides, or polynucleotides are indicative of disease. Preferably, the analyzing step includes analyzing the sample using a method selected from the group consisting of PCR, hybridization, and antibody detection.

In yet another aspect, the present invention provides a kit comprising, in at least one container, a composition for treating and preventing periodontal disease in companion animals comprising an effective amount of at least one inactivated isolated pigmented anaerobic bacteria, polypeptide, or polynucleotides of the present invention and a pharmaceutically acceptable carrier; wherein the kit further comprises a set of printed instructions indicating that the kit is useful for treating or preventing periodontal disease in companion animals. The kit may further comprises a means for dispensing said composition.

In still another aspect, the present invention provides a kit comprising in at least one container an isolated DNA molecule comprising a nucleotide sequence of at least about 15 contiguous nucleotides selected from any of SEQ ID NOS: 86 to 94, 95 to 102, and 111 to 119 which hybridizes under highly stringent conditions to the complement of any of the nucleotide sequences depicted in SEQ ID NOS: 86 to 94, 95 to 102, and 111 to 119, and a second isolated DNA molecule comprising in a second container an isolated DNA molecule comprising a nucleotide sequence of at least about 15 contiguous nucleotides selected from the complement of any of the nucleotide sequences depicted in SEQ ID NOS: 86 to 94, 95 to 102, and 111 to 119 which hybridizes under highly stringent conditions to any of the nucleotide sequences depicted in SEQ ID NOS: 86 to 94, 95 to 102, and 111 to 119, wherein the kit further comprises a set of instructions indicating that the kit is useful for the detection of *Porphyromonas* spp. Such a method may be used generally in all mammals, including humans.

In yet another aspect, the present invention provides a kit comprising in at least one container a protein having an amino acid sequence comprising at least 30 contiguous amino acids, which polypeptide is encoded by any of the nucleotide sequences of SEQ ID NOS: 95 to 102 and 111 to 119 and a statement indicating that the kit is useful for the detection of *Porphyromonas* spp. The kit may further comprise a second polypeptide, wherein the second polypeptide is an antibody which is conjugated to an enzyme that catalyzes a colorimetric or The enzyme is preferably selected from the group consisting of alkaline phosphatase and horseradish peroxidase. The kit may further comprise reagents for a colorimetric or chemiluminescent assay.

In a further aspect, the present invention provides a hybridization kit comprising in at least one container an isolated DNA molecule comprising a nucleotide sequence of at least about 15 contiguous nucleotides selected from any of SEQ ID NOS: 86 to 94, 95 to 102, and 111 to 119, or its complement, wherein the hybridization is specific to *Porphyromonas* spp. and wherein the kit further comprises a set of instructions indicating that the kit is useful for the detection of *Porphyromonas* spp. Preferably, the hybridization is performed under highly stringent conditions.

None of the bacteria, polynucleotides, polypeptides, vaccine, vaccine compositions or kits of the present invention comprise any of the bacteria, polynucleotides or peptides described in Fournier, D. et al., "*Porphorymonas gulae* sp. nov., an Anaerobic, Gram-negative, Coccibacillus from the Gingival Sulcus of Various Animal Hosts", International Journal of a Systematic and Evolutionary Microbiology (2001), 51, 1179-1189, including a strain, *P. gulae* spp. nov., designated ATCC 57100, Hirasawa and Takada, "*Porphyromonas gingivicanis* sp. nov. and *Porphyromonas creviorcanis* sp. nov., Isolated from Beagles", International Journal of Systemic Bacteriology, pp. 637-640, (1994), U.S. Pat. No. 5,710,039 or U.S. Pat. No. 5,563,063, or International Application PCT/AU98/01023, having publication number WO 99/29870.

DETAILED DESCRIPTION OF THE INVENTION

Bacterial Isolates

Figure 1:
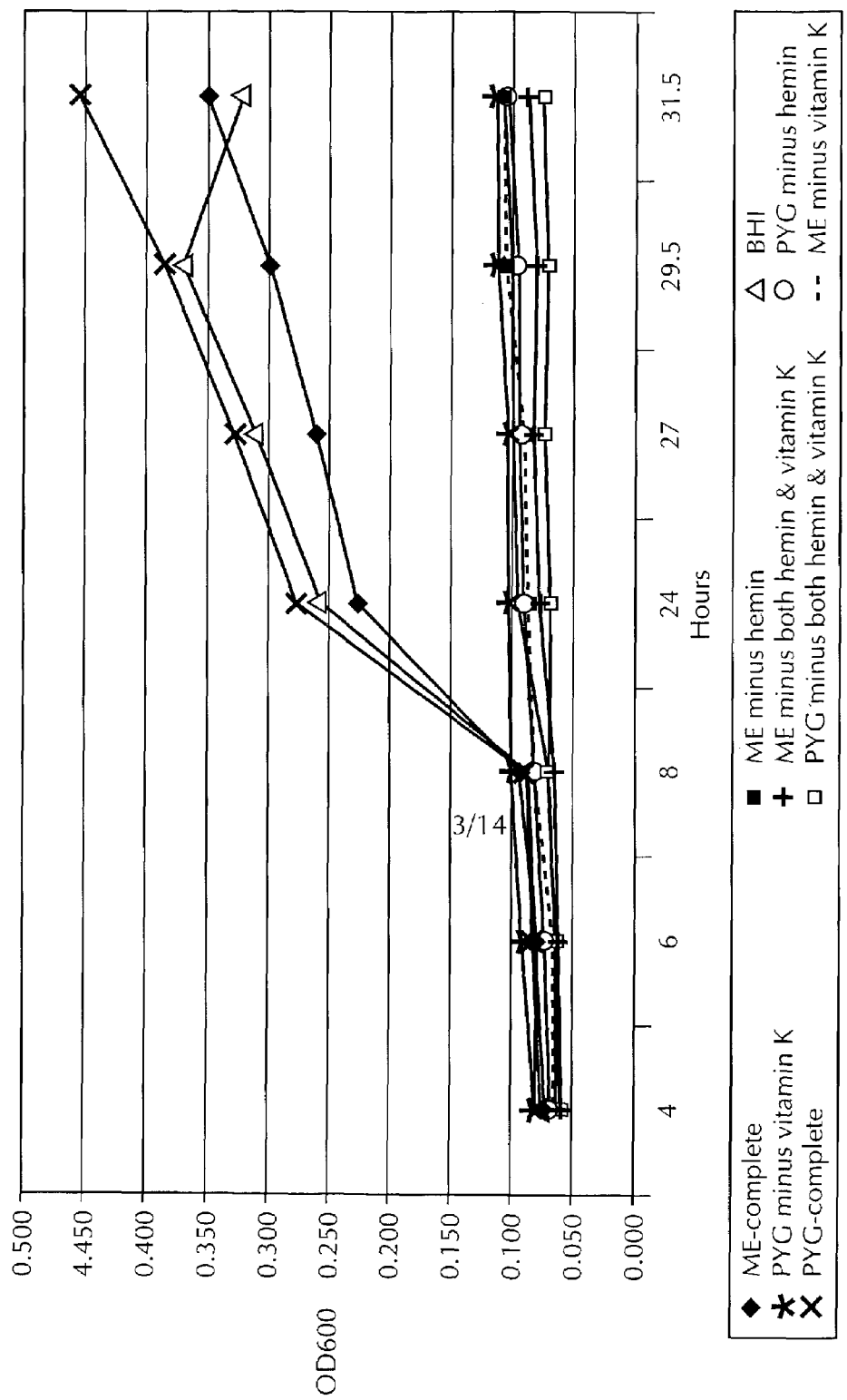
FIG. 1 is a graph showing the results of a growth study identifying an "animal product-free" medium that supports the growth of *Porphyromonas gulae* B43. The following medium were tested: ME-complete, ME-hemin, ME-vitamin K, ME-both hemin and vitamin K, PYG-complete, PYG-hemin, PYG-vitamin K, PYG-both hemin and vitamin K, and BHI.

The present invention provides isolated anaerobic bacteria, identified by their 16S rRNA DNA sequences, which cause periodontal disease and various other diseases and clinical manifestations in companion animals. More specifically, the bacteria are selected from the genus *Porphyromonas*.

Preferably, the isolated bacteria of the present invention include *P. gulae* B43, *P. cansulci* B46, *P. circumdentaria* B52, *P. gulae* B69, *P. circumdentaria* B97, *P. cangingivalis* B98, *P. salivosa* B104, *P. denticanis* B106, and *P. endodontalis* B114, although other species or strains are encompassed by the invention. In a preferred embodiment, the isolated bacteria of the present invention can be identified by their 16S rRNA DNA sequences shown in SEQ ID Nos. 86 to 94.

The diseases caused by infection with the bacteria of the present invention include, but are not limited to, companion animal periodontal disease, companion animal oral malodor (halitosis), bovine foot rot, canine coronary heart disease and canine systemic infections. Bacteria within the genus *Porphyromonas* have also been connected with various human diseases, including coronary heart disease, parotitis, oral malodor, gingivitis, periodontis, stroke, atherosclerosis, hyperlipidemia, bacterial vaginosis, intrauterine growth retardation (IUGR), and increased incidence of pre-term delivery of low birth weight infants.

The present invention provides isolated polynucleotide and isolated polypeptide molecules of *Porphyromonas* spp. More particularly, the invention provides isolated polynucleotide molecules having the nucleotide sequence of *Porphyromonas* spp. fimA and oprF genes or degenerate variants thereof and isolated polypeptide molecules having the amino acid sequences of the FimA and OprF proteins encoded by such genes, respectively.

The present invention also provides polynucleotide sequences having at least about 90% homology, preferably at least about 95%, and most preferably at least 99%, sequence identity to any of SEQ ID NOS: 95 to 102 and 111 to 119 as determined using any known standard identity algorithm. In addition, the present invention provides polynucleotide sequences that hybridize under stringent conditions to the complement of any of the polynucleotide sequences shown in SEQ ID NOS: 95 to 102 and 111 to 119.

In another specific embodiment, a nucleic acid which is hybridizable to any of the polynucleotide sequences depicted in SEQ ID No. 86 to 102 and 111 to 119, or their complements, under conditions of high stringency is provided. By way of example and not limitation, procedures using such conditions of high stringency for regions of hybridization of over 90 nucleotides are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/mL denatured salmon sperm DNA. Filters are hybridized for 48 h at 65° C. in prehybridization mixture containing 100 µg/mL denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography.

Other conditions of high stringency which may be used depend on the nature of the nucleic acid (e.g. length, GC content, etc.) and the purpose of the hybridization (detection, amplification, etc.) and are well known in the art. For example, stringent hybridization of an oligonucleotide of approximately 15-40 bases to a complementary sequence in the polymerase chain reaction (PCR) is done under the following conditions: a salt concentration of 50 mM KCl, a buffer concentration of 10 mM Tris-HCl, a Mg$^{2+}$ concentration of 1.5 mM, a pH of 7-7.5 and an annealing temperature of 55-60° C.

In a preferred specific embodiment, after hybridization, wash conditions are as follows. Each membrane is washed two times each for 30 minutes each at 45° C. in 40 mM sodium phosphate, pH 7.2, 5% SDS, 1 mM EDTA, 0.5% bovine serum albumin, followed by four washes each for 30 minutes in sodium phosphate, pH 7.2, 1% SDS, 1 mM EDTA. For high stringency hybridization, the membranes are additionally subjected to four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

The present invention further provides vaccines and vaccine formulations which, when administered to a companion animal in a therapeutically effective amount, are useful in treating or preventing (i.e., conferring resistance) to periodontal disease in a companion animal.

In one embodiment, the present invention provides a vaccine that comprises at least one attenuated (modified live) or inactivated whole cell *Porphyromonas* spp. preparation (bacterin). In another embodiment, the vaccine comprises a subunit fraction of a *Porphyromonas* spp. capable of inducing an immune response.

In a preferred embodiment the vaccine of the present invention comprises one or more subunit polypeptides or fragments or variants thereof, or one or more isolated polynucleotide sequences or fragments or variants thereof.

The attenuated (modified live) or inactivated vaccines (bacterins), or isolated subunit polypeptides, or isolated polynucleotides can be present in combination with other known vaccine formulation components such as with compatible adjuvants, diluents, or carriers.

Definitions and Abbreviations

The term "ORF" indicates "open reading frame", i.e. the coding region of a gene.

The term "Percentage of sequence identity" for nucleotide sequences and polypeptide sequences is determined by comparing two optimally aligned sequences over a comparison window, wherein optimal alignment provides the highest order match and can introduce nucleotide or amino acid additions or to the test or reference sequence. The percentage identity is determined by calculating the percentage of nucleotides—that are identical between the test and reference sequence at each position over the entire sequence. Optimal sequence alignment and percentage identity can be determined manually, or more preferably by a computer algorithm including but not limited to TBLASTN, BLASTP, FASTA, TFASTA, GAP, BESTFIT, and CLUSTALW (Altschul et al., 1990, J. Mol. Biol. 215(3):403-10; Pearson and Lipman, 1988, Proc. Natl. Acad. Sci. USA 85(8):2444-8; Thompson, et al., 1994, Nucleic Acids Res. 22(22):4673-80; Devereux et al., 1984, Nuc. Acids. Res. 12:387-395); Higgins, et al., 1996, Methods Enzymol. 266:383-402). Preferably, the NCBI Blast Server (http://www.ncbi.nlm.nih.gov) set at the default parameters is used to search multiple databases for homologous sequences.

The term "heterologous", when used herein means derived from a different bacterial species or strain.

The term "homology", "homologous", and the like, when used herein means the degree of identity shared between polynucleotide or polypeptide sequences.

The term "homologous", when used in reference to a bacterial species means the same bacterial species or strain.

The term "host cell", when used herein means a bacteria or eukaryotic cell that harbors a plasmid, virus, or other vector.

The term "isolated" when used herein means removed from its naturally occurring environment, either alone or in a heterologous host cell, or chromosome or vector (e.g., plasmid, phage, etc.).

The terms "isolated anaerobic bacteria", "isolated bacteria", "isolated bacterial strain" and the like refer to a composition in which the bacteria are substantial free of other microorganisms, e.g., in a culture, such as when separated from it naturally occurring environment.

The term "isolated polynucleotide" indicates a composition in which the isolated nucleotide comprises at least 50% of the composition by weight. More preferably, the isolated polynucleotide comprises about 95%, and most preferably 99% by weight of the composition.

The term "isolated polypeptide" indicates a composition in which the isolated polypeptide comprises at least 50% of the composition by weight. More preferably, the isolated polypeptide comprises about 95%, and most preferably 99% by weight of the composition.

The term "functionally equivalent" as utilized herein, refers to a recombinant polypeptide capable of being recognized by an antibody specific to native polypeptide produced by the bacteria which causes periodontal disease in companion animals, or a recombinant polypeptide capable of eliciting or causing a substantially similar immunological response as that of the native protein from the endogenous bacteria. Thus, an antibody raised against a functionally equivalent polypeptide also recognizes the native polypeptide produced by the bacteria which causes periodontal disease in companion animals.

The term "immunogenicity" refers to the capability of a protein or polypeptide to elicit an immune response directed specifically against the bacteria that causes periodontal disease in companion animals.

The term "antigenicity" refers to the capability of a protein or polypeptide to be immunospecifically bound by an antibody raised against the protein or polypeptide.

The term "antibody", as used herein, refers to an immunoglobulin molecule able to bind to an antigen. Antibodies can be a polyclonal mixture or monoclonal. Antibodies can be intact immunoglobulins derived from natural sources or from recombinant sources, or can be immunoreactive portions of intact immunoglobulins. Antibodies can exist in a variety of forms including, for example, as, Fv, Fab', F(ab')$_2$, as well as in single chains.

The term "companion animal", as used herein, refers to any non-human animal in captivity considered to be a pet. These may include, but are not restricted to, dogs, cats, horses, rabbits, monkeys, and rodents, including mice, rats, hamsters, gerbils, and ferrets.

The term "protection", "protecting", and the like, as used herein with respect to a vaccine, means that the vaccine prevents or reduces the symptoms of the disease caused by the organism from which the antigen(s) used in the vaccine is derived. The terms "protection" and "protecting" and the like, also mean that the vaccine can be used to "treat" the disease or one of more symptoms of the disease that already exists in a subject.

The term "therapeutically effective amount" refers to an amount of the bacteria, or a subunit, (e.g., polypeptides, polynucleotide sequences) and combinations thereof sufficient to elicit an immune response in the subject to which it is administered. The immune response can comprise, without limitation, induction of cellular and/or humoral immunity.

The term "preventing infection" means to prevent or inhibit the replication of the bacteria which cause periodontal disease in companion animals, to inhibit transmission of the bacteria, or to prevent the bacteria from establishing itself in its host, or to alleviate the symptoms of the disease caused by infection. The treatment is considered therapeutic if there is a reduction in bacterial load.

The term "pharmaceutically acceptable carrier" refers to a carrier medium that does not interfere with the effectiveness of the biological activity of the active ingredient and is not toxic to the subject to whom it is administered.

The term "therapeutic agent" refers to any molecule, compound or treatment, preferably an antibacterial, that assists in the treatment of a bacterial infection or a disease or condition caused thereby.

The term "fragment or variant thereof" refers to partial nucleotide or amino acid sequences according to the present invention. Preferably the fragments or variants of the polypeptides that are provided in the present invention are capable of eliciting a humoral and/or cellular immune response in a companion animal. Analogs are encompassed by the term "fragment or variant thereof". Mutant polynucleotides which may possess one or more mutations which are deletions, insertions or substitutions of nucleotide residues are encompassed by the term "fragment or variant thereof". Allelic variants are encompassed by the term "fragment or variant thereof".

Isolation and Characterization of *Porphyromonas* spp.

Bacteria provided by the present invention can be obtained using known sampling, culture and isolation techniques. For example, microbial samples can be obtained from a population of companion animals, such as from dogs and cats, exhibiting periodontal disease. Evidence of periodontal disease can be observed using known measures, such as dogs with periodontal pockets >3 mm and cats with periodontal pockets >2 mm. Known parameters for characterizing periodontal disease such as dental indices (gingival index and periodontal index) and periodontal pocket depths can determined for the sample population of companion animals. Individual samples can be obtained from the periodontal pocket of a particular animal, maintained under anaerobic conditions and cultured using various known culture media.

Clinical isolates can be characterized using known techniques such as a number of biochemical tests, and 16S rRNA DNA sequence analysis to determine their genus and species. Individual isolates can be transferred to plates and antibiotic disks (Anaerobe Systems) can be placed on the agar surface to determine the antibiotic resistance patterns of each isolate. Purified colonies can also be subjected to known indole and catalase tests (Anaerobe Systems). Lipase and lecithinase production patterns can be determined for individual isolates.

The isolates can be typed based on their 16S rRNA DNA sequence. Individual, well-isolated colonies can be utilized as a template for polymerase chain reactions (PCR) amplification of the 16S rRNA region using, for example, primers D0056 and D0057 (Seq. ID No. 1 and Seq. ID NO. 2; Table 1). The resulting PCR products can be purified using available PCR preps kits (Promega Corp.; Madison, Wis.) and pooled by isolate. The purified PCR products can then be desalted and subjected to DNA sequence analysis. The resulting DNA sequences can be used to search available DNA databases. The bacterial isolates can then be typed based on the closest match identified by database searches.

TABLE 1

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 1 | D0056 | 16S rRNA | GGATTAGATACCCTGGTAGTC |
| 2 | D0057 | 16S rRNA | CCCGGGAACGTATTCACCG |
| 3 | PFZ175-AP1 | 16S rRNA | GGCTTAAGTGCCATAACGAG |
| 4 | PFZ175-AP2 | 16S rRNA | CTGGCGTCTTACGACGGCTG |
| 5 | PFZ175-AP3 | 16S rRNA | TGTCGTCAGCTCGTGCCGTG |
| 6 | D0067 | fimA | GCGCAGCAAGGCCAGCCCGG |
| 7 | D0068 | fimA | GAGCGAACCCCGCTCCCTGT |
| 8 | D0078 | fimA | GCGACGCTATATGCAAGACAATC |
| 9 | D0097 | fimA | ggcctcgagAACAAAGACAACGAAGCAGAACCC |
| 10 | D0098 | fimA | ggcaagcttACCAAATAACATTTTGTACAACACC |
| 11 | PFZ185-AP1 | fimA | TCATCCGACAATCCTGTGTG |
| 12 | PFZ185-AP2 | fimA | AGCAGCTGCTAAATCGGCTC |
| 13 | PFZ185-AP3 | fimA | TTGGCAAGACTCTTGCAGAG |
| 14 | PFZ185-AP4 | fimA | CTGCAGTCAGTTCAGTTGTC |
| 15 | PFZ186-AP1 | fimA | TACGTCAACAGGCTCTGCTG |
| 16 | PFZ186-AP2 | fimA | GACAACTGAACTAACTGCAG |
| 17 | PFZ186-AP3 | fimA | AACATAGAAACCTTGTGGAG |
| 18 | PFZ186-AP4 | fimA | TGTCGTCTGGTTGGGAAGAG |
| 19 | PFZ186-AP5 | fimA | AATCTGATTGCCTCCCTGAG |
| 20 | PFZ187-AP1 | fimA | GGGAACCGATTTAGCAGCAG |
| 21 | PFZ187-AP2 | fimA | CCAATACAGGGTAATAGGTC |
| 22 | PFZ187-AP3 | fimA | GTTGTCAATGCTTTTACCTC |
| 23 | PFZ187-AP4 | fimA | GATTGAGAATATCAAATGTG |
| 24 | PFZ187-AP5 | fimA | TTAGGCGTATAACCATTGTC |
| 25 | PFZ187-AP6 | fimA | ATTTAACGGTGCTTACACAC |
| 26 | PFZ187-AP7 | fimA | CCAATTGGCGGCCTGAGCTG |
| 27 | PFZ187-AP8 | fimA | TGGCATAGTTGGTAGGTGTG |
| 28 | PFZ187-AP9 | fimA | TGTAAGCACCGTTAAATGTG |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 29 | PFZ187-AP11 | fimA | CTGACAGGTTCTTTGACCAC |
| 30 | PFZ187-AP12 | fimA | TGTTCCTTGGTTGAGCCGTG |
| 31 | PFZ187-AP13 | fimA | GTGGTCAAAGAACCTGTCAG |
| 32 | PFZ187-AP14 | fimA | CATAAACACACAGGATTGTC |
| 33 | PFZ187-AP15 | fimA | TTGCTTCTTTGCAATGAGAC |
| 34 | PFZ187-AP16 | fimA | AGCCATGCGAGCATGTACAC |
| 35 | PFZ187-AP17 | fimA | CTGTCATGATCAAACCTGTG |
| 36 | PFZ187-AP18 | fimA | ACCGTCTGCATTCACGAGTG |
| 37 | PFZ188-AP1 | fimA | GCCTTCCAATGATGCTCCAC |
| 38 | PFZ188-AP2 | fimA | GGACGTAGACCTGCATTCTG |
| 39 | PFZ188-AP3 | fimA | CGCAATACGGGCATGAACAC |
| 40 | PFZ188-AP4 | fimA | TTATGGTTATGATGGACCTC |
| 41 | PFZ188-AP5 | fimA | TGGTACTCCTTTGAGTTCTG |
| 42 | PFZ188-AP6 | fimA | CACACTTGCGCGGTAACCAC |
| 43 | D0086 | oprF1 | ATGAAGGTAAAGTACTTAATGC |
| 44 | D0087 | oprF1 | AGATGAATTACTTGGAGCGAACGAT |
| 45 | KWK-Pg-03 | oprF1 | TTACTTGGAGCGAACGATTACAACACG |
| 46 | PFZ209-AP1 | oprF1 | TTGGTGCAGCTCACTTCGAC |
| 47 | PFZ209-AP2 | oprF1 | ACCACATCAAACATAAAGTC |
| 48 | PFZ209-AP3 | oprF1 | ACATTCGGGGCATGATACAG |
| 49 | PFZ209-AP4 | oprF1 | ATGCCATTGAGCCAATGGAC |
| 50 | PFZ210-AP1 | oprF1 | TTGACTTCATGTTCGATGTG |
| 51 | PFZ210-AP2 | oprF1 | TGCCAATGAATTTTATGCTG |
| 52 | PFZ210-AP3 | oprF1 | CGCTTGGAGAGTTCTTCGAC |
| 53 | PFZ210-AP4 | oprF1 | TATCAACGATCTGAATGGTC |
| 54 | PFZ211-AP1 | oprF1 | AACTACTTCAAGCCCTACAG |
| 55 | PFZ211-AP2 | oprF1 | CGTAACCCAAACCTACCCAC |
| 56 | PFZ211-AP3 | oprF1 | ACGGGACGCTTGCTCAACTC |
| 57 | PFZ211-AP4 | oprF1 | ATTGGGGCTTGGTAAATGAC |
| 58 | PFZ211-AP5 | oprF1 | ATACGCTCTACACGAGGCTC |
| 59 | PFZ212-AP1 | oprF1 | CCGCCATGGCTGGAGCTCAC |
| 60 | PFZ212-AP2 | oprF1 | TTTGAAACCATATCCCACAC |
| 61 | PFZ212-AP3 | oprF1 | AGTAACTTCAGGACATTCTG |
| 62 | PFZ212-AP4 | oprF1 | ACGTCCAGTTTCTTGCCCAG |
| 63 | PFZ213-AP1 | oprF1 | TTGACTTCATGTTCGATGTG |
| 64 | PFZ213-AP2 | oprF1 | TTTGTGTTGGTAACCACACAC |
| 65 | PFZ213-AP3 | oprF1 | ACAGGACGCTTAGAGAGCTC |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 66 | PFZ213-AP4 | oprF1 | ACGCGCTTATCAACGATCTG |
| 67 | PFZ213-AP5 | oprF1 | CTTCCCAAGGAACGTGTGTG |
| 68 | PFZ214-AP1 | oprF1 | ACTTTATGTTTGATGTTGTG |
| 69 | PFZ214-AP2 | oprF1 | CCAACACCGAACCAAGGCAC |
| 70 | PFZ214-AP3 | oprF1 | TCTCAACTCAGTATTCTCAG |
| 71 | PFZ214-AP4 | oprF1 | TAACCTTAATTTTGGTCGTG |
| 72 | PFZ215-AP1 | oprF1 | CACACCTACAACACTGCCAC |
| 73 | PFZ215-AP2 | oprF1 | TCAAACATGAAATCATAGTG |
| 74 | PFZ215-AP3 | oprF1 | CTCGGGGCAGAAAGCAGGAC |
| 75 | PFZ215-AP4 | oprF1 | GACTTGAACTCTCAGATCAG |
| 76 | KWK-Pg-06 | oprF1 | atgCAGGAAAATACTGTACCGGCAACG |
| 77 | KWK-Pgu-14 | oprF1 | gtgtgtcatatgCAGGAAAATACTGTACC |
| 78 | KWK-Pgu-15 | oprF1 | gtgtgttctagattaTTACTTGGAGCGAACG |
| 79 | KWK-Ps-02 | oprF1 | ACACCTGAGACTCAGACATTGC |
| 80 | KWK-Ps-03 | oprF1 | CATGCGCGAGCCTCAAAAGC |
| 81 | KWK-Ps-04b | oprF1 | CCTGCCACTCAACAGAAATCATATCAGAAGGAACTCC |
| 82 | KWK-Ps-05b | oprF1 | CTGCTCATAAGACGGCTTTTGACCGTTCTGCAGG |
| 83 | KWK-Ps-06b | oprF1 | CTTTTGACCGTTCTGCAGGACATTGGTTCTTGACTCTCC |
| 84 | D122 | fimA | TGGCTAARYTGACYGTAATGGTYTA |
| 85 | D123 | fimA | AGTTYACYAATACAGGRTAATAGGT |
| 86 | P. gulae B43 16S rRNA polynucleotide sequence | NA | CACGCAGTAAACGATGATTACTAGGAGTTTGCGATATACCGTCAAGCTTCCACAGCGAAAGCGTTAAGTAATCCACCTGGGGAGTACGCCGGCAACGGTGAAACTCAAGGAATTGACGTGGGGCCCGCACAAGCGGAGGAACATGTGGTTTAATTCGATGATACGCGAGGAACCTTACCCGGGATTGAAATGTAGACGACGGATGGTGAAAGCCGTCTTCCCTTCGGGGCGTCTATGTAGGTGCTGCATGGTTGTCGTCAGCTCGTGCCGTGAGGTGTCGGCTTAAGTGCCATAACGAGCGCAACCCACATCGGTAGTTGCTAACAGGTTTAGCTGAGGACTCTACCGAGACTGCCGTCGTAAGGCGCGAGGAAGGTGTGGATGACGTCAAATCAGCACGGCCCTTACATCGGGGCGACACACGTGTTACAATGGGAGGGACAAAGGGCAGCTACCGGGCGACCGGGTGCGAATCTCGAAACCCTTCCCCAGTTCGGATCGGAGTCTGCAACTCGACTCCGTGAAGCTGGATTCGCTAGTAATCGCGCATCAGCCATGGCGCGGTGAATAC |
| 87 | P. cansulci B46 16S rRNA polynucleotide sequence | NA | CACGCCGTAAACGATGATTACTCGGAGTATGCGATATGAGTGTATGCTTCTTAGCGAAAGCGTTAAGTAATCCACCTGGGGAGTCGTCGGCAACGATGAAACTCAAAGGAATTGACGGGGGCCCGCACAAGCGGAGGAACATGTGGTTTAATTCGATGATACGCGAGGAACCTTACCCGGGATTGAAATATAGATGACAGGCAGCGAGAGTTGTTATCCCTTC |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | GGGGCATCTATGTAGGTGCTGCATGGTT |
| | | | GTCGTCAGCTCGTGCCGTGAGGTGTCG |
| | | | CATTATTAGTTACTAACAGGTTAAGCTGA |
| | | | GGACTCTAATAAGACTGCCGGCGTAAGC |
| | | | CGTGAGGAAGGTGTGGATGACGTCAAAT |
| | | | CAGCACGGCCCTTACATCCGGGGCGAC |
| | | | ACACGTGTTACAATGGTAGGGACAAAGG |
| | | | GCAGCTACCGGGCGACCGGATGCGAAT |
| | | | CTCCAAACCCTATCCCAGTTCGGATCGG |
| | | | AGTCTGCAACTCGACTCTGTGAAGCTGG |
| | | | ATTCGCTAGTAATCGCGCATCAGCCATG |
| | | | GCGCGGTGAATAC |
| 88 | P. circumdentaria B52 16S rRNA polynucleotide sequence | NA | CACGCTGTAAACGATGAATACTAGATTTT TGCGATATACAGTAAGAGTCTAAGCGAA AGCGATAAGTATTCCACCTGGGGAGTAC GCCGGCAACGGTGAAACTCAAAGGAATT GACGGGGGCCCGCACAAGCGGAGGAAC ATGTGGTTTAATTCGATGATACGCGAGG AACCTTACCTGGGATTGAAATTTAGGAGA ACGATTTATGAAAGTAGATTTTCCCTTCG GGGCTCCTAAGTAGGTGCTGCATGGTTG TCGTCAGCTCGTGCCGTGAGGTGTCGGC TTAAGTGCCATAACGAGCGCAACCCGCG TTGATAGTTACTAACAGATAAAGCTGAGG ACTCTATCGAGACAGCCGTCGTAAGACG CGAGGAAGGGGCGGATGACGTCAAATC AGCACGGCCCTTACATCCAGGGCGACAC ACGTGTTACAATGGCAAGGACAAAGGGA AGCCACATAGCGATATGGAGCAGATCCT CAAACCTTGTCCCAGTTCGGATCGGAGT CTGCAACTCGACTCCGTGAAGCTGGATT CGCTAGTAATCGCGCATCAGCCATGGCG CGGTGAATACC |
| 89 | P. gulae B69 16S rRNA polynucleotide sequence | NA | CACGCAGTAAACGATGATTACTAGGAGT TTGCGATATACCGATAAGCTTCCACAGC GAAAGCGTTAAGTAATCCACCTGGGGAG TACGCCGGCAACGGTGAAACTCAAAGGA ATTGACGGGGGCCCGCACAAGCGGAGG AACATGTGGTTTAATTCGATGATACGCGA GGAACCTTACCCGGGATTGAAATGTAGA TGACAGATGGTGAAAGCCGTCTTCCCTT CGGGGCGTCTATGTAGGTGCTGCATGGT TGTCGTCAGCTCGTGCCGTGAGGTGTCG GCTTAAGTGCCATAACGAGCGCAACCCA TATCGGTAGTTGCTAACAGGTCAAGCTG AGGACTCTACCGAGACTGCCGTCGTAAG GCGAGAGGAAGGTGTGGATGACGTCAAA TCAGCACGGCCCTTACATCCGGGGCGAC ACACGTGTTACAATGGGAGGGACAAAGG GCAGCTACCGGGCGACCGGATGCGAAT CTCGAAACCCTTCCCCAGTTCGGATCGG AGTCTGCAACTCGACTCCGTGAAGCTGG ATTCGCTAGTAATCGCGCATCAGCCATG GCGCGGTGAATACC |
| 90 | P. circumdentaria B97 16S rRNA polynucleotide sequence | NA | CACGCTGTAAACGATGAATACTAGATTTT TGCGATATACAGTAAGAGTCTAAGCGAA AGCGATAAGTATTCCACCTGGGGAGTAC GCCGGCAACGGTGAAACTCAAAGGAATT GACGGGGGCCCGCACAAGCGGAGGAAC ATGTGGTTTAATTCGATGATACGCGAGG AACCTTACCTGGGATTGAAATTTAGGAGA ACGATTTATGAAAGTAGATTTTCCCTTCG GGGCTCCTAAGTAGGTGCTGCATGGTTG TCGTCAGCTCGTGCCGTGAGGTGTCGGC TTAAGTGCCATAACGAGCGCAACCCGCG TCGATAGTTACTAACAGGTAATGCTGAG GACTCTATCGAGACAGCCGTCGTAAGAC GAGAGGAAGGGGCGGATGACGTCAAAT CAGCACGGCCCTTACATCCAGGGCGACA CACGTGTTACAATGGCAAGGACAAAGGG |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | AAGCCACATAGCGATATGGAGCAGATCC TCAAACCTTGTCCCAGTTCGGATCGGAG TCTGCAACTCGACTCCGTGAAGCTGGAT TCGCTAGTAATCGCGCATCAGCCATGGC GCGGTGAATAC |
| 91 | P. cangingivalis B98 16S rRNA polynucleotide sequence | NA | CAGTAAACGATGATTACTCGGAGTATGC GATATATGGTATGCTCCCAAGGGAAACC GATAAGTAATCCACCTGGGGAGTACGCC GGCAACGGTGAAACTCAAAGGAATTGAC GGGGGCCCGCACAAGCGGAGGAACATG TGGTTTAATTCGATGATACGCGAGGAAC CTTACCCGGGATTGAAATGTACATGACG GTTGGGCGAGAGCCTGACTTCCCTTCGG GGCATGTATGTAGGTGCTGCATGGTTGT CGTCAGCTCGTGCCGTGAGGTGTCGGCT TAAGTGCCATAACGAGCGCAACCCACAT CGTCAGTTACTAACAGGTAGAGCTGAGG ACTCTGACGAGACTGCCGTCGTAAGGCG CGAGGAAGGTGTGGATGACGTCAAATCA GCACGGCCCTTACATCCGGGGCGACAC ACGTGTTACAATGGTAGGGACAAAGGGC AGCTACCTGGCGACAGGATGCGAATCTC CAAACCCTATCTCAGTTCGGATCGGAGT CTGCAACTCGACTCCGTGAAGCTGGATT CGCTAGTAATCGCGCATCAGCCATGGCG CGGTGAATACGTT |
| 92 | P. salivosa B104 16S rRNA polynucleotide sequence | NA | CAGTAAACGATGATAACTGGGCGTATGC GATATACAGTATGCTCCTGAGCGAAAGC GTTAAGTTATCCACCTGGGGAGTACGCC GGCAACGGTGAAACTCAAAGGAATTGAC GGGGGCCCGCACAAGCGGAGGAACATG TGGTTTAATTCGATGATACGCGAGGAAC CTTACCCGGGATTGAAATTTAGCGGACT ATGTATGAAAGTACATATCCTGTCACAAG GCCGCTAAGTAGGTGCTGCATGGTTGTC GTCAGCTCGTGCCGTGAGGTGTCGGCTT AAGTGCCATAACGAGCGCAACCCACGTT GTCAGTTACTATCGGGTAAAGCCGAGGA CTCTGACAAGACTGCCGTCGTAAGGCGC GAGGAAGGTGTGGATGACGT |
| 93 | P. denticanis B106 16S rRNA polynucleotide sequence | NA | CACGCCGTAAACGATGCTCACCGGCTCT ATGCGATAAGACAGTATGGGGCTAATAG AAATAATTAAGTGAGCCACCTGGGGAGT ACGTCGGCAACGATGAAACTCAAAGGAA TTGACGGGGGCCCGCACAAGCGGAGGA ACATGTGGTTTAATTCGATGATACGCGAG GAACCTTACCCGGGTTTAAATGTATGTTG CATTATGTAGAAATACGTATTTTCTTCGG AACTGCATACAAGGTGCTGCATGGTTGT CGTCAGCTCGTGCCGTGAGGTGTCGGG TTAAGTCCCATAACGAGCGCAACCCTTAT GATTAGTTGCTAACGGTTCAAGCCGAGC ACTCTATTCACACTGCCACCGTAAGGTG CGAGGAAGGAGGGGATGATGTCAAATCA GCACGGCCCTTATATCCGGGGCTACACA CGTGTTACAATGGTCGGTACAGCGGGTT GCATTTACGTGAGTAACAGCTAATCCCAA AAATCGGTCTCAGTTCGGATTGGAGTCT GCAACTCGACTCCATGAAGTTGGATTCG CTAGTAATCGCACATCAGCCATGGTGCG GTGAATAC |
| 94 | P. endodontalis B114 16S rRNA polynucleotide sequence | NA | CACCGCAGTAAACGATGAATACTAGATCT TTGCGATATACGGTAAGGGTCTAAGCGA AAGCGATAAGTATTCCACCTGGGGAGTA CGTCGGCAACGATGAAACTCAAAGGAAT TGACGGGGGCCCGCACAAGCGGAGGAA CATGTGGTTTAATTCGATGATACGCGAG GAACCTTACCCGGGATTGAAATTTAGCG GGCGGGCTATGAGAGTAGCCTTTCCTAC |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | GGGACTGCTAAGTAGGTGCTGCATGGTT |
| | | | GTCGTCAGCTCGTGCCGTGAGGTGTTGG |
| | | | CTTAAGTGCCATAACGAGCGCAACCCAC |
| | | | GTTGATAGTTACTAACAGTTAAAGCTGAG |
| | | | GACTCTATCGAGACAGCCGGCGTAAGCC |
| | | | GTGAGGAAGGTGTGGATGACGTCAAATC |
| | | | AGCACGGCCCTTACATCCGGGGCGACA |
| | | | CACGTGTTACAATGGTGAGGACAGCGGG |
| | | | AAGCGGCCTGGTGACAGGTAGCAGATCC |
| | | | CCAAACCTCATCCCAGTTCGGATTGGAG |
| | | | TCTGCAACTCGACTCTATGAAGCTGGATT |
| | | | CGCTAGTAATCGCGCATCAGCCATGGCG |
| | | | CGGTGAATAC |
| 95 | P. gulae B43 fimA polynucleotide sequence | NA | TCTAAATCGAAAAGATCCTAATAAAACA ATATTCACTTTTAAAACAAAAACGAGATG AAAAAGACTAAGTTTTTCTTGTTGGGACT TGCTGCCCTTGCTATGACAGCTTGTAACA AAGACAACGAAGCAGAACCCGTTGTAGA AGGTAACGCTACCATTAGCGTAGTATTGA AGACCAGCAATCCGAATCGTGCTTTCGG GGTTGCAGATGACGAAGCAAAAGTGGCT AAACTGACTGTAATGGTCTACAAGGGTG AGCAGCAGGAAGCCATCAAATCAGCCGA AAATGCAATTAAGGTTGAGAACATCAAAT GTGGTGCAGGCTCACGTACGCTGGTCGT AATGGCCAATACGGGTGGAATGGAATTG GCTGGCAAGACTCTTGCAGAGGTAAAAG CATTGACAACTGAACTAACTGCAGAAAAC CAAGAGGCTACAGGTTTGATCATGACAG CAGAGCCTGTTGACGTAACACTTGTCGC CGGCAATAACTATTATGGTTATGATGGAA CTCAGGGAGGCAATCAGATTTCGCAAGG TACTCCTCTTGAAATCAAACGTGTTCATG CCCGTATTGCGTTCACCAAGATTGAAGT GAAGATGAGCGAGTCTTATGTGAACAAA TACAACTTTACCCCCGAAAACATCTATGC ACTTGTGGCTAAGAAGAAGTCTAATCTAT TCGGTACTTCATTGGCAAATAGTGATGAT GCTTATTTGACCGGTTCTTTGACGACTTT CAACGGTGCTTATACCCCTGCAAACTATA CTCATGTCGTCTGGTTGGGAAGAGGCTA CACAGCGCCTTCCAATGATGCTCCACAA GGTTTCTATGTTTTGGAGAGTGCATACGC TCAGAATGCAGGTCTACGTCCTACCATTC TATGTGTAAAGGGTAAGCTGACAAAGCA TGATGGTACTCCTTTGAGTTCTGAGGAAA TGACAGCTGCATTCAATGCCGGCTGGAT TGTTGCAAACAATGATCCTACGACCTATT ATCCTGTATTAGTGAACTTTGAGAGC |
| 96 | P. circumdentaria B52 fimA polynucleotide sequence | NA | TAATGGAGAACAGCAGGAAGCCATCGAA TCAGCCGAAAATGCGACTAAGATTGAGA ATATCAAATGTGGTGCAGGCCAACGTAC GCTGGTCGTAATGGCCAATACGGGTGGA ATGGAATTGGCTGGCAAGACTCTTGCGA AGGTAAAAGCATTGACAACTGTACTGACT GAAGAAAACCAAGAGGCCACAGGTTTGA TCATGACAGCAGAGCCAAAAGCAATCGT TTTGAAGGCAGGCAAGAACTATATTGGAT ACGATGGAGCCGGAGAGGGCAACCACA TTGAGAATGCTCCTCTTGAAATCAAACGT GTACATGCTCGCATGGCTTTCACCGAAA TTAAAGTACAGATGAGCGCAGCCTACGA TAACATTTACACATTTACCCCTGAAAAGA TTTATGGTCTCATTGCAAAGAAGCAATCT AATTTGTTCGGGGCAACACTCGTGAATG CAGACGCTAATTATCTGACAGGTTCTTTG ACCACATTTAACGGTGCTTACACACCTAC CAACTATGCCAATGTTCCTTGGTTGAGCC GTGATTACGTTGCACCTACCGCTGGTGC TCCTCAGGGCTTCTACGTATTAGAAAATG ACTACTCAGCTAACAGTGGAACTATTCAT |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | CCGACAATCCTGTGTGTTTATGGCAAACT TCAGAAAAACGGAGCCGACCTGACGGGA ACCGATTTAGCAGCAGCTCAGGCCGCCA ATTGGGTGGATGCAGAAGGCAAG |
| 97 | P. gulae B69 fimA polynucleotide sequence | NA | GGCGCAGCATAACCTCGACGAACTGCGA CACTATATGCAGGACAATCTCTAAATCGA ATAAAGATTCTAATAAAACAATATTCACTT TTAAAACAAAAACAAGATGAAAAGACTA AGTTTTTCTTGTTGGGACTTGCTGCCCTT GCTATGACAGCTTGTAACAAAGACAACG AAGCAGAACCCGTTGTAGAAGGTAACGC TACCATTAGCGTAGTATTGAAGACCAGCA ATCCGAATCGTGTTTTCGGGGTTGCAGA TGACGAAGCAAAAGTGGCTAAGTTGACC GTAATGGTTTATAATGGAGAACAGCAGG AAGCCATCGAATCAGCCGAAAATGCGAC TAAGATTGAGAATATCAAATGTGGTGCAG GCCAACGTACGCTGGTCGTAATGGCCAA TACGGGTGGAATGGAATTGGCTGGCAAG ACTCTTGCAGAGGTAAAAGCATTGACAA CTGTACTGACTGAAGAAAACCAAGGGGC CACAGGTTTGATCATGACAGCAGAGCCA AAAGCAATCGTTTTGAAGGCAGGCAAGA ACTATATTGGATACGATGGAGCCGGAGA GGGCAACCACATTGAGAATGCTCCTCTT GAAATCAAACGTGTACATGCTCGCATGG CTTTCACCGAAATTAAAGTACAGATGAGC GCAGCCTACGATAACATTTACACATTTAC CCCTGAAAAGATTTATGGTCTCATTGCAA AGAAGCAATCTAATTTGTTCGGGGCAAC ACTCGTGAATGCAGACGCTAATTATCTGA CAGGTTCTTTGACCACATTTAACGGTGCT TACACACCTACCAACTATGCCAATGTTCC TTGGTTGAGCCGTGATTACGTTGCACCT ACCGCTGGTGCTCCTCAGGGCTTCTACG TATTAGAAAATGACTACTCAGCTAACAGT GGAACTATTCATCCGACAATCCTGTGTGT TTATGGCAAACTTCAGAAAAACGGAGCC GACCTGACGGGAACCGATTTAGCAGCAG CTCAGGCCGCCAATTGGGTGGATGCAGA A |
| 98 | P. circumdentaria B97 fimA polynucleotide sequence | NA | TAATGGAGAACAGCAGGAAGCCATCGAA TCAGCCGAAAATGCGACTAAGATTGAGA ATATCAAATGTGGTGCAGGCCAACGTAC GCTGGTCGTAATGGCCAATACGGGTGGA ATGGAATTGGCTGGCAAGACTCTTGCAG AGGTAAAAGCATTGACAACTGTACTGACT GAAGAAAACCAAGAGGCCACAGGTTTGA TCATGACAGCAGAGCCAAAAGCAATCGT TTTGAAGGCAGGCAAGAACTATATTGGAT ACGATGGAGCCGGAGAGGGCAACCACA TTGAGAATGCTCCTCTTGAAATCAAACGT GTACATGCTCGCATGGCTTTCACCGAAA TTAAAGTACAGATGAGCGCAGCCTACGA TAACATTTACACATTTACCCCTGAAAAGA TTTATGGTCTCATTGCAAAGAAGCAATCT AATTTGTTCGGGGCAACACTCGTGAATG CAGACGCTAATTATCTGACAGGTTCTTTG ACCACATTTAACGGTGCTTACACACCTAC CAACTATGCCAATGTTCCTTGGTTGAGCC GTGATTACGTTGCACCTACCGCTGGTGC TCCTCAGGGCTTCTACGTATTAGAAAATG ACTACTCAGCTAACAGTGGAACTATTCAT CCGACAATCCTGTGTGTTTATGGCAAACT TCAGAAAAACGGAGCCGACCTGACGGGA ACCGATTTAGCAGCAGCTCAGGCCGCCA ATTGGGTGGATGCAGAAGGCAAG |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 99 | *P. cangingivalis* B98 fimA polynucleotide sequence | NA | ggcctcgagAACAAAGACAACGAAGCAGAAC CCGTTGTAGAAGGTAACGCTACCATTAG CGTAGTATTGAAGACCAGCAATCCGAAT CGTGCTTTCGGGGTTGCAGATGACGAAG CAAAAGTGGCTAAACTGACTGTAATGGT CTACAAGGGTGAGCAGCAGGAAGCCATC AAATCAGCCGAAAATGCAATTAAGGTTGA GAACATCAAATGTGGTGCAGGCTCACGT ACGCTGGTCGTAATGGCCAATACGGGTG GAATGGAATTGGCTGGCAAGACTCTTGC AGAGGTAAAAGCATTGACAACTGAACTAA CTGCAGAAAACCAAGAGGCTACAGGTTT GATCATGACAGCAGAGCCTGTTGACGTA ACACTTGTCGCCGGCAATAACTATTATGG TTATGATGGAACTCAGGGAGGCAATCAG ATTTCGCAAGGTACTCCTCTTGAAATCAA ACGTGTTCATGCCCGTATTGCGTTCACC AAGATTGAAGTGAAGATGAGCGAGTCTT ATGTGAACAAATACAACTTTACCCCCGAA AACATCTATGCACTTGTGGCTAAGAAGAA GTCTAATCTATTCGGTACTTCATTGGCAA ATAGTGATGATGCTTATTTGACCGGTTCT TTGACGACTTTCAACGGTGCTTATACCCC TGCAAACTATACTCATGTCGTCTGGTTGG GAAGAGGCTACACAGCGCCTTCCAATGA TGCTCCACAAGGTTTCTATGTTTTGGAGA GTGCATACGCTCAGAATGCAGGTCTACG TCCTACCATTCTATGTGTAAAGGGTAAGC TGACAAAGCATGATGGTACTCCTTTGAGT TCTGAGGAAATGACAGCTGCATTCAATG CCGGCTGGATTGTTGCAAACAATGATCC TACGACCTATTATCCTGTATTAGTGAACT TTGAGAGCAATAATTACACCTACACAGGT GATGCTGTTGAGAAAGGGAAAATCGTTC GTAACCACAAGTTTGACATCAATCTGACG ATCACCGGTCCTGGTACGAATAATC |
| 100 | *P. salivosa* B104 fimA polynucleotide sequence | NA | TGGCTAARTGACTGTAATGGTTTATAAT GGAGAACAGCAGGAAGCCATCRAATCAG CCGAAAATGCGACTAAGRTTGARRAYAT CAAATGTRGTGCAGGCCAACGTACGCTG GTCGTAATGGCCAATACGGGTGSAATGG AAYTGGYTGGCAAGACTCTTGCAGAGGT AAAAGCATTGACAACTGWACTGACTGMA GAAAACCAAGAGGCYRCAGGKTTGATCA TGACAGCAGAGCCAAAARCAATCGTTTT GAAGGCAGGCAAGAACTAYATTGGATAC RRTGGARCCGGAGAGGGYAAYCACATTG AGAATGMTCCTCTTRARATCAARCGTGT WCATGCTCGCATGGCTTTCACCGAAATT AAAGTRCARATGAGCGCAGCCTACGATA ACATTTACACATTYRYCCCTGAAAAGATT TATGGTCTCATTGCAAAGAAGCAATCTAA TTTGTTCGGGGCAACACTCGTRAATGCA GACGCTAATTATCTGACAGGTTCTTTGAC CACATTTAACGGTGCTTACACACCTRCCA ACTATGCCAATGTKCCTTGGYTGAGCCG TRATTACGTTGCACCTRCCGCYGRTGCT CCTCAGGGYTTCTACGTATTAGAAAATGA CTACTCAGCTAACRGTGGAACTATTCATC CGACAATCCTGTGTGTTTATGGCAAACTT CAGAAAAACGGAGCCGACYTGRCGGGA RCCGATTTAGCARCWGCTCAGGCCGCC AATTGGGTGGATGCAGAAGGCAAGACCT ATTACCCTGTATTRGTRAACT |
| 101 | *P. denticanis* B106 fimA polynucleotide sequence | | TAATGGAGAACAGCAGGAAGCCATCGAA TCAGCCGAAAATGCGACTAAGATTGAGA ATATCAAATGTGGTGCAGGCCAACGTAC GCTGGTCGTAATGGCCAATACGGGTGGA ATGGAATTGGCTGGCAAGACTCTTGCAG AGGTAAAAGCATTGACAACTGTACTGACT GAAGAAACCAAGAGGCCACAGGTTTGA |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | TCATGACAGCAGAGCCAAAAGCAATCGT |
| | | | TTTGAAGGCAGGCAAGAACTATATTGGAT |
| | | | ACGATGGAGCCGGAGAGGGCAACCACA |
| | | | TTGAGAATGCTCCTCTTGAAATCAAACGT |
| | | | GTACATGCTCGCATGGCTTTCACCGAAA |
| | | | TTAAAGTACAGATGAGCGCAGCCTACGA |
| | | | TAACATTTACACATTTACCCCTGAAAAGA |
| | | | TTTATGGTCTCATTGCAAAGAAGCAATCT |
| | | | AATTTGTTCGGGGCAACACTCGTGAATG |
| | | | CAGACGCTAATTATCTGACAGGTTCTTTG |
| | | | ACCACATTTAACGGTGCTTACACACCTAC |
| | | | CAACTATGCCAATGTTCCTTGGTTGAGCC |
| | | | GTGATTACGTTGCACCTACCGCTGGTGC |
| | | | TCCTCAGGGCTTCTACGTATTAGAAAATG |
| | | | ACTACTCAGCTAACAGTGGAACTATTCAT |
| | | | CCGACAATCCTGTGTGTTTATGGCAAACT |
| | | | TCAGAAAAACGGAGCCGACCTGACGGGA |
| | | | ACCGATTTAGCAGCAGCTCAGGCCGCCA |
| | | | ATTGGGTGGATGCAGAAGGCAAG |
| 102 | P. endodontalis B114 fimA polynucleotide sequence | NA | CAAGGGTGAGCAGCAGGAAGCCATCAAA TCAGCCGAAAATGCAATTAAGGTTGAGA ACATCAAATGTGGTGCAGGCTCACGTAC GCTGGTCGTAATGGCCAATACGGGTGGA ATGGAATTGGCTGGCAAGACTCTTGCAG AGGTAAAAGCATTGACAACTGAACTAACT GCAGAAAACCAAGAGGCTACAGGTTTGA TCATGACAGCAGAGCCTGTTGACGTAAC ACTTGTCGCCGGCAATAACTATTATGGTT ATGATGGAACTCAGGGAGGCAATCAGAT TTCGCAAGGTACTCCTCTTGAAATCAAAC GTGTTCATGCCCGTATTGCGTTCACCAA GATTGAAGTGAAGATGAGCGAGTCTTAT GTGAACAAATACAACTTTACCCCCGAAAA CATCTATGCACTTGTGGCTAAGAAGAAGT CTAATCTATTCGGTACTTCATTGGCAAAT AGTGATGATGCTTATTTGACCGGTTCTTT GACGACTTTCAACGGTGCTTATACCCCT GCAAACTATACTCATGTCGTCTGGTTGG GAAGAGGCTACACAGCGCTTCCAATGA TGCTCCACAAGGTTTCTATGTTTTGGAGA GTGCATACGCTCAGAATGCAGGTCTACG TCCTACCATTCTATGTGTAAAGGGTAAGC TGACAAAGCATGATGGTACTCCTTTGAGT TCTGAGGAAATGACAGCTGCATTCAATG CCGGCTGGATTGTTGCAAACAATGATCC TACG |
| 103 | P. gulae B43 FimA polypeptide sequence | NA | MKKTKFFLLGLAALAMTACNKDNEAEPVV EGNATISVVLKTSNPNRAFGVADDEAKVAK LTVMVYKGEQQEAIKSAENAIKVENIKCGA GSRTLVVMANTGGMELAGKTLAEVKALTT ELTAENQEATGLIMTAEPVDVTLVAGNNYY GYDGTQGGNQISQGTPLEIKRVHARIAFTKI EVKMSESYVNKYNFTPENIYALVAKKKSNL FGTSLANSDDAYLTGSLTTFNGAYTPANYT HVVWLGRGYTAPSNDAPQGFYVLESAYA QNAGLRPTILCVKGKLTKHDGTPLSSEEMT AAFNAGWIVANNDPTTYYPVLVNFESNNY TYTGDAVEKGKIVRNHKFDINLTITGPGTNN PENPITESANLNVNCVVAAWKGVVQNVIW |
| 104 | P. circumdentaria B52 FimA polypeptide sequence | NA | NGEQQEAIESAENATKIENIKCGAGQRTLV VMANTGGMELAGKTLAEVKALTTVLTEEN QEATGLIMTAEPKAIVLKAGKNYIGYDGAG EGNHIENAPLEIKRVHARMAFTEIKVQMSA AYDNIYTFTPEKIYGLIAKKQSNLFGATLVN ADANYLTGSLTTFNGAYTPTNYANVPWLS RDYVAPTAGAPQGFYVLENDYSANSGTIH PTILCVYGKLQKNGADLTGTDLAAAQAAN WVDAEG |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 105 | P. gulae B69 FimA AA | NA | MKKTKFFLLGLAALAMTACNKDNEAEPVV EGNATISVVLKTSNPNRVFGVADDEAKVAK LTVMVYNGEQQEAIESAENATKIENIKCGA GQRTLVVMANTGGMELAGKTLAEVKALTT VLTEENQGATGLIMTAEPKAIVLKAGKNYIG YDGAGEGNHIENAPLEIKRVHARMAFTEIK VQMSAAYDNIYTFTPEKIYGLIAKKQSNLFG ATLVNADANYLTGSLTTFNGAYTPTNYANV PWLSRDYVAPTAGAPQGFYVLENDYSANS GTIHPTILCVYGKLQKNGADLTGTDLAAAQ AANWVDAEGKTYYPVLVNFSNNYTYDN GYTPKNKIERNHKYDIKLTITGPGTNNPENP ITESAHLNVQCTVAEWVLVGQNATW |
| 106 | P. circumdentaria B97 FimA polypeptide sequence | NA | NGEQQEAIESAENATKIENIKCGAGQRTLV VMANTGGMELAGKTLAEVKALTTVLTEEN QEATGLIMTAEPKAIVLKAGKNYIGYDGAG EGNHIENAPLEIKRVHARMAFTEIKVQMSA AYDNIYTFTPEKIYGLIAKKQSNLFGATLVN ADANYLTGSLTTFNGAYTPTNYANVPWLS RDYVAPTAGAPQGFYVLENDYSANSGTIH PTILCVYGKLQKNGADLTGTDLAAAQAAN WVDAEG |
| 107 | P. cangingivalis B98 FimA AA | NA | VVEGNATISVVLKTSNPNRAFGVADDEAKV AKLTVMVYKGEQQEAIKSAENAIKVENIKC GAGSRTLVVMANTGGMELAGKTLAEVKAL TTELTAENQEATGLIMTAEPVDVTLVAGNN YYGYDGTQGGNQISQGTPLEIKRVHARIAF TKIEVKMSESYVNKYNFTPENIYALVAKKKS NLFGTSLANSDDAYLTGSLTTFNGAYTPAN YTHVVWLGRGYTAPSNDAPQGFYVLESAY AQNAGLRPTILCVKGKLTKHDGTPLSSEEM TAAFNAGWIVANNDPTTYYPVLVNFESNN YTYTGDAVEKGKIVRNHKFDINLTITGPGTN NPENPITESANLNVNCVVAAWK |
| 108 | P. salivosa B104 FimA polypeptide sequence | NA | AXLTVMVYNGEQQEAIXSAENATKXXXIKC XAGQRTLVVMANTGXMEXXGKTLAEVKAL TTXLTXENQEAXGLIMTAEPKXIVLKAGKNX IGYXGXGEGXHIENXPLXIXRVHARMAFTEI KVXMSAAYDNIYTXXPEKIYGLIAKKQSNLF GATLVNADANYLTGSLTTFNGAYTPXNYA NVPWXSRXYVAPAXAPQGFYVLENDYSA NXGTIHPTILCVYGKLQKNGADXXGXDLAX AQAANWVDAEGKTYYPVXVN |
| 109 | P. denticanis B106 FimA polypeptide sequence | NA | NGEQQEAIESAENATKIENIKCGAGQRTLV VMANTGGMELAGKTLAEVKALTTVLTEEN QEATGLIMTAEPKAIVLKAGKNYIGYDGAG EGNHIENAPLEIKRVHARMAFTEIKVQMSA AYDNIYTFTPEKIYGLIAKKQSNLFGATLVN ADANYLTGSLTTFNGAYTPTNYANVPWLS RDYVAPTAGAPQGFYVLENDYSANSGTIH PTILCVYGKLQKNGADLTGTDLAAAQAAN WVDAEG |
| 110 | P. endodontalis B114 FimA polypeptide sequence | NA | KGEQQEAIKSAENAIKVENIKCGAGSRTLV VMANTGGMELAGKTLAEVKALTTELTAEN QEATGLIMTAEPVDVTLVAGNNYYGYDGT QGGNQISQGTPLEIKRVHARIAFTKIEVKMS ESYVNKYNFTPENIYALVAKKKSNLFGTSL ANSDDAYLTGSLTTFNGAYTPANYTHVVW LGRGYTAPSNDAPQGFYVLESAYAQNAGL RPTILCVKGKLTKHDGTPLSSEEMTAAFNA GWIVANNDPT |
| 111 | P. gulae B43 oprF polynucleotide sequence | NA | ACATTCGTTGGAGCTATTGCACTGAATGC AAGTGCACAGGAAAATACTGTACCGGCA ACGGGTCAGTTACCCGCCAAAAATGTTG CTTTCGCTCGCAACAAAGCAGGCAGCAA TTGGTTCGTAACACTGCAGGGCGGTGTT GCAGCGCAGTTCCTCAATGACAACAACA |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | ACAAAGATTTTGTAGACCGCTTGGGTGC |
| | | | TGCCGGCTCTATTTCAGTTGGAAAATATC |
| | | | ACAATCCATTCTTTGCAACCCGTTTGCAA |
| | | | ATTAACGGAGCTCAGGCACACACGTTCC |
| | | | TTGGAAAAAATGCGGAACAAGAAATTAAG |
| | | | ACCAATTTTGGCGCAGCTCACTTTGACTT |
| | | | CATGTTCGATGTGGTTAATTACTTTGCGC |
| | | | CATATCGCGAAAATCGTTTCTTCCATTTA |
| | | | ATTCCATGGGTAGGTGTTGGTTACCAGC |
| | | | ATAAATTCATTGGCAGCAAATGGAGTAAA |
| | | | GACAATGTCGAGTCTCTGACTGCCAATC |
| | | | TGGGTGTTATGATGGCTTTCAGATTAGGA |
| | | | AAACGTGTAGACTTTGTGATCGAAGCAC |
| | | | AAGCAGCACACTCCAATCTCAACTTAAGC |
| | | | CGTGCTTTCAATGCCAAGCCGACTCCTA |
| | | | TTTTCCAGGATCAGGAAGGACGTTATTAC |
| | | | AATGGATTCCAAGGAATGGCGACAGCAG |
| | | | GTCTTAACTTCCGCTTGGGTGCTGTAGG |
| | | | CTTCAATGCCATCGAGCCCATGGACTAC |
| | | | GCGCTTATCAACGATCTGAATGGTCAGA |
| | | | TTAATCGCCTGCGCAGAGAAGTCGAAGA |
| | | | ACTCTCCAAGCGTCCTGTATCATGTCCC |
| | | | GAATGCCCCGACGTTACACCCGTTACCA |
| | | | AGACAGAAAACAAGCTAACCGAGAAGGC |
| | | | TGTACTCTTCCGTTTCGACAGCTATGTTG |
| | | | TAGACAAAGACCAGCTTATCAATCTGTAT |
| | | | GACGTAGCTCAGTTTGTAAAAGAAACCAA |
| | | | CGAGCCGATTACTGTTGTAGGCTATGCT |
| | | | GATCCTACGGGTGACACTCAGTACAACG |
| | | | AAAGATTGTCTGAGCGTCGCGCAAAAGC |
| | | | CG |
| 112 | *P. cansulci* B46 oprF polynucleotide sequence | NA | ACATTGGCCGGGGTTTACGCCCTTTCAG |
| | | | CCTCTGCTCAGCAGGAGAATATGCCACG |
| | | | AATGGGGCAGACTCCCGCCAAGAATACC |
| | | | GCTTACGCTCGCTCTGAAGCCGGTGACA |
| | | | ATTGGTTTGTGACTTTGCAAGGAGGTGC |
| | | | TGCTATGCAGTTTGGGAAAGGTAACGAG |
| | | | GATGCCGACTTCTTCGACCGCCAAACTG |
| | | | TTGCTCCCACTTTTGCCGTAGGTAAATGG |
| | | | CACAATCCTTTCTTCGGGACCAGATTGCA |
| | | | AATGGGCTTGGGGGTATCTCACGACTTC |
| | | | TCGAACAACGAAGCGAAATCCAAGTTGG |
| | | | AGATGAACCACGCTCGCTATGCTAACGC |
| | | | ACACTTTGACTTTATGTTTGATGTGATTAA |
| | | | CTACTTCAAGCCCTACAGTGAGGACCGC |
| | | | GTATTCCACCTTATTCCGTGGGTAGGTTT |
| | | | GGGTTACGATCACAAGTTTGAGAAAAAC |
| | | | AGCAACTTCAAGGTGGATGCTCTTACAG |
| | | | CCAACGCCGGTTTGATGTTTGCTTTCCGT |
| | | | GTGATGGAGCGTATGGACATTGTGTTGG |
| | | | AAAGCCAGGTAATGTATTCTGACTTCAAC |
| | | | CTCAACACAGCTCTGCCCGAGCCTCGCT |
| | | | ACACAGCTTGCTCCGGCATGCTCACTGC |
| | | | CGGTTTGAACTTCCGTATAGGAAATATCG |
| | | | GATGGAGCGAGATCCTACCAATGGATTG |
| | | | GGGCTTGGTAAATGACCTGAACGGACAA |
| | | | ATCAACGCCATGCGTGCTAAGAACGCAG |
| | | | AGTTGAGCAAGCGTCCCGTTTCTTGCCC |
| | | | CGAATGCCCGGAAGTTGAGCCTCGTGTA |
| | | | GAGCGTATCAATATGCTTTCGGACAAGT |
| | | | CTGTTCTTTTCCGTGCCGGCAAGACAAC |
| | | | TGTAGACAGCGATCAAATGGTAACGATC |
| | | | TTCGACGTAGCTCAGTTTGCAAAGAAGA |
| | | | ATGGCACACAGATCACCGTTACAGGCTA |
| | | | TGCAGACAAGAAGGGCAAAGAAAGCGAT |
| | | | CGCACCTCTGAACTTCGTGCAAAAGCCG |
| | | | TAGCCAAGATTCTCACCGACAAGTACGG |
| | | | TGTACCTT |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 113 | *P. circumdentaria* B52 oprF polynucleotide sequence | NA | TCTATAATGGGAGCTACAGCACTCTCCG<br>CGAGTGCTCAACAATCTACGACACCTGA<br>GACTCAAACTTTGCCAGCTCGAAGACG<br>GCTTTTGACCGTTCCGCGGGTCACTGGT<br>TCTTGACTCTACAGGGTGGTGTAAATGC<br>ACAGTTTTTGGAAGAAAACGAGTCTCAAG<br>ACATCGTAAATCGTCTCCGTGTGATGCC<br>AACTCTTTCTTTAGGAAAGTGGCACAATC<br>CCTATTTTGCAACCCGTTTGCAAGTTTTT<br>GGGGGGCCAACCCCTACTTACTACAAGG<br>AGGTTTCTGGGGAGGTTAAGACCCTAAA<br>TACCGCCATGGCTGGAGCTCACTTTGAT<br>TTTATGTTTGATGTAGTAAACTTCTATGCA<br>AAGTATAATCCTAAACGAGTATTCCATTT<br>GATTCCTTGGTTCGGTGTGGGATATGGT<br>TTCAAATACTATAACGATTTTGCTGATTTA<br>GCTGATATGATTCAGTTTAATGAACCCTT<br>CCGTCACTCAGCAACTGCGAATGCTGGT<br>TTGATGATGAGTTTTCGCTTGGCAAAACG<br>TTTGGATTTGGTTCTGGAAGGGCAGGCT<br>ATATATTCTAACTTGAATATTGTAAAGCAA<br>GAGATAGATTATAAAGCCCCCATTATGCC<br>CTATTCAAATATCTACAACGGATTGACAG<br>GTGTCGTTACTGCAGGTCTCAACTTTAAT<br>CTCGGTCGTGTTGCTTGGGAGTCCGTAA<br>CTCCTATGGATATGGATCTTATTAATGAC<br>CTAAACGGACAAATTAACCGTTTGCGTTC<br>TGAGAATACAGAGTTGAGAAAACGTCCA<br>GTTTCTTGCCCAGAATGTCCTGAAGTTAC<br>TGCAgAGACGGAAGTAGTTACTGAAAAC<br>GTTTTAGGTGATAAGGCGATTGTTTTCAA<br>GTTTAATAGCGCAACTATTGACAAAGATC<br>AACACATTGTTTTGCAGGATATCGCTGAC<br>TTTGTTAAAGATGGCAACAAAGCTATTGT<br>TGTAATAGGCTTCGCAGATACAACAGGT<br>GATATTAATTACAATATGCATT |
| 114 | *P. gulae* B69 oprF polynucleotide sequence | NA | ACATTCGTTGGAGCTATTGCACTGAATGC<br>AAGTGCACAGGAAAATACTGTACCGGCA<br>ACGGGTCAGTTACCCGCCAAAAATGTTG<br>CTTTTGCCCGCAATAAAGCAGGCGGCAA<br>TTGGTTTGTAACACTGCAAGGTGGTGTT<br>GCAGCACAGTTCCTTAATGACAACAACAA<br>CAAAGATCTAGTAGACCGCTTAGGAGCT<br>ACCGGATCTATCTCCGTTGGAAAATATCA<br>CAATCCATTCTTTGCGACTCGTTTGCAAA<br>TTAACGGAGGTCAAGCACACACGTTCCT<br>TGGGAAGAATGCGGAACAAGAAATTAAC<br>ACCAATTTTGGAGCAGCTCACTTTGACTT<br>CATGTTCGATGTGGTTAACTACTTTGCGC<br>CATATCGCGAAAACCGTTTCTTCCATTTA<br>ATTCCATGGGTAGGTGTTGGTTACCAAC<br>ACAAATTCATCGGTAGCGAATGGAGTAA<br>AGACAACGTCGAGTCGCTGACCGCAAAC<br>ATGGGTGTTATGATGGCTTTCAGATTAGG<br>GAAGCGCGTGGACTTTGTGATCGAAGCA<br>CAAGCTGCTCACTCCAATCTTAATTTAAG<br>TCGCGCATTCAATGCCAAGAAAACTCCTA<br>TTTTCCACGATCAAGAAGGTCGCTATTAC<br>AATGGATTCCAAGGAATGGCTACAGCGG<br>GTCTTAACTTCCGCTTAGGTGCTGTTGG<br>CTTCAATGCCATCGAGCCAATGGACTAC<br>GCGCTTATCAACGATCTGAATGGTCAGA<br>TTAACCGTTTGCGCAGAGAAGTTGAAGA<br>GCTCTCTAAGCGTCCTGTATCATGCCCC<br>GAATGTCCCGATGTAACACCCGTTACTAA<br>GACAGAAAACAAGCTAACCGAGAAGGCT<br>GTACTCTTCCGCTTCGACAGCTATGTTGT<br>AGACAAAGACCAGCTGATCAATCTGTAT<br>GACGTTGCTCAGTTCGTAAAAGAAACTAA<br>CGAACCGATTACCGTTGTAGGTTATGCC |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | GATCCTACGGGCAGCACTCAGTACAACG<br>AAAGATTGTCTGAGCGTCGCGCAAAAGC<br>CG |
| 115 | *P. circumdentaria* B97 oprF polynucleotide sequence | NA | TCTGTTATGGGAGCTACAGCACTCACAG<br>TTAGTGCTCAGCAACCTACTACACCTGA<br>GACTCAGACATTGCCTGCTCATAAGACG<br>GCTTTTGACCGTTCTGCAGGACATTGGTT<br>CTTGACTCTCCAAGGTGGAGTTAGTGCT<br>CAATTTTTAGAAGAAAATGAAAGTCAAGA<br>AATCTTGAATCGTCTTCATGTTATGCCTA<br>CAATCTCTTTAGGCAAGTGGCACAATCCT<br>AATCTTGAATCGTCTTCATGTTATGCCTA<br>CAATCTCTTTAGGCAAGTGGCACAATCCT<br>TATTTTGCAACTCGTTTGCAAGTGTTCGG<br>AGGTCCTACTCCTACTTTTTATAAGAATG<br>CTGCTGGTAAGGTGATGAAGGAAAATGC<br>GGCTATGGCTGGGGCTCACTTTGACTTT<br>ATGTTTGATGTTGTGAACTACTTTGGTAA<br>GTATAATCCAAAGAGAGTCTTTCATCTTG<br>TGCCTTGGTTCGGTGTTGGATATGGCTTT<br>AAATACCATAATGATTTCGCCGAAATGAG<br>TGATATCATTAAGTTTAATGAGCCTTATC<br>GCCATTCAGCAACAGCGAATGCAGGGTT<br>GATGATGAGTTTCCGCTTAGCAAAACGT<br>CTTGATTTAGTGCTTGAAGGACAGGCTAT<br>ATATTCTAATTTGAATATTGTTAAGCAAGA<br>AATTGATTATAAAGCTCCTTCTACTCCTTA<br>TTCTCCAAATTATAATGGGCTTTTGGGAG<br>TTGTTACAGCAGGTCTTAACTTTAATCTT<br>GGTCGTGTTGCTTGGGAGACTGTTACTC<br>CCATGGATATGGATTTGATTAATGATCTT<br>AATGGTCAAATCAATCGTTTGCGTTCTGA<br>GAATACTGAGTTGAGAAAACGTCCTGTTT<br>CTTGTCCTGAATGCCCAGAAGTTTCTAAA<br>GAAACAACTGTAGTTACAGAAAATGTATT<br>GGGAGACAAAGCTATTGTTTTCAAATTTA<br>ATAGTGCAACTACAGCAAAGATCAACAT<br>ATTGTTTTGCAAGACATTGCGGACTTTGT<br>TAAGAATGGAAATAAGGGGGTTGCCGTG<br>ATAGGTTTCGCAGATGTAACAGGAGATG<br>CCAATTACAATATGCAAC |
| 116 | *P. cangingivalis* B98 oprF polynucleotide sequence | NA | GGTGGAGTTAGTGCTCAATTTTTAGAAGA<br>AAATGAAAGTCAAGAAATCTTGAATCGTC<br>TTCATGTTATGCCTACAATCTCTTTAGGC<br>AAGTGGCACAATCCTTATTTTGCAACTCG<br>TTTGCAAGTGTTCGGAGGTCCTACTCCTA<br>CTTTTTATAAGAATGCTGCTGGTAAGGTG<br>ATGAAGGAAAATGCGGCTATGGCTGGGG<br>CTCACTTTGACTTTATGTTTGATGTTGTG<br>AACTACTTTGGTAAGTATAATCCAAAGAG<br>AGTCTTTCATCTTGTGCCTTGGTTCGGTG<br>TTGGATATGGCTTTAAATACCATAATGAT<br>TTCGCCGAAATGAGTGATATCATTAAGTT<br>TAATGAGCCTTATCGCCATTCAGCAACAG<br>CGAATGCAGGGTTGATGATGAGTTTCCG<br>CTTAGCAAAACGTCTTGATTTAGTGCTTG<br>AAGGACAGGCTATATATTCTAATTTGAAT<br>ATTGTTAAGCAAGAAATTGATTATAAAGC<br>TCCTTCTACTCCTTATTCTCCAAATTATAA<br>TGGGCTTTTGGGAGTTGTTACAGCAGGT<br>CTTAACTTTAATCTTGGTCGTGTTGCTTG<br>GGAGACTGTTACTCCCATGGATATGGAT<br>TTGATTAATGATCTTAATGGTCAAATCAAT<br>CGTTTGCGTTCTGAGAATACTGAGTTGA<br>GAAAACGTCCTGTTTCTTGTCCTGAATGC<br>CCAGAAGTTTCTAAAGAAACAACTGTAGT<br>TACAGAAAATGTATTGGGAGACAAAGCTA<br>TTGTTTTCAAATTTAATAGTGCAACTATCA<br>GCAAAGATCAACATATTGTTTTGCAAGAC<br>ATTGCGGACTTTGTTAAGAATGGAAATAA<br>GGGGGTTGCCGTGATAGGTTTCGCAGAT |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | GTAACAGGAGATGCCAATTACAATATGCA ACTTTCTGAACGTCGTGCTAAGGCTGTT GCGGAAGCTCTTGTGAATCAATTC |
| 117 | *P. salivosa* B104 oprF polynucleotide sequence | NA | CATTGGTTCTTGACTCTCCAAGGTGGAG TTAGTGCTCAATTTTTAGAAGAAAATGAA AGTCAAGAAATCTTGAATCGTCTTCATGT TATGCCTACAATCTCTTTAGGCAAGTGGC ACAATCCTTATTTTGCAACTCGTTTGCAA GTGTTCGGAGGTCCTACTCCTACTTTTTA TAAGAATGCTGCTGGTAAGGTGATGAAG GAAAATGCGGCTATGGCTGGGGCTCACT TTGACTTTATGTTTGATGTTGTGAACTAC TTTGGTAAGTATAATCCAAAGAGAGTCTT TCATCTTGTGCCTTGGTTCGGTGTTGGAT ATGGCTTTAAATACCATAATGATTTCGCC GAAATGAGTGATATCATTAAGTTTAATGA GCCTTATCGCCATTCAGCAACAGCGAAT GCAGGGTTGATGATGAGTTTCCGCTTAG CAAAACGTCTTGATTTAGTGCTTGAAGGA CAGGCTATATATTCTAATTTGAATATTGTT AAGCAAGAAATTGATTATAAAGCTCCTTC TACTCCTTATTCTCCAAATTATAATGGGC TTTTGGGAGTTGTTACAGCAGGTCTTAAC TTTAATCTTGGTCGTGTTGCCTGGGAGA CTATTACTCCCATGGATATGGATTTGATT AATGATCTTAATGGTCAAATCAATCGTTT GCGTTCTGAGAATACTGAGTTGAGAAAA CGTCCTGTTTCTTGTCCTGAATGCCCAGA AGTTTCTAAAGAAACAACTGTAGTTACAG AAAATGTATTGGGAGACAAAGCTATTGTT TTCAAATTTAATAGTGCAACTATCAGCAA AGATCAACATATTGTTTTGCAAGACATTG CGGACTTTGTTAAGAATGGAAATAAGGG GGTTGCCGTGATAGGTTTCGCAGATGTA ACAGGAGATGCCAATTACAATATGCAACT TTCTGAACGTCGTGCTAAGGCTGTTGCG GAAGCTCTTGTGAATCAATTC |
| 118 | *P. denticanis* B106 oprF polynucleotide sequence | NA | GCTCATAAGACGGCTTTTGACCGTTCTG CAGGACATTGGTTCTTGACTCTCCAAGG TGGAGTTAGTGCTCAATTTTTAGAAGAAA ATGAAAGTCAAGAAATCTTGAATCGTCTT CATGTTATGCCTACAATCTCTTTAGGCAA GTGGCACAATCCTTATTTTGCAACTCGTT TGCAAGTGTTCGGAGGTCCTACTCCTAC TTTTTATAAGAATGCTGCTGGTAAGGTGA TGAAGGAAAATGCGGCTATGGCTGGGGC TCACTTTGACTTTATGTTTGATGTTGTGA ACTACTTTGGTAAGTATAATCCAAAGAGA GTCTTTCATCTTGTGCCTTGGTTCGGTGT TGGATATGGCTTTAAATACCATAATGATT TCGCCGAAATGAGTGATATCATTAAGTTT AATGAGCCTTATCGCCATTCAGCAACAG CGAATGCAGGGTTGATGATGAGTTTCCG CTTAGCAAAACGTCTTGATTTAGTGCTTG AAGGACAGGCTATATATTCTAATTTGAAT ATTGTTAAGCAAGAAATTGATTATAAAGC TCCTTCTACTCCTTATTCTCCAAATTATAA TGGGCTTTTGGGAGTTGTTACAGCAGGT CTTAACTTTAATCTTGGTCGTGTTGCTTG GGAGACTGTTACTCCCATGGATATGGAT TTGATTAATGATCTTAATGGTCAAATCAAT CGTTTGCGTTCTGAGAATACTGAGTTGA GAAAACGTCCTGTTTCTTGTCCTGAATGC CCAGAAGTTTCTAAAGAAACAACTGTAGT TACAGAAAATGTATTGGGAGACAAAGCTA TTGTTTTCAAATTTAATAGTGCAACTATCA GCAAAGATCAACATATTGTTTTGCAAGAC ATTGCGGACTTTGTTAAGAATGGAAATAA GGGGGTTGCCGTGATAGGTTTCGCAGAT GTAACAGGAGATGCCAATTACAATATGCA |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | ACTTTCTGAACGTCGTGCTAAGGCTGTT GCGGAAGCTCTTGTGAATCAATTCGGAG TTCCTTCTGATATGATTT |
| 119 | P. endodontalis B114 oprF polynucleotide sequence | NA | TCAGCACTGGGGGCTTTGGCACTTACAG CTAGTGCTCAACAAACTACGAAACCAGC GAATAGTATGCCCGCATTCAAGACTGCA TTTGAACGCAGCGGCGGTCATTGGTTTC TGACAATTCAGGGTGGCCTGAGTGCTCA ACTTTTGGGTGAAAATGAAAAGATGGACT TTGGCAAGCGTCTGCTACATGCTGCCAA GGCCAGTGACAACACCCAAACAGAGGCT AGCTACCTACGCATCATGCCCACGCTCT CTGTAGGTAAATGGCATAATCCCTACTTT GCTACTCGTGTACAGCTCTTCGGTGGTC TCACTCCTCTCTACAATACTGAGGGTGG CGTTAATGTACACACCTACAACACTGCCA CGATCGGTGCCCACTATGATTTCATGTTT GATGTAGTAAACTATTTCGCCAAGTACAA CCCCAAACGTTTCTTCCACGTAATTCCTT GGGTGGGTCTTGGTTACAACTTCAAGTA TCATGATGTATTTGGATTCAAGGAGCCCT ATCGTCACTCTGTCACAGGTAACGCAGG CATGGAGTTTGCTTTCCGCCTCGGTAAG CGTGTAGACCTTGTACTCGAAGCTCAGG TAGTGTACAACAACCTGAACCTGATCAAG CAGGAAGTCGACTACGATGTAGTCACTA CTCCCTATGTACCTGCTGATACATACGCT GGTCTTATGACCATGTTTACTGCTGGTCT TAACTTCAATCTGGGCAAGGTTGAGTGG GAAACTGTTGAGCCGATGGACTACCAGC TCATAAACGACTTGAACTCTCAGATCAGC GGTCTACGTAGCGAAAACGCAGAGCTTT CCAAGCGTCCTGCTTTCTGCCCCGAGTG TCCCGAAGTAGAGGAAGTAGAAGATGTT GTTGTTGACCAGTATGTCCTCACCGACA AGGCTATCCTCTTCGACTTTGACAAGAG CAACATCCGCAAGGACCAACAAGCTCAG CTTGGTATGATTGCTGAATTCGTGAAGAA GTACAATACGCCTATCGTGGTAGTAGGC TATG |
| 120 | P. gulae B43 OprF polypeptide sequence | NA | TFVGAIALNASAQENTVPATGQLPAKNVAF ARNKAGSNWFVTLQGGVAAQFLNDNNNK DFVDRLGAAGSISVGKYHNPFFATRLQING AQAHTFLGKNAEQEIKTNFGAAHFDFMFD VVNYFAPYRENRFFHLIPWVGVGYQHKFIG SKWSKDNVESLTANLGVMMAFRLGKRVD FVIEAQAAHSNLNLSRAFNAKPTPIFQDQE GRYYNGFQGMATAGLNFRLGAVGFNAIEP MDYALINDLNGQINRLRREVEELSKRPVSC PECPDVTPVTKTENKLTEKAVLFRFDSYVV DKDQLINLYDVAQFVKETNEPITVVGYADP TGDTQYNERLSERRAKAVVDVLTGKYGVP SELISVEWKGDTTQPFNKKAWN |
| 121 | P. cansulci B46 OprF polypeptide sequence | NA | TLAGVYALSASAQQENMPRMGQTPAKNT AYARSEAGDNWFVTLQGGAAMQFGKGNE DADFFDRQTVAPTFAVGKWHNPFFGTRLQ MGLGVSHDFSNNEAKSKLEMNPFFARYANA HFDFMFDVINYFKPYSEDRVFHLIPWVGLG YDHKFEKNSNFKVDALTANAGLMFAFRVM ERMDIVLESQVMYSDFNLNTALPEPRYTAC SGMLTAGLNFRIGNIGWSEILPMDWGLVN DLNGQINAMRAKNAELSKRPVSCPECPEV EPRVERINMLSDKSVLFRAGKTTVDSDQM VTIFDVAQFAKKNGTQITVTGYADKKGKES DRTSELRAKAVAKILTDKYGVPSDRISIEWK GVSEQVYDNRDWNRVV |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 122 | *P. circumdentaria* B52 OprF polypeptide sequence | NA | SIMGATALSASAQQSTTPETQTLPARKTAF DRSAGHWFLTLQGGVNAQFLEENESQDIV NRLRVMPTLSLGKWHNPYFATRLQVFGGP TPTYYKEVSGEVKTLNTAMAGAHFDFMFD VVNFYAKYNPKRVFHLIPWFGVGYGFKYY NDFADLADMIQFNEFRHSATANAGLMMS FRLAKRLDLVLEGQAIYSNLNIVKQEIDYKA PIMPYSNIYNGLTGVVTAGLNFNLGRVAWE SVTPMDMDLINDLNGQINRLRSENTELRKR PVSCPECPEVTAETEVVTENVLGDKAIVFK FNSATIDKDQHIVLQDIADFVKDGNKAIVVI GFADTTGDINYNMHLSERRAKAVAEALVN KFGVSSDMISVEWQGETEQFNPRAWN |
| 123 | *P. gulae* B69 OprF polypeptide sequence | NA | TFVGAIALNASAQENTVPATGQLPAKNVAF ARNKAGGNWFVTLQGGVAAQFLNDNNNK DLVDRLGATGSISVGKYHNPFFATRLQING GQAHTFLGKNAEQEINTNFGAAHFDFMFD VVNYFAPYRENRFFHLIPWVGVGYQHKFIG SEWSKDNVESLTANMGVMMAFRLGKRVD FVIEAQAAHSNLNLSRAFNAKKTPIFHDQE GRYYNGFQGMATAGLNFRLGAVGFNAIEP MDYALINDLNGQINRLRREVEELSKRPVSC PECPDVTPVTKTENKLTEKAVLFRFDSYVV DKDQLINLYDVAQFVKETNEPITVVGYADP TGSTQYNERLSERRAKVVDVLTGKYGVP SELISVEWKGDSTQPFNKKAWN |
| 124 | *P. circumdentaria* B97 OprF polypeptide sequence | NA | SVMGATALTVSAQQPTTPETQTLPAHKTA FDRSAGHWFLTLQGGVSAQFLEENESQEI LNRLHVMPTISLGKWHNPYFATRLQVFGG PTPTFYKNAAGKVMKENAAMAGAHFDFMF DVVNYFGKYNPKRVFHLVPWFGVGYGFK YHNDFAEMSDIIKFNEPYRHSATANAGLM MSFRLAKRLDLVLEGQAIYSNLNIVKQEIDY KAPSTPYSPNYNGLLGVVTAGLNFNLGRV AWETVTPMDMDLINDLNGQINRLRSENTEL RKRPVSCPECPEVSKETTVVTENVLGDKAI VFKFNSATISKDQHIVLQDIADFVKNGNKG VAVIGFADVTGDANYNMQLSERRAKAVAE ALVNQFGVPSDMISVEWQGETELFEARAW N |
| 125 | *P. cangingivalis* B98 OprF polypeptide sequence | NA | GGVSAQFLEENESQEILNRLHVMPTISLGK WHNPYFATRLQVFGGPTPTFYKNAAGKV MKENAAMAGAHFDFMFDVVNYFGKYNPK RVFHLVPWFGVGYGFKYHNDFAEMSDIIKF NEPYRHSATANAGLMMSFRLAKRLDLVLE GQAIYSNLNIVKQEIDYKAPSTPYSPNYNGL LGVVTAGLNFNLGRVAWETVTPMDMDLIN DLNGQINRLRSENTELRKRPVSCPECPEV SKETTVVTENVLGDKAIVFKFNSATISKDQH IVLQDIADFVKNGNKGVAVIGFADVTGDAN YNMQLSERRAKAVAEALVNQF |
| 126 | *P. salivosa* B104 OprF polypeptide sequence | NA | HWFLTLQGGVSAQFLEENESQEILNRLHV MPTISLGKWHNPYFATRLQVFGGPTPTFY KNAAGKVMKENAAMAGAHFDFMFDVVNY FGKYNPKRVFHLVPWFGVGYGFKYHNDF AEMSDIIKFNEPYRHSATANAGLMMSFRLA KRLDLVLEGQAIYSNLNIVKQEIDYKAPSTP YSPNYNGLLGVVTAGLNFNLGRVAWETITP MDMDLINDLNGQINRLRSENTELRKRPVSC PECPEVSKETTVVTENVLGDKAIVFKFNSA TISKDQHIVLQDIADFVKNGNKGVAVIGFAD VTGDANYNMQLSERRAKAVAEALVNQF |
| 127 | *P. denticanis* B106 OprF polypeptide sequence | NA | AHKTAFDRSAGHWFLTLQGGVSAQFLEEN ESQEILNRLHVMPTISLGKWHNPYFATRLQ VFGGPTPTFYKNAAGKVMKENAAMAGAH FDFMFDVVNYFGKYNPKRVFHLVPWFGV GYGFKYHNDFAEMSDIIKFNEPYRHSATAN AGLMMSFRLAKRLDLVLEGQAIYSNLNIVK |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| | | | QEIDYKAPSTPYSPNYNGLLGVVTAGLNFN LGRVAWETVTPMDMDLINDLNGQINRLRS ENTELRKRPVSCPECPEVSKETTVVTENVL GDKAIVFKFNSATISKDQHIVLQDIADFVKN GNKGVAVIGFADVTGDANYNMQLSERRAK AVAEALVNQFGVPSDMISVEWQGET |
| 128 | P. endodontalis B114 OprF polypeptide sequence | NA | SALGALALTASAQQTTKPANSMPAFKTAFE RSGGHWFLTIQGGLSAQLLGENEKMDFGK RLLHAAKASDNTQTEASYLRIMPTLSVGKW HNPYFATRVQLFGGLTPLYNTEGGVNVHT YNTATIGAHYDFMFDVVNYFAKYNPKRFFH VIPWVGLGYNFKYDHVFGFKEPYRHSVTG NAGMEFAFRLGKRVDLVLEAQVVYNNLNLI KQEVDYDVVTTPYVPADTYAGLMTMFTAG LNFNLGKVEWETVEPMDYQLINDLNSQISR LRSENAELSKRPAFCPECPEVEEVEDVVV DQYVLTDKAILFDFDKSNIRKDQQAQLGMI AEFVKKYNTPIVVVGYADPTGKSKYNMELS KRRAQAVVNELTNRHGVPADLITMEWEGA TNKFTPPTAWN |
| 129 | P. gulae B43 FimA polypeptide fragment sequence #1 | NA | ACNKDNEAEPVV |
| 130 | P. gulae B43 FimA polypeptide fragment sequence #2 | NA | YPVLVNFESNNYTYTGDAVEK |
| 131 | P. gulae B43 FimA polypeptide fragment sequence #3 | NA | TGPGTNNPENPITESA |
| 132 | P. gulae B43 OprF polypeptide fragment sequence #1 | NA | NDNNNKDFVDRLGA |
| 133 | P. gulae B43 OprF polypeptide fragment sequence #2 | NA | DLNGQINRLRREVEELSKRPVSCPECPDV |
| 134 | P. gulae B43 OprF polypeptide fragment sequence #3 | NA | ADPTGDTQYNERLSERRAKAV |
| 135 | pBAD-HisA Amino-terminal polypeptide sequence | NA | MGGSHHHHHHGMASMTGGQMGRDLYDD DDKDRWGSELEICSQYHMGI |
| 136 | pBAD-TOPO Amino-terminal polypeptide sequence | NA | MGSGSGDDDDKLALM |

TABLE 1-continued

DNA sequence identification listing. All oligonucleotide primers were synthesized by either Gibco-BRL (USA) or Lark Technologies Inc. (USA).

| SEQ ID NO. | Name | Target | DNA Sequence |
|---|---|---|---|
| 137 | I vector Amino-terminal polypeptide sequence | NA | MGTTTTTTSLHM |

Note:
Lower case nucleotides are not present in the target DNA sequence.
They are added to the 5' region of the primer to aid in cloning.
NA, Not applicable The following companion animal periodontal isolates were deposited with the American Type Culture Collection (ATCC), 10801 University Blvd., Manassas, Va., 20110, USA, on Aug. 9, 2001: *P. gulae* B43 (PTA-3618), *P. cansulci* B46 (PTA-3619), *P. circumdentaria* B52 (PTA-3620), *P. gulae* B69 (PTA-3621), *P. circumdentaria* B97 (PTA-3622), *P. cangingivalis* B98 (PTA-3623), *P. salivosa* B104 (PTA-3624), *P. denticanis* B106 (PTA-3625), and *P. endodontalis* B114 (PTA-3626). In a preferred embodiment of the invention, an isolated polynucleotide molecule of the present invention has a nucleotide sequence selected from the group consisting of SEQ ID NOS: 86 to 102 and 111 to 119. The preferred polypeptides of the present invention have amino acid sequences selected from the group consisting of SEQ ID NOS: 103 to 110 and 120 to 128.

Cloning of *Porphyromonas* Nucleotide Sequences

There are several known methods or techniques that can be used to clone the *Porphyromonas* nucleotide sequences of the present invention. For example, the sequences can be isolated as restriction fragments and cloned into cloning and/or expression vectors, the sequences can be PCR amplified and cloned into cloning and/or expression vectors, or the sequences can be cloned by a combination of these two methods.

Standard molecular biology techniques known in the art and not specifically described can be generally followed as described in Sambrook et al., *Molecular Cloning: A Laboratory Manual*, Cold Spring Harbor Laboratory Press, New York (1989); Ausubel et al., *Current Protocols in Molecular Biology*, John Wiley and Sons, Baltimore, Md. (1989); Perbal, *A Practical Guide to Molecular Cloning*, John Wiley & Sons, New York (1988); Watson et al., *Recombinant DNA*, Scientific American Books, New York; Birren et al (eds) *Genome Analysis: A Laboratory Manual Series*, Vols. 1-4 Cold Spring Harbor Laboratory Press, New York (1998); and methodology set forth in U.S. Pat. Nos. 4,666,828; 4,683, 202; 4,801,531; 5,192,659 and 5,272,057. Polymerase chain reaction (PCR) is carried out generally as described in *PCR Protocols: A Guide To Methods And Applications*, Academic Press, San Diego, Calif. (1990).

Examples of methods useful in cloning and sequencing the polynucleotides of the present invention are provided in the Example.

fimA and oprF-Encoded Polypeptides and Proteins

The present invention encompasses the use of prokaryotic and eukaryotic expression systems, including vectors and host cells, which may be used to express both truncated and full-length (native protein) forms of the recombinant polypeptides expressed by the nucleotide sequences of the present invention.

In a preferred embodiment of the invention, an isolated polynucleotide molecule of the present invention has a nucleotide sequence selected from one of the sequences of SEQ ID NO:95 to 102 and 111 to 119 or degenerate variants thereof; and encoding a corresponding polypeptide selected from the amino acid sequences of SEQ ID NO:103 to 110 and 120 to 128, respectively.

A variety of host-expression vector systems may be utilized to express the polypeptides of the present invention. Such host-expression systems also represent vehicles by which the coding sequences of interest may be cloned and subsequently purified. The present invention further provides for host cells which may, when transformed or transfected with the appropriate vector or nucleotide sequence, express the encoded polypeptide gene product of the invention. Such host cells, include but are not limited to, microorganisms such as bacteria (e.g., *E. coli, B. subtilis*) transformed with recombinant bacteriophage DNA, plasmid DNA or cosmid DNA expression vectors containing coding sequences; yeast (e.g., Saccharomyces, Pichia) transformed with recombinant yeast expression vectors containing the gene product coding sequences; insect cell systems infected with recombinant virus expression vectors (e.g., baculovirus) containing the coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In a preferred embodiment, the expression system is a bacterial system. A number of expression vectors may be advantageously selected depending upon the use intended for the product being expressed. For example, when a large quantity of such a polypeptide is to be produced, for the generation of vaccine compositions or for raising antibodies, for example, vectors which direct the expression of high levels of fusion protein products that are readily purified may be desirable. Preferably, the vectors contain promoters that direct inducible gene expression. Suitable vectors include, but are not limited to, the *E. coli* pET expression vectors (Studier and Moffatt, 1986, J. Mol. Biol. 189:113; Rosenberg et al., 1987, Gene 56:125-135; Novagen, Madison, Wis.), in which the coding sequence can be fused in-frame to a sequence encoding multiple (e.g., 6) histidine residues; pBAD vectors (Guzman et al., 1995, J. Bact. 177:4121-4130), from which a heterologous protein can be expressed under the control of an arabinose inducible protein; and pGEX vectors (Pharmacia Biotech, USA), used to express heterologous polypeptides as fusion proteins with glutathione S-transferase (GST). The fimA or oprF sequences of the present invention can be cloned into a λ expression vector and expressed in λ⁻ bacterial strains. In a preferred mode, the bacterial strain is *E. coli* BL21 (Gibco-BRL, USA). Preferably, the vectors that can be used include, but are not limited to, pLEX expression vectors (LaVallie et al., 1992, Bio/Technology 11:187-193; Mieschendahl et al., 1986, Bio/Technology 4:802-808; Invitrogen) and pRIT2T expression vectors (Nilsson et al., 1985, EMBO 4:1075; Zabeau and Stanley, 1982, EMBO 1:1217; Pharmacia Biotech). Other vectors and bacterial strains can be used and are known to those skilled in the art.

Antibody Production

Antibodies may either be monoclonal, polyclonal, or recombinant. Conveniently, the antibodies may be prepared against he immunogen or portion thereof, for example, a synthetic peptide based on the seqtuence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992. Antibody fragments may also be prepared from the antibodies and include Fab, F(ab')$_2$, and Fv by methods known to those skilled in the art.

In the production of antibodies, screening for the desired antibody can be accomplished by standard methods in immunology known in the art. Techniques not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980). In general, ELISAs and Western blotting are the preferred types of immunoassays. Both assays are well known to those skilled in the art. Both polyclonal and monoclonal antibodies can be used in the assays. The antibody can be bound to a solid support substrate or conjugated with a detectable moiety or be both bound and conjugated as is well known in the art (for a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art (see for a general discussion, Harlow & Lane *Antibodies: A Laboratory Manual*, Cold Spring Harbor Laboratory Publications, New York, 1988 and Borrebaeck, *Antibody Engineering—A Practical Guide,* W. H. Freeman and Co., 1992). The detectable moieties contemplated for use in the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$ and iodination.

Where appropriate, other immunoassays such as radioimmunoassays (RIA) can be used as known in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521, as well as Sambrook et al, *Molecular Cloning: A Laboratory Manual,* Cold Springs Harbor, N.Y., 1989.

Detection, Diagnostic, and Prevention Kits

The present invention further provides kits for the detection of *Porphyromonas* spp. The kit includes reagents for analyzing a sample for the presence of *Porphyromonas* organisms, polypeptides, or *Porphyromonas* nucleotide sequences of the present invention, wherein the presence of the nucleotide sequence is indicative of the presence of the organism. This method is valuable because disease can be diagnosed prior to the existence of symptoms and can therefore prevent the onset of the disease prior to the occurrence of damage to the patient. The presence of the *Porphyromonas* spp. Bacteria, polypeptides, or nucleotide sequences can be determined using antibodies, PCR, hybridization, and other detection methods known to those of skill in the art.

In one embodiment, the kit provides reagents for the detection of antibodies against *Porphyromonas*. In certain embodiments, the kit can include a set of printed instructions or a label indicating that the kit is useful for the detection of *Porphyromonas* spp. Minimally, the kit comprises in at least one container a protein having an amino acid sequence comprising at least 30 contiguous amino acids of any of the polypeptides of SEQ ID NO: 103 to 110 and 120 to 128. In one embodiment, the kit further comprises a secondary antibody. In a preferred embodiment, the secondary antibody is conjugated to a detectable moiety, such as, e.g., an enzyme that catalyzes a colorimetric or chemiluminescent reaction, such as alkaline phosphatase or horseradish peroxidase. In a further embodiment, the kit comprises reagents for carrying out a colorimetric or chemiluminescent assay.

In another embodiment, the kit provides reagents for the detection of *Porphyromonas* nucleic acids. In one embodiment, the kit provides reagents for the PCR detection of *Porphyromonas* nucleic acids and comprises in at least one container a first isolated DNA molecule comprising a fragment of at least about 15, 20, 25 or 30 nucleotides, which fragment hybridizes under stringent conditions to a DNA molecule encoding a polypeptide comprising a sequence of at least 5, 10, 15, 20, 25, or 30 contiguous amino acids, or the complete amino acid sequence, of any of the polypeptides of SEQ ID NO:xx-yy, and a second isolated DNA molecule comprising a fragment of at least 15, 20, 25, or 30 nucleotides, which fragment hybridizes under stringent conditions to a DNA molecule complementary to a DNA molecule encoding a polypeptide having a sequence of at least 5 10, 15, 20, 25, or 30 contiguous amino acids, or the complete amino acid sequence, of any of the polypeptides of SEQ ID NO:xx-yy, which first and second DNA molecules can be used to specifically amplify a *Porphyromonas* spp. nucleic acid encoding a 16S rRNA which 16S rRNA is encoded by a DNA molecule selected from the group consisting of SEQ ID NOS: 1-9.

In an further embodiment, the present invention provides a kit comprising in at least one container an isolated DNA molecule comprising a nucleotide sequence of at least about 15 contiguous nucleotides selected from any of SEQ ID NOS: 86 to 94, 95 to 102, and 111 to 119 which hybridizes under highly stringent conditions to the complement of any of the nucleotide sequences depicted in SEQ ID NOS: 86 to 94, 95 to 102, and 111 to 119, and a second isolated DNA molecule comprising in a second container an isolated DNA molecule comprising a nucleotide sequence of at least about 15 contiguous nucleotides selected from the complement of any of the nucleotide sequences depicted in SEQ ID NOS: 86 to 94, 95 to 102, and 111 to 119 which hybridizes under highly stringent conditions to any of the nucleotide sequences depicted in SEQ ID NOS: 86 to 94, 95 to 102, and 111 to 119, wherein the kit further comprises a set of instructions indicating that the kit is useful for the detection of *Porphyromonas* spp.

Vaccine Formulation and Method of Administration

The vaccine of the present invention can be is administered to a companion animal in an effective amount such that the vaccine therapeutically treats or confers resistance to or prevents periodontal disease in the companion animal. The vaccine of the present invention is useful in the control of bacteria that cause periodontal disease. The vaccines of the present invention can, in particular, be used in the field of veterinary medicine to treat companion animals and for the maintenance of public health against those bacteria described herein which are known to cause periodontal disease.

The vaccines of the present invention are of value in the control of bacteria that are injurious to, or spread or act as vectors of disease in man and companion animals, for example those described herein. The vaccines of the present invention are particularly useful in controlling bacteria that are present in companion animals for which purpose they can be administered using any known methods of administration, including, but not limited to, oral, parenteral, intranasal, subcutaneous, or topical.

According to a further aspect of the present invention, there is provided a composition comprising a vaccine of the present invention, in admixture with a compatible adjuvant, diluent or carrier. In a preferred embodiment, the vaccine formulation of the present invention is composed of an aqueous suspension or solution containing at least one bacteria of the present invention and/or at least one subunit protein, preferably buffered at physiological pH, in a form ready for injection.

The present invention further provides a method of treating or preventing a bacterial infection, which comprises treatment with an effective amount of a vaccine or vaccine formulation of the present invention. It is to be appreciated that reference to treatment includes prophylaxis as well as the alleviation of established symptoms of a bacterial infection.

The vaccines and vaccine formulations of the present invention can used to induce a response that prevents the pathological changes characteristic of periodontal disease caused by periodontal disease-causing bacteria. In a vaccine formulation, an immunogenic amount of the bacteria, purified protein, nucleic acid, or combinations thereof is desirably mixed with a suitable conventional vaccine adjuvants and physiologic vehicles, for use in mammals.

A vaccine formulation for preventing periodontal disease in companion animals can be produced using at least one of the isolated and purified inactivated or attenuated bacteria, purified polypeptides (such as native proteins, subunit proteins, or polypeptides, and admixing one or more or these with a compatible adjuvant, diluent, or carrier. Preferably, the polypeptide sequences are subunit proteins selected from the group including FimA (SEQ ID NOS: 103 to 110 and OprF (SEQ ID NOS: 120 to 128).

Examples of fragments of FimA and OprF that can be used for diagnostic polypeptides or for vaccine preparations include, but are not limited to ACNKDNEAEPVV, YPVLVNFESNNYTYTGDAVEK, TGPGTNNPENPITESA, NDNNNKDFVDRLGA, DLNGQINRLRREVEELSKRPVSCPECPDV, and ADPTGDTQYNERLSERRAKAV (SEQ ID NOS: 129-134). The subunit protein can be recombinantly expressed, either alone or fused to another polypeptide sequence or protein. The other polypeptide sequence or protein can include, but is not limited to, a poly-His tag, MBP, thioredoxin, or GST, for example. Also provided by the present invention are the polynucleotide sequences or genes that encode any of the above mentioned subunit proteins. The polynucleotide sequence of the bacteria can be selected from fimA and oprF or a fragment or variant thereof which fragment or variant exhibits at least about 90%, 95%, or 99% homology thereto, or a complementary polynucleotide sequence which hybridizes under high stringency conditions, or a combination of both. Preferably, the polynucleotide sequences of the present invention can be used to amplify a fimA or oprF DNA molecule of the present invention, or encodes an amino acid fragment than can be used to raise antibodies against FimA or OprF.

For DNA-based therapy, a vehicle capable of delivering or transferring heterologous nucleic acid into a host cell may be used. The expression vehicle may include elements to control targeting, expression and transcription of the nucleic acid in a cell selective manner as is known in the art. The expression vehicle can include a promoter for controlling transcription of the heterologous material and can be either a constitutive or inducible promoter to allow selective transcription. Enhancers that may be required to obtain necessary transcription levels can optionally be included.

Vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1989, 1992); Ausubel et al., *Current Protocols in Molecular Biology,* John Wiley and Sons, Baltimore, Md. (1989); Chang et al., *Somatic Gene Therapy,* CRC Press, Ann Arbor, Mich. (1995); Vega et al., *Gene Targeting,* CRC Press, Ann Arbor, Mich. (1995); R. L. Rodriguez *Vectors: A Survey of Molecular Cloning Vectors and Their Uses,* Butterworths, Boston Mass. (1988) and include, for example, stable or transient transfection, lipofection, electroporation and infection with recombinant viral vectors.

The present invention further provides for combinations vaccines having at least one of the inactivated or attenuated bacteria, nucleotide sequences, or polypeptide sequences of the present invention, in combination with one or more additional immunogenic components. Such a combination vaccine may produce in the vaccinated animal a surprisingly greater effect than that expected by simply adding the effects of each component administered separately. Thus, a combination vaccine may stimulate a synergistic production of antibody in animals.

Vaccines of the present invention can be prepared by combination of at least one of the inactivated or attenuated bacteria, nucleotide sequences, or polypeptide sequences of the present invention, with a pharmaceutically acceptable carrier, an preferably, an adjuvant.

Suitable preparations of the vaccines of the present invention include injectables, either liquid solutions or suspensions. Solid forms suitable for solution in, or suspension in, a liquid pharmaceutically acceptable carrier prior to injection may also be prepared. The vaccine preparation may be emulsified. The active immunogenic component, is preferably mixed with an adjuvant which is pharmaceutically acceptable and compatible with the active immunogenic component. Suitable adjuvants include, but are not limited to: mineral gels, e.g., aluminum hydroxide; surface active substances such as lysolecithin; glycosides, e.g., saponin derivatives such as Quil A or GPI-0100 (U.S. Pat. No. 5,977,081); cationic surfactants such as DDA, pluronic polyols; polyanions; non-ionic block polymers, e.g., Pluronic F-127 (B.A.S.F., USA); peptides; mineral oils, e.g. Montanide ISA-50 (Seppic, Paris, France), carbopol, Amphigen (Hydronics, Omaha, Nebr. USA), Alhydrogel (Superfos Biosector, Frederikssund, Denmark) oil emulsions, e.g. an emulsion of mineral oil such as BayolF/Arlacel A and water, or an emulsion of vegetable oil, water and an emulsifier such as lecithin; alum, cholesterol, rmLT, cytokines and combinations thereof. The immunogenic component may also be incorporated into liposomes, or conjugated to polysaccharides and/or other polymers for use in a vaccine formulation. Additional substances that can be included in a product for use in the present methods include, but are not limited to one or more preservatives such as disodium or tetrasodium salt of ethylenediaminetetracetic acid (EDTA), merthiolate, and the like.

The subject to which the vaccine is administered is preferably a companion animal, most preferably, a dog or cat.

It is preferred that the vaccine of the invention, when in a vaccine formulation, be present in unit dosage form. For purposes of this invention, an immunogenic amount, when administered comprises about $1\times10^4$-$1\times10^{13}$ inactivated bacterial cells, 0.1 µg-1 mg of purified protein, or 0.1 µg-10 mg of nucleic acid. In a vaccine formulation containing multiple components, the same or lesser immunogenic amounts can usefully be employed.

Appropriate therapeutically effective doses can be determined readily by those of skill in the art based on the above immunogenic amounts, the condition being treated and the physiological characteristics of the animal. Accordingly, a vaccine preparation provides a dosage of a sterile preparation of an immunogenic amount of the active ingredient(s), where the active ingredient is at least one bacteria, protein, nucleic acid, or any combination thereof. In the presence of additional active agents, these unit dosages can be readily adjusted by those of skill in the art.

A desirable dosage regimen involves administration of at least one dose of desired vaccine composition, where the antigenic content of each fraction is as stated above. Effective doses (immunizing amounts) of the vaccines of the invention may also be extrapolated from dose-response curves derived from model test systems. The mode of administration of the vaccines of the invention can be any suitable route that delivers the vaccine to the host. These include but are not limited to oral, intradermal, intramuscular, intraperitoneal, subcutaneous, intranasal routes, and via scarification (scratching through the top layers of skin, e.g., using a bifurcated needle). However, the vaccine is preferably administered subcutaneously or by intramuscular injection. Other modes of administration can also be employed, where desired, such as intradermally, intravenously, intranasally, or intratonsillarly.

Studies have shown that, for each of the above described vaccine compositions, a primary immunization of young animals (after 8 weeks of age) is desirably initiated, with booster doses administered at 12 weeks and 16 weeks of age. Annual re-vaccination is recommended.

The vaccine of the present invention is administered and dosed in accordance with good medical practice, taking into account the clinical condition of the individual subject, the site and method of administration, scheduling of administration, subject age, sex, body weight and other factors known to medical practitioners.

The invention further provides kits for the prevention periodontal disease in companion animals. In one embodiment, the kit provides a container comprising a therapeutically effective amount of a composition which prevents periodontal disease in companion animals. Also provided in the same or different container is a pharmaceutically acceptable carrier that may be used in the composition. The kit can additionally include an adjuvant that can be used to aid in creating the response to the composition of the present invention. Also, the kit can include a dispenser for dispensing the composition, preferably in unit dosage form. The dispenser can, for example, comprise metal or plastic foil, such as a blister pack. The kit can be accompanied by a label or printed instructions describing administration of the composition to prevent periodontal disease in a companion animal. Compositions comprising a vaccine composition of the present invention formulated in a pharmaceutically acceptable carrier can also be prepared, placed in an appropriate container, and labeled for treatment of the indicated periodontal condition.

Determination of Vaccine Efficacy

The specific mechanism of protection induced by the vaccines and vaccine compositions compositions of the present invention is the induction of the antibody and/or cellular immune response in vaccinated animals, as indicated by the in vivo animal tests described below.

The bacteria, polynucleotides, polypeptides, vaccines, and vaccine compositions of the present invention may be useful in treating or preventing companion animal periodontal disease, bovine foot rot, coronary heart disease (dogs), or systemic infections (dogs). In addition, the compositions of the present invention may also be useful in treating or preventing certain illnesses in companion animals corresponding to similar illnesses in humans such as coronary heart (or vascular or artery) disease, parotitis, oral maloder, gingivitis, periodontitis, stroke, atherosclerosis, hyperlipidemia, increased incidence of pre-term delivery of low birth weight infants, bacterial vaginosis and intrauterine growth retardation (IUGR).

The present invention is further illustrated by the following non-limiting example and accompanying figures.

EXAMPLE

Companion Animal Crevicular Fluid Sample

Microbial samples were taken from dogs and cats examined at veterinary clinics for periodontal treatment, or dogs examined at either Pfizer Terre Haute or Pfizer Sandwich facilities for normal check-ups. Dogs with periodontal pockets >3 mm and cats with periodontal pockets >2 mm were included in this study. Dental indices (gingival index and periodontal index) and the periodontal pocket depths were recorded. Individual coarse absorbent paper points (Henry Schein; Melville, N.Y.) were aseptically inserted into the periodontal pocket. Upon removal, the paper points were immediately inserted into vials containing Pre-Reduced Anaerobically Sterile (PRAS) Anaerobic Dental Transport (ADT) Medium (Anaerobe Systems; Morgan Hills, Calif.).

Vials were transferred into a Bactron IV anaerobic chamber (Sheldon Manufacturing, Cornelius, Oreg.) and processed under 90% $N_2$, 5% $H_2$, 5% $CO_2$. The paper points were aseptically placed into 50 µl of PRAS Brain Heart Infusion (BHI) medium (Anaerobe Systems) and vortexed for 30 seconds. Dilutions of 1:100 and 1:1000 were prepared in BHI medium. Aliquots of 100 µl of the 1:100 and 1:1000 dilutions were spread on PRAS Burcella Blood Agar (BRU) plates (Anaerobe Systems). The plates were incubated at 37° C. in the anaerobic chamber for five to seven days. The total number of bacterial colonies and the number of Black Pigmented Anaerobic Bacteria (BPAB) colonies were counted. Individual BPAP colonies were transferred to new BRU plates and re-incubated as above.

Clinical Isolate Characterization

Each clinical isolate was subjected to a number of biochemical analyses and 16S rRNA DNA sequence analysis, using primers D0056 and D0057 (Seq. ID No. 1 and Seq. ID No. 2; Table 1), to determine genus and species. Individual isolates were streaked on BRU plates. Kanamycin, Vancomycin, and Colistin disks (Anaerobe Systems) were placed on the agar surface to determine the KVC resistance patterns of each isolate. Purified colonies were also subjected to the indole and catalase tests (Anaerobe Systems). Individual isolates were transferred to Egg Yolk Agar (EYA) plates (Anaerobe Systems) in order to determine lipase and lecithinase production patterns. This data is shown in Table 2.

TABLE 2

Canine and feline BPAB isolate characterization

| Bact. Log # | Source | Dog/Cat | Breed | Age | sex | Tooth sampled | Pocket Depth | Periodontal index | Gingivitis index | Pigment | Hemolysis | Kan | Vanc | Col | Indole | Lipase | Lecith. | Catalase | Genus/species by 16S rRNA sequence |
|---|---|---|---|---|---|---|---|---|---|---|---|---|---|---|---|---|---|---|---|
| B0029 | ATCC | NA | NA | NA | NA | NA | ND | ND | ND | Y | Y | R | S | R | Y | N | Y | ND | Porphyromonas gingivalis |
| B0030 | ATCC | NA | NA | NA | NA | NA | ND | ND | ND | Y | Y | R | S | R | Y | N | Y | ND | Porphyromonas gingivalis |
| B0031 | ATCC | NA | NA | NA | NA | NA | ND | ND | ND | Y | Y | R | ND | ND | Y | N | Y | ND | Porphyromonas circumdentaria |
| B0032 | ATCC | NA | NA | NA | NA | NA | ND | ND | ND | Light | N | ND | ND | ND | ND | N | N | ND | Porphyromonas salivosa |
| B0033 | ATCC | NA | NA | NA | NA | NA | ND | ND | ND | Tan | Y | R | R | R | Y | Y | Y/N | ND | Prevotella intermedia |
| B0034 | ATCC | NA | NA | NA | NA | NA | ND | ND | ND | Y | Y | ND | S | S | Y | ND | ND | ND | Prevotella oralis |
| B0035 | ATCC | NA | NA | NA | NA | NA | ND | ND | ND | Y | ND | R | ND | ND | ND | N | Y | ND | Porphyromonas gingivalis |
| B0040 | NCTC | D | ND | ND | ND | ND | ND | ND | ND | Y | Y | S | S | R | ND | N | Y | Ne | Porphyromonas gulae |
| B0041 | Pfizer | D | ND | ND | ND | ND | ND | ND | ND | Y | Y | R | R | R | ND | N | ND | P | Porphyromonas gulae |
| B0042 | Pfizer | D | ND | ND | ND | ND | ND | ND | ND | Y | ND | R | S | R | ND | N | ND | P | Porphyromonas gulae |
| B0043 | Pfizer | C | ND | ND | ND | ND | ND | ND | ND | Y | ND | S | S | R | ND | N | ND | Ne | Porphyromonas gulae |
| B0044 | Pfizer | C | ND | ND | ND | ND | ND | ND | ND | Y | ND | S | S | R | ND | N | ND | P | Porphyromonas gulae |
| B0045 | Pfizer | D | ND | ND | ND | ND | ND | ND | ND | Y | N | S | S | R | ND | N | ND | P | Porphyromonas gulae |
| B0046 | VHUP1B | D | YRKT | 4.5 | F | URP4 | 4 | 2 | 2 | Y | ND | S | S | R | ND | N | ND | Ne | Porphyromonas cansulci |
| B0047 | VHUP1D | D | YRKT | 4.5 | F | URP4 | 4 | 2 | 2 | Y | N | R | R | R | ND | Y | ND | Ne | Porphyromonas cansulci |
| B0048 | VHUP1G | D | YRKT | 4.5 | F | URP4 | 4 | 2 | 2 | Y | ND | S | S | R | ND | N | ND | P | Porphyromonas salivosa |
| B0049 | VHUP1G | D | YRKT | 4.5 | F | URP4 | 4 | 2 | 2 | Y | ND | R | R | R | ND | N | ND | Ne | Porphyromonas cansulci |
| B0050 | VHUP1H | D | YRKT | 4.5 | F | URP4 | 4 | 2 | 2 | Y | ND | S | S | R | ND | N | ND | P | Porphyromonas salivosa |
| B0051 | VHUP1I | D | YRKT | 4.5 | F | URP4 | 4 | 2 | 3 | Y | ND | S | S | R | ND | N | ND | Ne | Porphyromonas cansulci |
| B0052 | VHUP2A | C | DSHA | 2.5 | M | URP4 | 5 | 3 | 3 | Y | ND | S | S | ND | ND | N | ND | P | Porphyromonas circumdentaria |
| B0053 | VHUP2B | C | DSHA | 2.5 | M | URP4 | 5 | 3 | 3 | Y | ND | S | R | R | ND | N | ND | P | Porphyromonas circumdentaria |
| B0054 | VHUP2C | C | DSHA | 2.5 | M | URP4 | 5 | 3 | 3 | Y | N | R | R | R | ND | N | ND | P | Porphyromonas circumdentaria |
| B0055 | VHUP2D | C | DSHA | 2.5 | M | URP4 | 5 | 3 | 3 | Y | ND | S | R | R | ND | N | ND | P | Porphyromonas circumdentaria |
| B0056 | VHUP2E | C | DSHA | 2.5 | M | URP4 | 5 | 3 | 3 | Y | ND | R | R | R | ND | N | ND | P | Porphyromonas circumdentaria |
| B0057 | VHUP2F | C | DSHA | 2.5 | M | URP4 | 5 | 3 | 3 | Y | ND | R | S | R | ND | N | ND | P | Porphyromonas circumdentaria |
| B0069 | VHUP3A | C | DSHA | 12.5 | M | ULC | 2 | 1 | 2 | Y | ND | R | S | R | ND | N | Y | P | Porphyromonas gulae |
| B0070 | VHUP3B | C | DSHA | 12.5 | M | ULC | 2 | 1 | 2 | Y | ND | R | S | R | ND | N | N | P | Porphyromonas gulae |
| B0071 | VHUP3C | C | DSHA | 12.5 | M | ULC | 2 | 1 | 2 | Y | ND | R | S | R | ND | N | N | P | Porphyromonas gulae |
| B0072 | VHUP3D | C | DSHA | 12.5 | M | ULC | 2 | 1 | 2 | Y | ND | R | S | R | ND | N | N | P | Porphyromonas gulae |
| B0073 | VHUP3E | C | DSHA | 12.5 | M | ULC | 2 | 1 | 2 | Y | ND | R | S | R | ND | N | N | P | Porphyromonas gulae |
| B0078 | VHUP4A | D | ND | 5 | F | ULP4 | 5 | 3 | 3 | yellow | Y | R | S | R | N | N | Y | Ne | Bacteroides acidofaciens |
| B0080 | VHUP4C | D | ND | 5 | F | ULP4 | 5 | 3 | 3 | yellow | Y | R | S | R | N | N | Y | P | Bacteroides acidofaciens |
| B0083 | VHUP4F | D | ND | 5 | F | ULP4 | 5 | 3 | 3 | yellow | N | R | S | R | N | N | Y | Ne | Bacteroides acidofaciens |
| B0084 | DAH1A | D | TPOO | 15 | F | URCAN | 6 | 3 | 3 | blk | N | R | S | R | Y | N | N | Ne | Porphyromonas circumdentaria |
| B0086 | DAH1C | D | TPOO | 15 | F | URCAN | 6 | 3 | 3 | brown | N | R | S | R | P | Y | N | P | Bacteroides fragilis |
| B0087 | DAH1D | D | TPOO | 15 | F | URCAN | 6 | 3 | 3 | opaque | N | R | S | R | N | Y | N | Ne | Porphyromonas circumdentaria |
| B0089 | DAH1F | D | TPOO | 15 | F | URCAN | 6 | 3 | 3 | dk brn | N | S | S | R | N | Y | N | P | Porphyromonas gulae |
| B0090 | DAH2A | D | SSHZ | 9 | M | LRCAN | 3 | ND | 2 | lt brn | Y | R | S | R | N | Y | N | P | Porphyromonas endodontalis |
| B0092 | DAH2C | D | SSHZ | 9 | M | LRCAN | 3 | ND | 2 | dk brn | Y | S | S | R | N | N | N | P | Porphyromonas gulae |
| B0093 | DAH2D | D | SSHZ | 9 | M | LRCAN | 3 | ND | 2 | dk brn | Y | R | S | R | N | N | N | P | Pasteurella canis |
| B0095 | DAH2F | D | SSHZ | 9 | M | LRCAN | 3 | ND | 2 | blk | N | R | S | R | N | N | Y | P | Porphyromonas gulae |
| B0096 | TH1aA | D | ND | ND | M | RPM4 | 3 | ND | ND | lt blk | Y | R | S | R | N | N | N | P | Porphyromonas gulae |
| B0097 | TH1aB | D | ND | ND | M | RPM4 | 3 | ND | ND | blk | N | R | S | R | N | N | N | P | Porphyromonas circumdentaria |
| B0098 | TH1aC | D | ND | ND | M | RPM4 | 3 | ND | ND | brn | N | R | S | R | N | N | Y | P | Porphyromonas cangingivalis |
| B0103 | TH1bB | D | ND | ND | M | LM1 | 4 | ND | ND | blk/wt | Y | S | S | R | N | N | Y | Ne | Streptococcus bovis JB1 |

TABLE 2-continued

Canine and feline BPAB isolate characterization

| Bact. Log # | Source | Dog/Cat | Breed | Age | sex | Tooth sampled | Pocket Depth | Periodontal index | Gingivitis index | Pigment | Hemolysis | Kan | Vanc | Col | Indole | Lipase | Lecith. | Catalase | Genus/species by 16S rRNA sequence |
|---|---|---|---|---|---|---|---|---|---|---|---|---|---|---|---|---|---|---|---|
| B0104 | TH1bC | D | ND | ND | M | LM1 | 4 | ND | ND | fans brn | Y | R | R | R | N | Y | Y | P | Porphyromonas salivosa |
| B0105 | TH1bD | D | ND | ND | M | LM1 | 4 | ND | ND | brn | Y | R | R | R | N | Y | Y | P | Porphyromonas salivosa |
| B0106 | TH1bE | D | ND | ND | M | LM1 | 4 | ND | ND | blk | Y | s | s | s | N | N | N | Ne | Porphyromonas denticanis |
| B0107 | TH1bF | D | ND | ND | M | LM1 | 4 | ND | ND | blk | Y | R | s | s | N | Y | N | Ne | Porphyromonas denticanis |
| B0109 | TH2aB | D | ND | ND | M | LPM4 | 4 | ND | ND | dk brn | N | s | s | R | P | Y | Y | P | Porphyromonas cansulci |
| B0110 | TH2aC | D | ND | ND | M | LPM4 | 4 | ND | ND | brn | N | R | R | R | P | Y | Y | P | Porphyromonas salivosa |
| B0111 | TH2aD | D | ND | ND | M | LPM4 | 4 | ND | ND | brn | Y | s | s | s | P | Y | Y | P | Porphyromonas salivosa |
| B0112 | TH2aE | D | ND | ND | M | LPM4 | 4 | ND | ND | brn | Y | R | R | s | P | Y | Y | P | Porphyromonas salivosa |
| B0113 | TH2aF | D | ND | ND | M | LPM4 | 4 | ND | ND | blk | Y | s | s | s | N | N | N | Ne | Porphyromonas denticanis |
| B0114 | TH2aG | D | ND | ND | M | LPM4 | 4 | ND | ND | yellow | N | | | | | | | Ne | Porphyromonas endodontalis |
| B0117 | TH2bA | D | ND | ND | M | LM1 | 4 | ND | ND | dk brn | Y | R | R | R | N | N | N | Ne | Porphyromonas endodontalis |
| B0118 | TH2bD | D | ND | ND | M | LM1 | 4 | ND | ND | opaque | Y | R | R | R | N | Y | Y | P | Porphyromonas salivosa |
| B0119 | TH2bE | D | ND | ND | M | LM1 | 4 | ND | ND | yellow | N | R | R | R | N | N | N | Ne | Eubacterium brachy |
| B0121 | TH2bF | D | ND | ND | M | LM1 | 4 | ND | ND | blk | Y | s | s | s | N | Y | Y | P | Porphyromonas cansulci |
| B0122 | TH2cB | D | ND | ND | M | RM1 | 4 | ND | ND | lt brn | Y | R | R | R | N | Y | N | Ne | Porphyromonas endodontalis |
| B0123 | TH2cC | D | ND | ND | M | RM1 | 4 | ND | ND | blk | Y | R | R | R | N | Y | Y | P | Porphyromonas salivosa |
| B0124 | TH2cD | D | ND | ND | M | RM1 | 4 | ND | ND | dk brn | Y | R | R | R | N | Y | Y | P | Porphyromonas salivosa |
| B0125 | TH2cE | D | ND | ND | M | RM1 | 4 | ND | ND | blk | Y | R | R | R | N | N | N | Ne | Porphyromonas endodontalis |
| B0126 | TH2cF | D | ND | ND | M | RM1 | 4 | ND | ND | brn | Y | R | R | R | N | Y | Y | P | Porphyromonas salivosa |
| B0128 | TH3aC | D | ND | ND | M | RM1 | 4 | ND | ND | blk | Y | R | R | s | N | N | N | Ne | Porphyromonas denticanis |
| B0129 | TH3aD | D | ND | ND | M | RM1 | 4 | ND | ND | brn | Y | R | R | s | N | Y | Y | P | Porphyromonas salivosa |
| B0131 | TH3aF | D | ND | ND | M | RM1 | 4 | ND | ND | blk | Y | s | s | s | N | N | N | Ne | Porphyromonas denticanis |
| B0132 | TH3bA | D | ND | ND | M | RPM3 | 4 | ND | ND | bm | Y | R | R | R | N | Y | Y | P | Porphyromonas salivosa |
| B0133 | TH3bB | D | ND | ND | M | RPM3 | 4 | ND | ND | blk | Y | s | s | s | N | Y | Y | P | Porphyromonas cansulci |
| B0134 | TH3bC | D | ND | ND | M | RPM3 | 4 | ND | ND | bm | Y | R | R | R | N | Y | Y | P | Porphyromonas salivosa |
| B0135 | TH3bD | D | ND | ND | M | RPM3 | 4 | ND | ND | bm | Y | R | R | R | N | Y | Y | P | Porphyromonas salivosa |
| B0136 | TH3bE | D | ND | ND | M | RPM3 | 4 | ND | ND | bm | Y | R | R | R | N | N | N | Ne | Porphyromonas denticanis |
| B0140 | TH3cC | D | ND | ND | M | LM1 | 4 | ND | ND | blk | N | R | R | R | N | N | N | Ne | Porphyromonas denticanis |
| B0142 | TH3cE | D | ND | ND | M | LM1 | 4 | ND | ND | opaque | Y | R | R | R | P | Y | Y | P | Porphyromonas salivosa |
| B0143 | TH3cF | D | ND | ND | M | LM1 | 4 | ND | ND | wht | Y | ND | ND | ND | | | | Ne | Eubacterium brachy |
| B0145 | TH4aB | D | ND | ND | M | RM1 | 4 | ND | ND | blk | N | s | s | R | N | Y | Y | P | Porphyromonas gulae |
| B0146 | TH4aC | D | ND | ND | M | RM1 | 4 | ND | ND | lt brn | N | R | R | R | N | N | N | Ne | Enterococcus gallinarum |
| B0148 | TH4aE | D | ND | ND | M | RM1 | 4 | ND | ND | lt brn | N | R | R | R | N | Y | Y | P | Porphyromonas cansulci |
| B0150 | TH4bA | D | ND | ND | M | LM1 | 4 | ND | ND | blk | Y | R | R | s | P | Y | N | Ne | Porphyromonas denticanis |
| B0152 | TH4bB | D | ND | ND | M | LM1 | 4 | ND | ND | blk | Y | R | R | R | N | Y | N | Ne | Porphyromonas denticanis |
| B0153 | TH4bC | D | ND | ND | M | LM1 | 4 | ND | ND | bm | Y | R | R | R | N | Y | N | Ne | Porphyromonas denticanis |
| B0154 | TH4bD | D | ND | ND | M | LM1 | 4 | ND | ND | bm | Y | R | R | R | N | Y | Y | P | Bacteroides forsythus |
| B0155 | TH4bE | D | ND | ND | M | LM1 | 4 | ND | ND | bm | Y | R | R | R | P | Y | Y | P | Porphyromonas salivosa |
| B0163 | TH4bF | D | ND | ND | M | LPM4 | 4 | ND | ND | blk | Y | R | R | R | N | Y | N | Ne | Porphyromonas denticanis |
| B0164 | TH5bB | D | ND | ND | M | LM1 | 4 | ND | ND | blk | Y | R | R | R | N | Y | N | Ne | Porphyromonas denticanis |
| B0171 | TH5bC | D | ND | ND | M | LPM4 | 4 | ND | ND | bm | N | s | s | s | N | Y | Y | P | Eubacterium brachy |
| B0172 | TH6aD | D | ND | ND | M | RPM4 | 7 | ND | ND | blk | Y | R | R | R | N | Y | N | p | Porphyromonas denticanis |
| B0173 | TH6aE | D | ND | ND | M | RPM4 | 7 | ND | ND | blk | Y | R | R | R | N | Y | N | P | Porphyromonas denticanis |
| B0174 | TH6bA | D | ND | ND | M | LM1 | 6.5 | ND | ND | blk | Y | R | R | R | P | Y | N | Ne | Porphyromonas denticanis |

TABLE 2-continued

Canine and feline BPAB isolate characterization

| Bact. Log # | Source | Dog/Cat | Breed | Age | sex | Tooth sampled | Pocket Depth | Periodontal index | Gingivitis index | Pigment | Hemolysis | Kan | Vanc | Col | Indole | Lipase | Lecith. | Catalase | Genus/species by 16S rRNA sequence |
|---|---|---|---|---|---|---|---|---|---|---|---|---|---|---|---|---|---|---|---|
| B0183 | TH7aD | D | ND | ND | M | RPM4 | 2.5 | ND | ND | opaque | Y | R | R | S | N | N | N | Ne | *Porphyromonas denticanis* |
| B0186 | TH7bA | D | ND | ND | M | LM1 | 4 | ND | ND | blk/brn | N | R | R | R | N | N | Y | Ne | *Porphyromonas endodontalis* |
| B0187 | TH7bB | D | ND | ND | M | LM1 | 4 | ND | ND | brn | Y | R | R | R | N | N | N | Y | *Porphyromonas canoris* |
| B0188 | TH7bC | D | ND | ND | M | LM1 | 4 | ND | ND | opaque | N | R | S | R | N | Y | N | Ne | *Fusobacterium alocis* |
| B0190 | TH7bE | D | ND | ND | M | LM1 | 4 | ND | ND | brn | Y | R | R | R | N | Y | Y | P | *Porphyromonas salivosa* |
| B0191 | TH7bF | D | ND | ND | M | LM1 | 3 | ND | ND | wt | Y | R | R | R | N | Y | Y | P | *Porphyromonas salivosa* |
| B0195 | TH8aD | D | ND | ND | M | RM1 | 4 | ND | ND | blk | Y | R | R | R | P | Y | Y | Ne | *Porphyromonas circumdentaria* |
| B0198 | TH9aA | D | ND | ND | M | LPM3 | 4 | ND | ND | lt brn | Y | R | S | S | P | Y | Y | P | *Porphyromonas salivosa* |
| B0199 | TH9aB | D | ND | ND | M | LPM3 | 4 | ND | ND | brn | Y | R | S | R | N | Y | N | P | *Porphyromonas gulae* |
| B0201 | TH9aD | D | ND | ND | M | LPM3 | 4 | ND | ND | blk | Y | R | R | R | N | Y | N | P | *Campylobacter sputorum* |
| B0203 | TH9aF | D | ND | ND | M | LPM3 | 4 | ND | ND | dk brn | Y | R | R | S | N | Y | N | Ne | *Porphyromonas gulae* |
| B0204 | TH9bA | D | ND | ND | M | RPM3 | 3 | ND | ND | tan | N |   | R | R | N | Y | N | P | *Porphyromonas cangingivalis* |
| B0205 | TH9bB | D | ND | ND | M | RPM3 | 3 | ND | ND | blk | Y | R | R | R | N | Y | N | Ne | *Porphyromonas cansulci* |
| B0206 | TH9bC | D | ND | ND | M | RPM3 | 3 | ND | ND | brn | Y | R | R | R | N | Y | N | P | *Porphyromonas gulae* |
| B0207 | TH9bD | D | ND | ND | M | RPM3 | 3 | ND | ND | blk | N | R | R | R | N | Y | N | Ne | *Porphyromonas cansulci* |
| B0208 | TH9bE | D | ND | ND | M | RPM3 | 3 | ND | ND | tan | N | R | S | S | N | Y | N | P | *Porphyromonas cangingivalis* |
| B0210 | TH10aA | D | ND | ND | M | RM1 | 4 | ND | ND | opaque | N | R | R | R | N | N | N | Ne | *Campylobacter sputorum* |
| B0211 | TH10aB | D | ND | ND | M | RM1 | 4 | ND | ND | blk | N | R | R | R | N | N | N | P | *Porphyromonas circumdentaria* |
| B0212 | TH10aC | D | ND | ND | M | RM1 | 4 | ND | ND | lt brn | Y | R | S | S | N | Y | N | P | *Porphyromonas gulae* |
| B0213 | TH10aD | D | ND | ND | M | RM1 | 4 | ND | ND | blk/brn | N | R | R | R | N | Y | N | P | *Porphyromonas circumdentaria* |
| B0218 | TH10bC | D | ND | ND | M | LM1 | 4 | ND | ND | yellow | N | R | R | R | N | Y | Y | Ne | *Peptostreptococcus sp. D1* |
| B0222 | TH11aA | D | ND | ND | M | RM1 | 4 | ND | ND | blk | N | R | R | S | N | N | N | Ne | *Bacteroides levii* |
| B0225 | TH11aD | D | ND | ND | M | RM1 | 4 | ND | ND | blk | N | R | R | R | N | N | N | Ne | *Bacteroides levii* |
| B0232 | TH11bE | D | ND | ND | F | LPM3 | 2 | ND | ND | lt brn | Y | R | R | R | P | Y | N | P | *Porphyromonas canoris* |
| B0233 | TH11bF | D | ND | ND | F | LPM3 | 2 | ND | ND | brn | Y | R | R | R | N | N | Y | Y | *Klebsiella oxytoca* |
| B0234 | TH12aA | D | ND | ND | F | RPM4 | 4 | ND | ND | mixed | Y | R | R | R | P | Y | Y | P | *Porphyromonas salivosa* |
| B0235 | TH12aB | D | ND | ND | F | RPM4 | 4 | ND | ND | yellow | N | R | R | S | N | Y | Y | Ne | *Bacteroides forsythus* |
| B0236 | TH12aC | D | ND | ND | F | RPM4 | 4 | ND | ND | lt brn | Y | R | S | R | N | Y | Y | P | *Porphyromonas salivosa* |
| B0238 | TH12aE | D | ND | ND | F | RPM4 | 4 | ND | ND | lt brn | Y | R | R | R | N | Y | N | Ne | *Porphyromonas circumdentaria* |
| B0241 | TH12bB | D | ND | ND | F | ULPM4 | 4 | ND | ND | blk | Y | S | R | S | P | Y | N | Ne | *Bacteroides acidofaciens* |
| B0242 | TH12bC | D | ND | ND | F | ULPM4 | 4 | ND | ND | wht | N | R | S | S | N | Y | Y | Ne | *Bacteroides acidofaciens* |
| B0243 | TH12bD | D | ND | ND | F | ULPM4 | 4 | ND | ND | brn | Y | S | R | S | N | Y | Y | Ne | *Peptostreptococcus sp. D1* |
| B0248 | TH13aC | D | ND | ND | F | RPM4 | 4 | ND | ND | yellow | N | R | R | R | N | Y | N | Ne | *Porphyromonas endodontalis* |
| B0251 | TH13aF | D | ND | ND | M | RPM4 | 2 | ND | ND | blk | N | R | R | R | N | Y | N | P | *Porphyromonas salivosa* |
| B0258 | TH14aA | D | ND | ND | M | URPM2 | 5 | ND | ND | lt brn | N | R | R | S | P | Y | Y | P | *Porphyromonas endodontalis* |
| B0259 | TH14aB | D | ND | ND | M | URPM2 | 5 | ND | ND | lt brn | N | R | R | S | P | Y | N | Ne | *Porphyromonas endodontalis* |
| B0260 | TH14aC | D | ND | ND | M | URPM2 | 5 | ND | ND | dk brn | Y | R | R | S | P | N | Y | Ne | *Porphyromonas salivosa* |
| B0264 | TH14bA | D | ND | ND | M | ULCAN | 2 | ND | ND | blk | N | R | R | R | N | Y | N | P | *Porphyromonas denticanis* |
| B0265 | TH14bB | D | ND | ND | M | ULCAN | 2 | ND | ND | blk | Y | R | R | R | N | N | Y | Ne | *Porphyromonas circumdentaria* |
| B0266 | TH14bC | D | ND | ND | M | ULCAN | 2 | ND | ND | yellow | N | S | ND | ND | N | N | N | Ne | *Bacteroides acidofaciens* |
| B0267 | TH14bD | D | ND | ND | M | ULCAN | 2 | ND | ND | blk | N | R | S | R | P | Y | N | P | *Peptostreptococcus sp. D1* |
| B0269 | TH14bF | D | ND | ND | M | ULCAN | 2 | ND | ND | blk | N | R | ND | ND | N | ND | ND | Ne | *Porphyromonas denticanis* |
| B0270 | TH15aA | D | ND | ND | M | RM1 | 4 | ND | ND | brn | Y | R | R | R | N | N | Y | Ne | *Porphyromonas denticanis* |
| B0271 | TH15aB | D | ND | ND | M | RM1 | 4 | ND | ND | brn | N | R | S | R | N | N | Y | P | *Porphyromonas gulae* |
| B0272 | TH15aC | D | ND | ND | M | RM1 | 4 | ND | ND | gry brn | Y | R | R | R | N | N | ND | P | *Porphyromonas gulae* |
| B0273 | TH15aD | D | ND | ND | M | RM1 | 4 | ND | ND | blk | Y | R | S | R | N | N | Y | P | *Porphyromonas gulae* |

TABLE 2-continued

Canine and feline BPAB isolate characterization

| Bact. Log # | Source | Dog/Cat | Breed | Age | sex | Tooth sampled | Pocket Depth | Periodontal index | Gingivitis index | Pigment | Hemolysis | Kan | Vanc | Col | Indole | Lipase | Lecith. | Catalase | Genus/species by 16S rRNA sequence |
|---|---|---|---|---|---|---|---|---|---|---|---|---|---|---|---|---|---|---|---|
| B0274 | TH15aE | D | ND | ND | M | RM1 | 4 | ND | ND | dk brn | Y | R | s | R | N | N | Y | P | Porphyromonas gulae |
| B0279 | TH15bD | D | ND | ND | M | LM1 | 2 | ND | ND | blk | Y | R | s | R | N | Y | Y | P | Porphyromonas endodontalis |
| B0283 | TH16aB | D | ND | ND | F | RM1 | 4 | ND | ND | blk | ND | s | s | s | N | N | N | P | Porphyromonas cansulci |
| B0284 | TH16aC | D | ND | ND | F | RM1 | 4 | ND | ND | blk | ND | s | s | s | N | N | N | Ne | Unidentified eubacterium |
| B0285 | TH16aD | D | ND | ND | F | RM1 | 4 | ND | ND | blk | ND | s | s | s | N | N | N | Ne | Unidentified eubacterium |
| B0286 | TH16aE | D | ND | ND | F | RM1 | 4 | ND | ND | brn | ND | R | s | R | N | N | N | P | Porphyromonas gulae |
| B0287 | TH16aF | D | ND | ND | F | RM1 | 4 | ND | ND | blk | ND | R | s | R | N | N | Y | P | Porphyromonas circumdentaria |
| B0290 | TH16bC | D | ND | ND | F | LPM4 | 2 | ND | ND | blk | ND | R | s | R | N | N | N | Ne | Porphyromonas circumdentaria |
| B0291 | TH16bD | D | ND | ND | F | LPM4 | 2 | ND | ND | blk | ND | s | s | s | N | N | N | P | Porphyromonas gulae |
| B0323 | VHUP5F | D | DSHA | 10 | F | URCAN | 4 | 2 | ND | dk brn | ND | R | s | R | N | N | Y | P | Porphyromonas circumdentaria |
| B0336 | DAH6A | D | COLI | 10 | F | URCAN | 6 | 3 | 2 | blk | Y | R | s | R | N | N | N | P | Porphyromonas gulae |
| B0337 | DAH6B | D | COLI | 10 | F | URCAN | 6 | 3 | 3 | brn | Y | R | s | R | N | N | N | P | Porphyromonas gulae |
| B0341 | DAH6F | D | COLI | 10 | F | URCAN | 6 | 3 | 3 | blk | N | s | s | s | N | N | N | Ne | Unidentified eubacterium |
| B0342 | VHUP6A | D | SCOT | 7.5 | M | LM1 | 5 | 3 | 3 | blk | Y | s | s | s | N | N | N | Ne | Unidentified rumen bacterium |
| B0343 | VHUP6B | D | SCOT | 7.5 | M | LM1 | 5 | 3 | 2 | yellow | N | R | s | R | N | N | N | Ne | Bacteroides acidofaciens |
| B0344 | VHUP6C | D | SCOT | 7.5 | M | LM1 | 5 | 3 | 3 | lt brn | N | R | s | R | P | Y | Y | P | Bacteroides forsythus |
| B0346 | VHUP6E | D | SCOT | 7.5 | M | LM1 | 5 | 3 | 2 | blk | N | R | R | R | P | Y | N | Ne | Porphyromonas circumdentaria |
| B0348 | VHUP7A | D | CKSP | 11 | M | ULP2 | 6 | 1 | 2 | brn | N | s | s | s | N | N | N | P | Bacteroides forsythus |
| B0353 | DAH8B | D | YRKT | 11 | M | ULCAN | 9 | 2 | 3 | yellow | N | R | s | R | N | N | N | Ne | Peptostreptococcus |
| B0358 | DAH19A | D | YRKT | 9 | M | URPM4 | 6 | 3 | 3 | blk | Y | s | s | s | P | N | N | P | Porphyromonas gulae |
| B0363 | DAH19F | D | YRKT | 9 | M | URPM4 | 6 | 3 | 3 | brn | Y | R | R | R | P | Y | N | Ne | Porphyromonas salivosa |
| B0365 | DAH20B | D | DACH | 10 | F | ULM1 | 3 | 2 | 3 | blk | Y | R | R | s | P | N | N | Ne | Porphyromonas denticanis |
| B0366 | DAH20C | D | DACH | 10 | F | ULM1 | 3 | 1 | 3 | blk | N | R | R | ND | P | N | N | Ne | Porphyromonas denticanis |
| B0367 | DAH20D | D | DACH | 10 | F | ULM1 | 3 | 3 | 3 | blk | N | R | ? | ND | P | Y | N | Ne | Porphyromonas denticanis |
| B0368 | DAH24D | D | MIXB | 11 | M | LRM1 | 3 | 3 | 3 | blk | Y | R | R | ND | P | N | N | P | Porphyromonas gulae |
| B0253 | DAH37E | D | DSHA | 11 | M | URCAN | 6 | 2 | 2 | yel | Y | R | R | R | N | Y | N | P | Bacteroides forsythus |
| B0255 | CSU1B | C | DSHA | 17 | M | ND | N | ND | ND | lt brn | N | R | s | ND | N | N | N | Ne | Tessaracoccus bendigoniensis |
| B0256 | DAH39C | D | ND | ND | M | LRM1 | 6 | 2 | 3 | Blk | N | R | s | R | P | N | N | P | Bacteroides levii |
| B0375 | UCD2A | D | DACH | 11 | M | URPM3 | 5 | 1 | 2 | brn | N | R | R | ND | P | N | N | Ne | Porphyromonas salivosa |
| B0381 | UF1A | C | DSHA | 2 | F | ULPM3 | 1 | 1 | 2 | wt | N | R | R | ND | P | N | N | Ne | Porphyromonas denticanis |
| B0385 | UF1E | C | DSHA | 2 | F | ULPM3 | 1 | 1 | 2 | lt brn | Y | R | s | s | P | N | N | Ne | Campylobacter sputorum |
| B0389 | UF2C | C | DSHA | 2 | F | ULPM3 | 0.5 | 1 | 1 | brn | N | s | ? | R | N | N | N | P | Porphyromonas circumdentaria |
| B0390 | UF2D | C | DSHA | 2 | F | ULPM3 | 0.5 | 1 | 1 | dk brn | Y | ND | ND | ND | N | N | N | P | Staphylococcus warneri partia |
| B0391 | UF2E | C | DSHA | 2 | F | ULPM3 | 0.5 | 1 | 1 | dk brn | Y | ND | ND | ND | N | N | N | P | Salmonella bongori |
| B0392 | UF2F | C | DSHA | 2 | F | ULPM3 | 0.5 | 1 | 1 | brn | N | ND | ND | ND | N | N | N | P | Clostridium sp. |
| B0394 | UF3B | C | DSHA | 2 | F | ULPM3 | 1 | 1 | 1 | lt brn | N | R | s | R | P | N | N | P | Porphyromonas salivosa |
| B0398 | UF3F | C | DSHA | 2 | F | ULPM3 | 1 | 1 | 1 | dk brn | Y | R | s | s | P | Y | N | Ne | Porphyromonas gulae |
| B0401 | UF4C | C | DSHA | 2 | F | ULPM3 | 1 | 1 | 1 | yel | N | R | R | R | N | Y | N | Ne | Porphyromonas denticanis |
| B0402 | UF4D | C | DSHA | 2 | F | URPM3 | 1 | 1 | 1 | dk brn | Y | R | R | R | P | N | N | P | Porphyromonas gulae |
| B0403 | UF4E | C | DSHA | 2 | F | URPM3 | 1 | 1 | 1 | brn | N | s | s | s | P | N | N | P | Porphyromonas gulae |
| B0411 | UF7A | C | DSHA | 5 | F | ULPM3 | 1 | 2 | 2 | dk brn | Y | s | s | s | P | Y | Y | P | Globicatella sp. |
| B0412 | UF7B | C | DSHA | 5 | F | ULPM3 | 1 | 2 | 2 | lt brn | N | R | s | R | N | Y | N | P | Porphyromonas salivosa |
| B0414 | UF7D | C | DSHA | 5 | F | ULPM3 | 1 | 2 | 2 | grybrn | N | s | s | R | P | Y | N | Ne | Porphyromonas denticanis |
| B0416 | UF7F | C | DSHA | 5 | F | ULPM3 | 2 | 2 | 2 | brnfan | N | ND | ND | ND | P | Y | N | Ne | Marine snow assoc. bacterium |
| B0417 | UF9A | C | DSHA | ND | F | ULPM3 | 2 | 2 | 2 | yel | N | s | R | R | P | N | N | P | Porphyromonas salivosa |
| B0418 | UF9B | C | DSHA | ND | F | ULPM3 | 2 | 2 | 2 | grybrn | N | R | R | R | P | N | N | Ne | Porphyromonas denticanis |

TABLE 2-continued

Canine and feline BPAB isolate characterization

| Bact. Log # | Source | Dog/Cat | Breed | Age | sex | Tooth sampled | Pocket Depth | Periodontal index | Gingivitis index | Pigment | Hemolysis | Kan | Vanc | Col | Indole | Lipase | Lecith. | Catalase | Genus/species by 16S rRNA sequence |
|---|---|---|---|---|---|---|---|---|---|---|---|---|---|---|---|---|---|---|---|
| B0421 | UF9E | C | DSHA | ND | F | ULPM3 | 2 | 2 | 2 | grybrn | N | R | R | R | P | N | N | Ne | *Porphyromonas denticanis* |
| B0422 | UF9F | C | DSHA | ND | F | ULPM3 | 2 | 2 | 2 | blk | N | R | R | R | P | N | N | Ne | *Porphyromonas denticanis* |
| B0423 | UF10A | C | DSHA | ND | F | ULPM3 | 2 | 2 | 2 | blk | Y | S | S | ND | N | Y | N | P | *Porphyromonas gulae* |
| B0427 | UF10E | C | DSHA | ND | F | ULPM3 | 2 | 2 | 2 | blk | N | ND | ND | ND | P | ND | N | P | *Porphyromonas gulae* |
| B0428 | UF10F | C | DSHA | ND | F | ULPM3 | 2 | 2 | 2 | blk | N | R | R | R | P | Y | N | P | *Porphyromonas gulae* |
| B0437 | UCD4C | D | MSHZ | 4 | F | LLM1 | 2 | 2 | 2 | brnfan | Y | S | S | S | P | N | N | Ne | *Veillonella* sp. oral clone X042 |
| B0438 | UCD4D | D | MSHZ | 4 | F | LLM1 | 2 | 2 | 2 | yel | N | ND | ND | ND | ND | N | N | ND | *Prevotella oulora* |
| B0439 | UCD4E | D | MSHZ | 4 | F | LLM1 | 2 | 2 | 2 | lt brn | N | ND | ND | ND | ND | N | N | ND | *Lactobacillus rimae* |
| B0440 | UCD4F | D | MSHZ | 4 | F | LLM1 | 2 | 2 | 2 | lt brn | Y | S | S | S | N | N | N | Ne | *Streptococcus suis* |
| B0442 | UCD5B | D | BOXE | 12 | F | URI1 | 3 | 2 | 2 | ND | ND | ND | ND | ND | P | ND | ND | Ne | *Capnocytophaga* sp. |
| B0446 | UCD6A | C | DSHA | 2 | M | LRM1 | ND | 2 | 2 | ltbrn | N | R | R | R | P | N | N | P | *Porphyromonas circumdentaria* |
| B0447 | UCD6B | C | DSHA | 2 | M | LRM1 | ND | 2 | 2 | blk | N | R | S | S | N | N | N | P | *Porphyromonas circumdentaria* |
| B0448 | UCD6C | C | DSHA | 2 | M | LRM1 | ND | 2 | 2 | blk | N | R | S | R | P | N | N | P | *Porphyromonas circumdentaria* |
| B0449 | UCD6D | C | DSHA | 2 | M | LRM1 | ND | 2 | 2 | brn | N | R | S | ? | P | N | N | P | *Porphyromonas circumdentaria* |
| B0450 | UCD6E | C | DSHA | 2 | M | LRM1 | ND | 2 | 2 | brn | N | R | S | R | P | N | N | P | *Porphyromonas circumdentaria* |
| B0452 | UCD6G | C | DSHA | 2 | M | LRM1 | ND | 2 | 2 | blk | N | R | S | S | N | N | N | P | *Porphyromonas circumdentaria* |
| B0453 | UCD6H | C | DSHA | 2 | M | LRM1 | ND | 2 | 2 | blk | N | R | S | R | P | N | N | P | *Porphyromonas circumdentaria* |
| B0456 | UCD7B | D | POOD | 8 | F | URCAN | ND | ND | ND | blk | N | R | R | R | P | N | N | Ne | *Porphyromonas denticanis* |
| B0457 | UCD7C | D | POOD | 8 | F | URCAN | ND | ND | ND | brn | N | R | S | S | P | N | N | Ne | *Porphyromonas denticanis* |
| B0458 | UCD7D | D | POOD | 8 | F | URCAN | ND | ND | ND | yel | N | R | S | R | P | N | N | Ne | *Bacteroides acidofaciens* |
| B0463 | UCD8C | D | DLHA | 6 | M | LLP4 | ND | 1 | ND | brn | N | S | S | S | P | N | Y | P | *Peptostreptococcus* sp. |
| B0473 | UCD10A | D | WHWT | 10 | M | URP4 | 3 | 2 | 2 | wht | N | R | R | R | P | ND | ND | Ne | *Bacteroides acidofaciens* |
| B0474 | UCD10B | D | WHWT | 10 | M | URP4 | 3 | 2 | 2 | wyel | N | R | ND | s | P | ND | ND | Ne | *Bacteroides acidofaciens* |
| B0476 | UCD10D | D | WHWT | 10 | M | URP4 | 3 | 2 | 2 | wht | N | R | R | R | P | ND | ND | Ne | *Bacteroides acidofaciens* |
| B0477 | UCD10E | D | WHWT | 10 | M | URP4 | 3 | 2 | 2 | brn | Y | R | R | R | P | ND | ND | P | *Porphyromonas salivosa* |
| B0478 | UCD10F | D | WHWT | 10 | M | URP4 | 3 | 2 | 2 | brn | Y | R | R | R | P | ND | ND | Ne | *Porphyromonas salivosa* |

Abbreviations:
D, Dog;
C, Cat;
NA, Not applicable;
ND, Not determined;
M, Male;
F, Female;
Y, Yes;
N, No;
P, Positive;
Ne, Negative The isolates were typed based on their 16S rRNA DNA sequence. Individual, well-isolated colonies were utilized as template for polymerase chain reactions (PCR) amplification of the 16S rRNA region using primers D0056 and D0057 (Seq. ID No. 1 and Seq. ID No. 2; Table 1) in triplicate. The PCR was carried out in 50 μl reaction volumes containing 1× PCR buffer (Life Technologies; Rockville, Md.), 1.0 mM MgCl$_2$, 1.25 μM each primer, 300 μM each deoxy-NTP, and 2.5 U Platinum Pfx DNA Polymerase (Life Technologies). The following PCR cycle conditions were utilized: a two minute denaturation step at 94° C.; 30 cycles of denaturation at 94° C. for 40 seconds, annealing at 60° C. for 40 seconds, and extension at 72° C. for one minute; a final extension step at 72° C. for two minutes; and a final cooling step to 4° C. A GeneAmp 9700 thermocycler (Perkin Elmer Applied Biosystems; Foster City, Calif.) was utilized for all PCR amplifications.

The resulting PCR products were purified using the PCR preps kits (Promega Corp.; Madison, Wis.) and pooled by isolate. The purified PCR products were then desalted by drop analysis against 25 ml sterile water using a 0.025 μm nitrocellulose filter (Millipore Corp.; Bedford, Mass.). The purified, desalted PCR products were subjected to DNA sequence analysis using the DyeDeoxy termination reaction on an ABI automated DNA sequencer (University of Texas Genetics Core Facility, Houston, Tex. and Lark Technologies Inc., Houston, Tex.). Synthetic oligonucleotide primers D0056, D0057, PFZ175-AP1, PFZ175-AP2, and PFZ175-AP3 (Seq. ID No. 1-5, respectively; Table 1) were used to obtain double stranded DNA sequence. The resulting DNA sequences were used to search publicly available DNA databases using a BLAST-N program publicly available from The National Center for Biotechnology Information, USA.

The bacterial isolates were typed based on the closest match identified by database searches. The B106 isolates did not have a precise match. The nearest match was with an uncultured bacterial type that was identified by random PCR of human periodontal pocket material. This isolate was referred to as *Porphyromonas denticanis* strain B106. A complete listing of all the isolates and their respective characteristics is located in Table 2. The top nine most frequently isolated strains are exemplified by the following isolates: *P. gulae* B43 (dog sample Sandwich 4), *P. cansulci* B46 (dog sample VHUP 1B), *P. circumdentaria* B52 (cat sample VHUP 2A), *P. gulae* B69 (cat sample VHUP 3A), *P. circumdentaria* B97 (dog sample TH 1bC), *P. cangingivalis* B98 (dog sample TH 1aC), *P. salivosa* B104 (dog sample TH 1bC), *P. denticanis* B106 (dog sample TH 1bE), and *P. endodontalis* B114 (dog sample TH 2bA).

The distribution of isolates is shown in Table 3.

TABLE 3

Summary of the number of dogs and cats identified to harbor indicated bacterial species.

| Isolate | # dog isolates | # dogs | % positive dogs | # cat isolates | # cats | % positive |
|---|---|---|---|---|---|---|
| *Porphyromonas gulae* | 27 | 16 | 31 | 8 | 6 | 38 |
| *Porphyromonas salivosa* (*macacae*) | 27 | 17 | 33 | 3 | 2 | 13 |
| *Porphyromonas denticanis* | 24 | 15 | 29 | 0 | 0 | 0 |
| *Porphyromonas cansulci* | 12 | 8 | 15 | 0 | 0 | 0 |
| *Porphyromonas endodontalis* | 11 | 8 | 15 | 0 | 0 | 0 |
| *Porphyromonas circumdendaria* | 10 | 8 | 15 | 15 | 4 | 25 |
| *Bacteroides acidofaciens* | 10 | 5 | 10 | 0 | 0 | 0 |
| *Bacteroides forsythus* | 4 | 3 | 6 | 1 | 1 | 6 |
| *Porphyromonas cangingivalis* | 3 | 2 | 4 | 0 | 0 | 0 |
| *Bacteroides levii* | 3 | 2 | 4 | 0 | 0 | 0 |
| *Eubacterium brachy* ATCC33089 | 3 | 3 | 6 | 0 | 0 | 0 |
| *Peptostreptococcus* sp. D1 | 3 | 4 | 8 | 1 | 1 | 6 |
| Unidentified eubacterium | 3 | 2 | 4 | 0 | 0 | 0 |
| *Porphyromonas canoris* | 2 | 2 | 4 | 0 | 0 | 0 |
| *Campylobacterium sputorum* | 2 | 2 | 4 | 1 | 1 | 6 |
| *Porphyromonas gingivalis* | 1 | 1 | 2 | 0 | 0 | 0 |
| *Bacteroides fragilis* | 1 | 1 | 2 | 0 | 0 | 0 |
| Uncultured bacterium SHA-54 | 1 | 1 | 2 | 0 | 0 | 0 |
| Uncultured bacterium SHA-219 | 1 | 1 | 2 | 0 | 0 | 0 |
| *Pasteurella canis* | 1 | 1 | 2 | 0 | 0 | 0 |
| *Streptococcus bovis* JB1 | 1 | 1 | 2 | 0 | 0 | 0 |
| *Enterococcus gallinarum* | 1 | 1 | 2 | 0 | 0 | 0 |
| *Fusobacterium alocis* | 1 | 1 | 2 | 0 | 0 | 0 |
| *Klebsiella oxytoca* | 1 | 1 | 2 | 0 | 0 | 0 |
| Unidentified rumen bacterium | 1 | 1 | 2 | 0 | 0 | 0 |
| Uncultured bacterium AF132259 | 0 | 0 | 0 | 6 | 3 | 19 |
| *Prevotella oulora* | 0 | 1 | 2 | 0 | 0 | 0 |
| *Tessatacoccus bendigoniensis* | 0 | 0 | 0 | 1 | 1 | 6 |
| *Staphyloccus warneri* | 0 | 0 | 0 | 1 | 1 | 6 |
| *Salmonella bongori* | 0 | 0 | 0 | 1 | 1 | 6 |
| *Clostridium* sp. | 0 | 0 | 0 | 1 | 1 | 6 |

TABLE 3-continued

Summary of the number of dogs and cats identified to harbor indicated bacterial species.

| Isolate | # dog isolates | # dogs | % positive dogs | # cat isolates | # cats | % positive |
|---|---|---|---|---|---|---|
| *Globicatella* sp. | 0 | 0 | 0 | 1 | 1 | 6 |
| Marine snow associated bacterium | 0 | 0 | 0 | 1 | 1 | 6 |
| *Veillonella* sp. oral clone X042 | 0 | 1 | 2 | 0 | 0 | 0 |
| *Lactobacillus rimae* | 0 | 1 | 2 | 0 | 0 | 0 |
| *Streptococcus suis* | 0 | 1 | 2 | 0 | 0 | 0 |
| *Capnocytophaga* sp. | 0 | 1 | 2 | 0 | 0 | 0 |

The isolates listed above represent those species that were most frequently identified and present in the highest percentages of dogs or cats.

The following companion animal periodontal isolates were deposited with the American Type Culture Collection (ATCC), 10801 University Blvd., Manassas, Va., 20110, USA, on Aug. 9, 2001: *P. gulae* B43 (PTA-3618), *P. cansulci* B46 (PTA-3619), *P. circumdentaria* B52 (PTA-3620), *P. gulae* B69 (PTA-3621), *P. circumdentaria* B97 (PTA-3622), *P. cangingivalis* B98 (PTA-3623), *P. salivosa* B104 (PTA-3624), *P. denticanis* B106 (PTA-3625), and *P. endodontalis* B114 (PTA-3626).

Culture Conditions for *Porphyromonas* sp

Since the standard growth media for *Porphyromonas* sp. (Brain Heart Infusion (BHI) and Chopped Meat Carbohydrate (CMC) media) contain animal product, which are not amenable for vaccine production, a growth medium that does not contain these ingredients was sought. Various media compositions, with and without the addition of hemin and vitamin K, were tested for their ability to support growth equivalent to that of growth of BHI or CMC. Both the PYG-complete medium and ME-complete medium supported the growth of *P. gulae* B43 (PTA-3618) to a level equivalent to that of BHI (FIG. 1). The PYG-complete medium was chosen as the *P. gulae* B43 (PTA-3618) growth medium due to its ability to yield high density cultures during fermentation. This medium contains the following ingredients: 3% phytone (Becton Dickinson; Cockeysville, Md.), 0.3% yeast extract (Becton Dickinson), 0.3% glucose (Sigma Corp.; St. Louis, Mo.), 0.05% sodium thioglycollate (Becton Dickinson), 0.5% sodium chloride (Sigma Corp.), 5 µg/ml hemin (Sigma Corp.) (added after autoclaving), 0.5 µg/ml menadione (Sigma Corp.) (added after autoclaving), and 0.2% sodium bicarbonate (Sigma Corp.), pH 7.0.

*P. gulae* B43 (PTA-3618) was routinely cultivated on Brucella blood agar plates (Anaerobe Systems) or in complete PYG medium or BHI at 37° C. in a Bactron IV anaerobic chamber (Shel Labs; Cornelius, Oreg.) under 90% $N_2$, 5% $CO_2$ for three to five days (plates) or 24 to 48 hours (liquid cultures). For whole cell bacterin preparation, *P. gulae* B43 (PTA-3618) was cultivated in a BioFlo 3000 Bioreactor using 5 liters of PYG complete medium. The culture medium in the vessel was rendered anaerobic by sparging with 95-99.5% $N_2$ and 0.5-5% $CO_2$ immediately after autoclaving. The reduced culture medium was seeded with 0.02% of *P. gulae* B43 (PTA-3618) stock and cultivated at 37° C. with an agitation rate of 100 rpm and the pH maintained at 7.0 by the automatic addition of NaOH. During cultivation, the vessel was periodically sparged with both $N_2$ and $CO_2$. The bacterial cells were collected after 36 to 48 hours at an $OD_{600}$ of 2.0 to 3.5 while cells were still undergoing logarithmic growth.

Pathogenicity Testing of Clinical Isolates

The nine isolates (*P. gulae* B43, *P. cansulci* B46, *P. circumdentaria* B52, *P. gulae* B69, *P. circumdentaria* B97, *P. cangingivalis* B98, *P. salivosa* B104, *P. denticanis* B106, and *P. endodontalis* B114) were tested for their pathogenicity in the mouse periodontal bone loss model. Three-week-old, age-matched male Balb/c CyJ mice (Jackson Laboratories; Bar Harbor, Me.) with estimated weights of 14-15 grams were utilized for this study. The animals were housed in positive pressure, barrier cage units. Food pellets, standard for the species, and water were provided ad libitum throughout the experiment. The bedding utilized was granular Bed O'Cobbs to minimize impaction in the gingival tissues. Following receipt, all animals were acclimatized for five to seven days. To reduce competing oral flora, animals were placed on a mixture of sulfamathoxazole and trimethoprim (10 ml drinking water; approximately 2 mg and 0.4 mg/ml, respectively) for ten days followed by a five-day washout period. Serum samples were taken from each mouse tail vein bleed. The animals were infected with 0.5 ml suspension of approximately $1 \times 10^{10}$ cfu/ml of the appropriate bacterial strain in 1% carboxymethylcellulose by gavage. Additional drops were placed in the oral cavity. This infection was repeated two more times for a total of three times (Monday, Wednesday, and Friday).

Day 1 of the experiment was defined as the Tuesday following the first infection. All animals were sacrificed on Day 2. Post-infection serum was collected, as were microbial samples. The jaws of each mouse were defleshed, stained, and scored for horizontal bone loss microscopically. The scoring was repeated three times to reduce operator error. The average bone loss is expressed as the average bone loss/site/jaw in mm. Statistical analysis of the resulting data was done with Systat (version 9), SigmaStat (version 2), and SigmaPlot (version 2000) available from SPSS Science Inc. (Chicago, Ill.). Table 4 shows the numerical results for the top nine isolates.

TABLE 4

Summary of the mouse periodontal disease pathogenicity trial.

| Isolate | Number of mice | Source of bacteria | Mean Bone Loss (mm) | Std. Deviation | SEM |
|---|---|---|---|---|---|
| Sham | 32 | N/A | 0.0843 | 0.0118 | 0.00211 |
| P. gingivalis 53977 | 16 | Human | 0.106 | 0.0139 | 0.00347 |
| P. gingivalis W50 | 16 | Human | 0.0948 | 0.0116 | 0.0029 |
| P. gingivalis B40 A | 16 | Dog | 0.106 | 0.0138 | 0.00357 |
| P. gingivalis B40 B | 16 | Dog | 0.115 | 0.0114 | 0.00284 |
| P. gulae B43 | 16 | Dog | 0.112 | 0.0163 | 0.00407 |
| P. cansulci B46 | 16 | Dog | 0.101 | 0.014 | 0.00362 |
| P. circumdentaria B52 | 16 | Cat | 0.0924 | 0.00836 | 0.00209 |
| P. gulae B69 | 16 | Cat | 0.114 | 0.0129 | 0.00322 |
| P. circumdentaria B97 | 16 | Dog | 0.0855 | 0.0143 | 0.00368 |
| P. cangingivalis B98 | 16 | Dog | 0.111 | 0.0136 | 0.0034 |
| P. salivosa B104 | 16 | Dog | 0.102 | 0.0107 | 0.00286 |
| P. denticanis B106 | 16 | Dog | 0.124 | 0.0167 | 0.00417 |
| P. endodontalis B114 | 16 | Dog | 0.0994 | 0.0223 | 0.00557 |

Each of these yielded statistically significant bone loss in this model.

Figure 2:
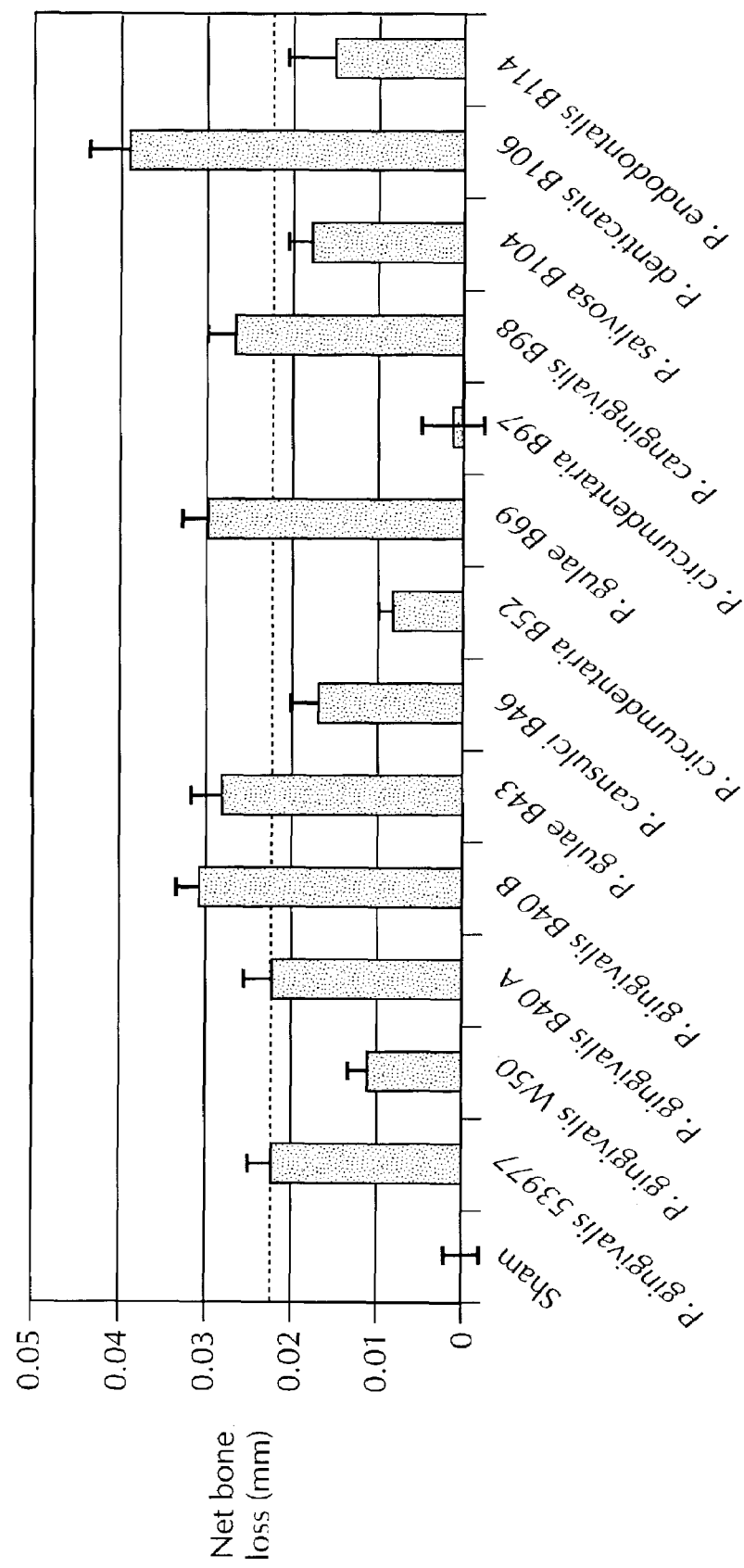
FIG. 2 is a graph showing mean bone loss in mice resulting from super infection with the indicated *Porphyromonas* sp.

FIG. 2 graphically shows the net bone loss. The mean alveolar bone levels (cementoenamel junction—alveolar bone crest) were obtained at 14 maxillary sites in mm, and the mean value for each jaw was determined. For each experimental group, the mean values for each jaw were summed and the group mean derived by dividing by the total number of animals in that group.

Figure 3:
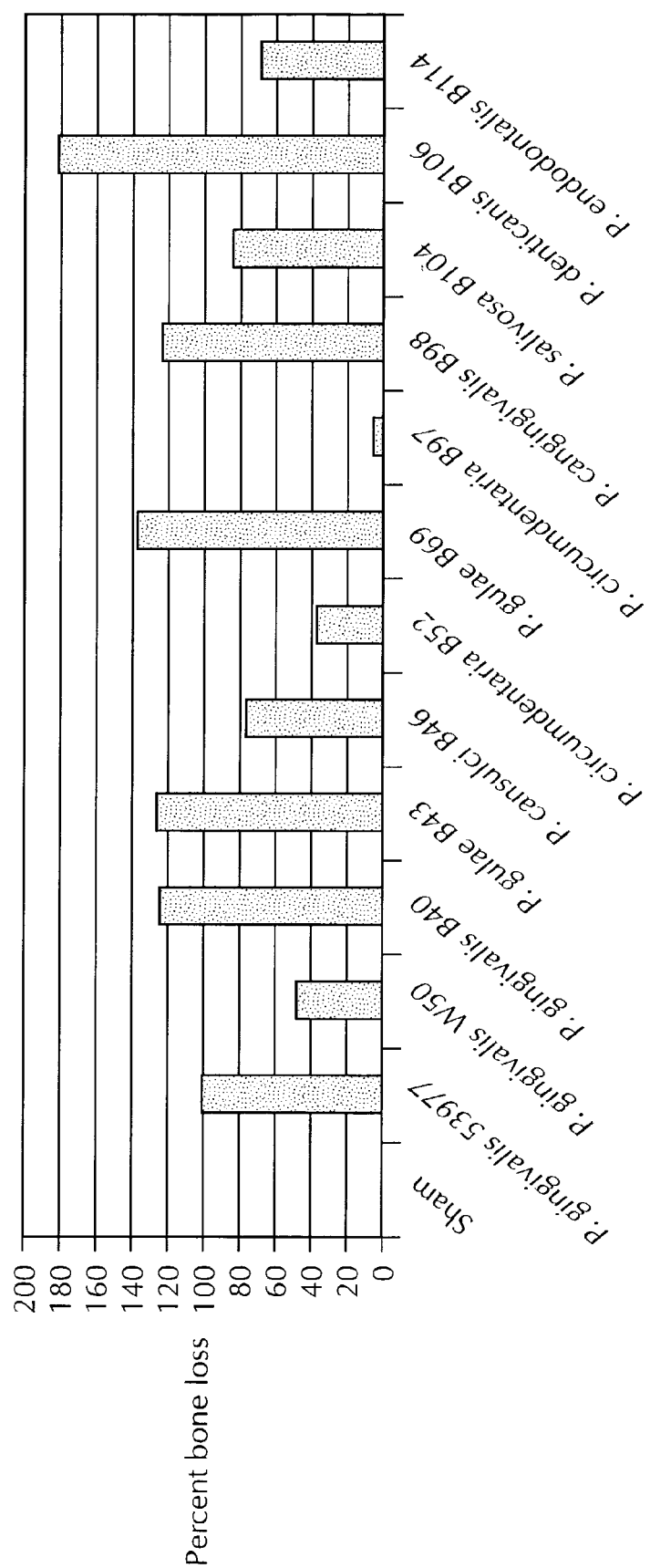
FIG. 3 is a graph showing percent bone loss in mice resulting from super infection with the indicated *Porphyromonas* sp.

FIG. 3 graphically shows the comparison of net bone loss. The mean alveolar bone levels (cementoenamel junctions—alveolar bone crest) were obtained at 14 maxillary sites in mm, and the mean value for each jaw was determined. For each experimental group, the mean values for each jaw were summed and the group mean derived by dividing by the total number of animals in that group. The net bone loss was determined by subtracting the sham infected mean values from each experimental groups. The data is presented as a percentage of the positive control group (P. gingivalis 53977) which is set at 100%. P. gingivalis W50 is a poorly fimbrinated strain that has reduced virulence in this animal model.

These data indicate that the following clinical isolates are capable of producing high levels of bone loss in the mouse model of periodontal disease: P. gulae B43 (PTA-3618), P. gulae B69 (PTA-3621), P. cangingivalis B98 (PTA-3623) and P. denticanis B106 (PTA-3625). The following clinical isolates yielded moderate bone loss in the mouse periodontal model: P. cansulci B46 (PTA-3619), P. salivosa B104 (PTA-3624), and P. endodontalis B114 (PTA-3626). The following clinical isolates yielded minimal bone loss in the mouse periodontal model: P. circumdentaria B52 (PTA-3620) and P. circumdentaria B97 (PTA-3622). While varying amounts of bone loss were observed between the clinical isolates, it should be noted that in each case, the amount of bone loss observed was well above what was observed in the sham infected mice. Based on these data, it can be concluded that each of the top nine clinical isolates is capable of causing periodontal disease either alone or in concert with other bacteria.

Preparation of Bacterial Cells and Genomic DNA

Porphyromonas spp. were anaerobically cultivated in BHI or complete PYG at 37° C. for 48 hours. Cells from a 1-3 ml culture were pelleted by centrifugation, washed once in an equal volume of anaerobic PBS, re-centrifuged, and re-suspended in 1/10 volume anaerobic PBS.

Genomic DNA was purified from 5 ml cultures of Porphyromonas spp. that were anaerobically cultivated in BHI or complete PYG at 37° C. for 48 hours. The Wizard Genomic DNA Extraction kit (Promega Corp.) was utilized for all genomic DNA preparations.

Cloning of the Fimbrial Gene from Clinical Isolates

The fimA gene was PCR amplified from genomic DNA isolated from the top ten clinical isolates using combinations of the following PCR primers D0067 (forward; Seq. ID No. 6), D0078 (forward; Seq. ID No. 8), D0097 (forward; Seq. ID No. 9), D0068 (reverse; Seq. ID No. 7) and D0098 (reverse; Seq. ID No. 10). The PCR was carried out in 50 ul reaction volumes containing 1× PCR buffer (Life Technologies), 1.0 mM $MgCl_2$, 1.25 µM each primer, 300 M each deoxy-NTP, and 2.5 U Platinum Pfx DNA Polymerase (Life Technologies). The following PCR cycle conditions were utilized: a two minute denaturation step at 94° C.; 30 cycles of denaturation at 94° C. for 40 seconds, annealing at 60° C. for 40 seconds, and extension at 72° C. for 1.5 minutes; a final extension step at 72° C. for five minutes; and a final cooling step to 4° C. A GeneAmp 9700 thermocycler (Perkin Elmer Applied Biosystems; Foster City, Calif.) was utilized for all PCR amplifications. The amplified products were visualized on a 1.2% E-gel (Invitrogen; Carlsbad, Calif.).

The PCR products were A-tailed using 10 units of KlenTaq polymerase (Ab Peptides, Inc.; St. Louis, Mo.) for five minutes at 72° C. The resultant products were immediately T-tail cloned into the pCR2.1-TOPO vector (Invitrogen) using the manufacturer's protocol and transformed into E. coli Top10F' (Novagen; Madison, Wis.). Transformants harboring recombinant plasmids with the correct insert DNA were identified by a combination of colony PCR, restriction enzyme digestion, and DNA sequence analysis using DyeDeoxy termination reactions on an ABI automated DNA sequence (Lark Technologies, Inc.). Synthetic oligonucleotide primers (Seq. ID No. 6, 7, 8, 11-42) were used to obtain double stranded DNA sequence.

Cloning of the P. gulae B43 FimA Gene into Expression Plasmids

For the purpose of high-level protein expression, the P. gulae B43 (PTA-3618) fimA gene was cloned into the pBAD/HisA expression vector (Invitrogen). Genomic DNA was purified from a 5 ml culture of *P. gulae* B43 in BHI incubated at 37° C. for two days anaerobically using the genomic DNA extraction kit (Promega Corp.). The fimA gene was PCR amplified using primers D0097 and D0098 (Seq. ID No. 9 and Seq. ID No. 10) in triplicate. The PCR was carried out in 50 ul reaction volumes containing 1× PCR buffer (Life Technologies), 50 ng *P. gulae* B43 genomic DNA, 1.0 mM MgCL$_2$, 1.25 µM each primer, 300 µM each deoxy-NTP, and 2.5 U Platinum Pfx DNA Polymerase (Life Technologies, USA).

The following PCR cycle conditions were utilized: a two minute denaturation step at 94° C.; five cycles of denaturation at 94° C. for 40 seconds, annealing at 58° C. for 40 seconds, and extension at 72° C. for 1.5 minutes; 30 cycles of denaturation at 94° C. for 40 seconds, annealing at 65° C. for 40 seconds, and extension at 72° C. for 1.5 minutes; a final extension step at 72° C. for five minutes; and a final cooling step to 4° C. A GeneAmp 9700 thermocycler (Perkin Elmer Applied Biosystems) was utilized for all PCR amplifications. The PCR products were purified using PCR prep kits (Promega Corp.). The purified PCR products and pBAD/HisA were double digested with HindIII and XhoI for three hours at 37° C. Half way through the digestion, five units of shrimp alkaline phosphatase (SAP) (Amersham Pharmacia Biotech, Inc.: Piscataway, N.J.) were added to the vector digestion. The digested DNA's were purified using the DNA Clean-Up kit (Promega Corp.). The purified HindIII/XhoI digested PCR products were ligated into HindIII/XhoI digested, SAP treated pBAD/HisA with the T4 DNA Ligase enzyme (Life Technologies) in the presence of 1×T4 DNA ligase buffer at 16° C. for 18 hours. A portion of the resulting ligation mixture was transformed into competent *E. coli* Top10F' cells (Novagen). A recombinant plasmid, pBAD:B43fimA4, was found to contain the fimA gene in the correct orientation. The resulting recombinant FimA contains a terminal, vector-encoded sequence.

(MGGSHHHHHHGMASMTGGQMGRDLYD-DDDKDRWGSELEICSQYHMGI, SEQ ID NO: 135), followed by the mature portion of FimA beginning at asparagine-20. This plasmid was transformed into competent *E. coli* BL21 cells (Novagen) for further protein expression analysis.

Expression and Purification of the Recombinant FimA Protein

Figure 4B:
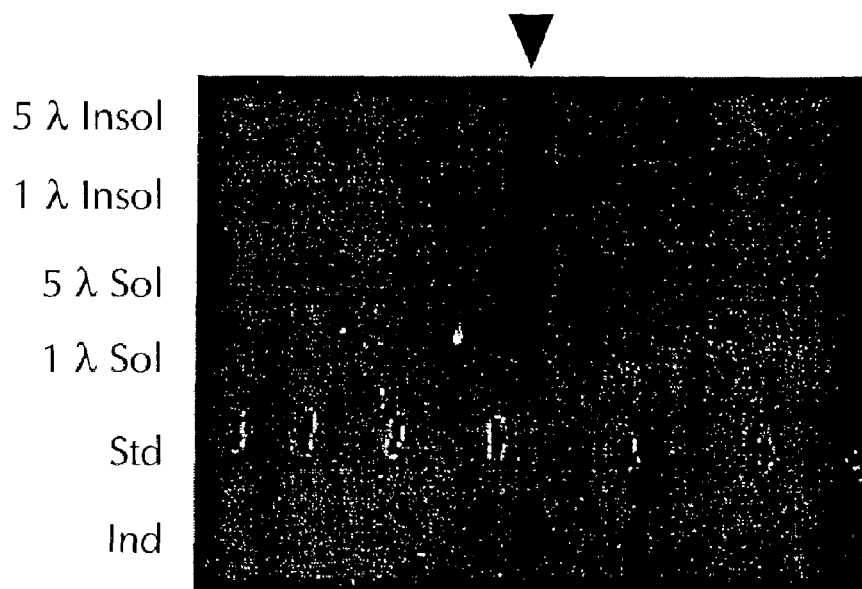
FIGS. 4A and B are photographs showing in FIG. 4A, an SDS PAGE, and in FIG. 4B a Western blot analysis, using the anti-Xpress™ epitope serum (Invitrogen), of recombinant *P. gulae* B43 FimA expressed in *E. coli* BL21 from pBAD-HisA.
Figure 4A:
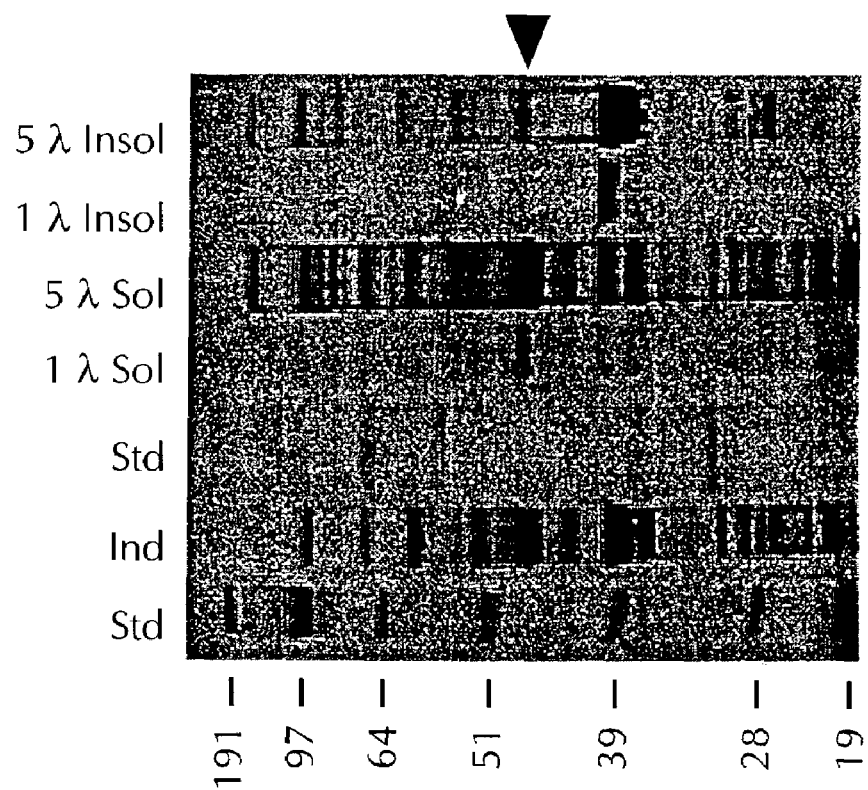

A frozen working stock of the *E. coli* BL21/pBAD:B43fimA4 was thawed, seeded at a 1:5000 dilution into Luria broth containing 100 µg/ml ampicillin (1% tryptone, 0.5% yeast extract, 0.5% NaCl), and grown in a 5 liter working volume BioFlo 3000 Bioreactor (New Brunswick Scientific; Edison, N.J.) at 37° C. with a 100 rpm agitation rate until A$_{625}$ was 2.5-3.5. L-arabinose was then added to the culture at a final concentration of 0.1% to induce FimA expression. The culture was incubated for an additional three hours. Expression of the recombinant FimA was detected by SDS-PAGE and Western blot analysis using anti-Express serum (Invitrogen) (FIG. 4). The recombinant FimA protein had a predicted molecular mass of 45 kDa.

Wet cells of the *E. coli* BL21 transformant expressing recombinant FimA from the 5 liter fermentation were harvested by centrifugation and re-suspended in phosphate-buffered saline. The cells were mechanically lysed. Following centrifugation, the pellet was discarded. The supernatant was passed over a Ni$^{2+}$-affinity column, and eluted off using an imidazole gradient. Fractions containing the recombinant protein were pooled, dialyzed to remove the imidazole, and filter-sterilized using a 0.2 µm filter.

Cloning of the oprF Gene from Clinical Isolates

Based on sequences of the *P. gingivalis* strain W50 oprF homolog, gene PG32 (Genbank accession number AF175714), oligonucleotide primers D0086 (SEQ ID No. 43), D0087 (SEQ ID NO. 44), and KWK-Pg-03 (SEQ ID NO. 45) were designed and synthesized (Life Technologies). For PCR, primer D0086 (SEQ ID NO. 43) was used in conjunction with either D0087 (SEQ ID NO. 44) or KWK-Pg-03 (SEQ ID NO. 45) in 1× PC2 buffer (Ab Peptides), 200 µM each dNTP, 7.5 U KlenTaq1 (Ab Peptides) and 0.15 U cloned Pfu (Stratagene; La Jolla, Calif.) thermostable polymerases in a 50 µl final sample volume. Reactions were performed in triplicate using either a washed cell suspension or purified genomic DNA as template from *P. gulae* B43, *P. cansulci* B46, *P. circumdentaria* B52, *P. gulae* B69, *P. circumdentaria* B97, *P. cangingivalis* B98, *P. salivosa* B104, *P. denticanis* B106, and *P. endodontalis* B114. Amplification was carried out as follows: denaturation (94° C., 9 minutes); 30-40 cycles of denaturation (94° C., 30 seconds), annealing (55-60° C. 30 seconds), and polymerization (72° C., 1.5 minutes); followed by a final extension at 72° C. for seven minutes.

For polymerase chain amplification of the oprF homolog from *P. cangingivalis* B98, primer KWK-Ps-04b (SEQ ID No. 81) was used in conjunction with KWK-Ps-06b (SEQ ID No. 83). For amplification of the homolog from *P. salivosa* B104, primer KWK-Ps-04b (SEQ ID No. 81) was used with KWK-Ps-05b (SEQ ID No. 82). For amplification of the gene from *P. denticanis* B106, primer KWK-Ps-02 (SEQ ID No. 79) was used with KWK-Ps-03 (SEQ ID No. 80). Reactions were performed in triplicate using purified chromosomal DNA as template from strains *P. cangingivalis* B98, *P. salivosa* B104, and *P. denticanis* B106. Amplification was carried out as follows: denaturation (94° C., 9 minutes); 30-35 cycles of denaturation (94° C., 30 seconds), annealing (61-72° C., 30 seconds), and polymerization (72° C., 1.5 minutes); this was followed by a final extension at 72° C. for 7 minutes.

The PCR amplified gene products were visualized by separation on a 1.0% agarose gel (Sigma). The PCR products were purified using a QIAquick™ PCR Purification kit (Qiagen; Valancia, Calif.), and each set of triplicate samples pooled. These fragments were then sequenced directly in an attempt to avoid the introduction of sequence artifacts due to mutations that arise during PCR amplification and subsequent cloning steps. The pooled mixtures were then subjected to direct sequence analysis using DyeDeoxy termination reaction on an ABI automated DNA sequencer (Lark Technologies). Synthetic oligonucleotide primers (SEQ ID NO. 46-75) were used to sequence both DNA strands of the amplified products.

The nucleotide sequences encoding the OprF homolog from *P. gulae* B43, *P. cansulci* B46, *P. circumdentaria* B52, *P. gulae* B69, *P. circumdentaria* B97, *P. cangingivalis* B98, *P. salivosa* B104, *P. denticanis* B106, *P. cangingivalis* B98, *P. salivosa* B104, *P. denticanis* B106, and *P. endodontalis* B114 are depicted in SEQ ID NO. 111 to 119. Sequence corresponding the 5' and 3' primers used for PCR amplification of each gene was removed, as it may not represent the actual sequence of the gene in each of the respective strains. The ORFs encoded by SEQ ID NO.111 to 119 are shown in SEQ ID No. 120 to 128, respectively. For each of the encoded ORFs, the amino terminal sequence, even when that encoded by the 5' primer was excluded, still maintained characteristics of a prokaryotic signal sequence (von Heijne, 1985, J. Mol. Biol. 184:99-105; Nielsen, H., Engelbrecht, J., Brunak, S., and von Heijne, G., 1997 Protein Engineering, 10: 1-6). Each ORF was compared against existing nucleotide and protein databases using the Basis Local Align Search Tool (BLAST) programs (Altschul, S. F., Gish, W., Miller, W., Myers, E. W., Lipman, D. J., 1990, J. Mol. Biol. 215:403-410). The entry with which each shared the greatest homology was PG32 from *P. gingivalis*.

Cloning of the *P. gulae* B43 OprF Gene into Expression Plasmids

For the purpose of recombinant protein expression, the gene encoding OprF was cloned with the sequence encoding its signal peptide. OprF was amplified from *P. gulae* B43 using oligonucleotide primers KWK-Pg-06 (SEQ ID NO. 76) and KWK-Pg-03 (SEQ ID NO. 45). For polymerase chain amplification, duplicate 50 μl reactions were set up containing chromosomal DNA as template, 1× PC2 buffer, 200 μM each dNTP, 50 pMol each primer, 7.5 U KlenTaq1 and 0.15 cloned Pfu thermostable polymerase. Amplification was carried out as follows: denaturation (94° C., nine minutes); 30 cycles of denaturation (94° C., 30 sec), annealing (60° C., 30 sec), and polymerization (72° C., 1.5 min), followed by a final extension at 72° C. for 7 minutes. Following amplification, the samples were purified (QIAquick™ PCR Purification kit) and pooled. The purified PCR product was cloned directly into the TA cloning site of both pBAD-TOPO and pBAD/Thio-TOPO (Invitrogen). The ligand products were transformed into Max Efficiency *E. coli* DH5α cells. The predicted amino terminal sequence of the encoded protein expressed from pBAD-TOPO:OprF consists of the vector-encoded sequence MGSGSGDDDDKLALM (SEQ ID NO: 136) followed immediately by the sequence beginning at glutamine-13 of OprF (SEQ ID No. 120). A clone containing the appropriate plasmid was identified, and purified plasmid was isolated from a small-scale broth culture using a QIAprep Spin Miniprep kit (Qiagen). This plasmid was transformed into *E. coli* BL21 cells (Novagen), and a clone was identified that contained the appropriate plasmid.

The predicted amino terminal sequence of the encoded fusion protein expressed from pBAD/Thio-TOPO: oprF should consist of the thioredoxin protein and a 14 amino acid residue linker followed immediately by the sequence beginning at glutamine-13 of OprF (SEQ ID NO. 120). A clone containing the appropriate plasmid was identified, and purified plasmid was isolated from a small-scale broth culture using a QIAprep Spin Miniprep kit. This plasmid was transformed into *E. coli* BL21 cells, and a clone was identified that contained the appropriate plasmid.

The oprF gene lacking the sequence encoding the signal peptide was also cloned into two different λ expression plasmids. Both of these plasmids encode the temperature-sensitive λ repressor c/857, which inhibits expression from λ promoters at 30° C. At 42° C., the repressor is inactivated and expression from the λ promoter is enabled, yielding high-level transcription and translation. For cloning into these vectors, oprF was amplified from *P. gulae* B43 using oligonucleotide primers KWK-Pgu-14 (SEQ ID NO. 77) and KWK-Pgu-15 (SEQ ID NO. 78). For polymerase chain amplification, duplicate 50 μl reactions were set up containing washed *P. gulae* B43 cells as template, 1× PC2 buffer, 200 μM each dNTP, 50 pMol each primer, 7.5 U KlenTaq1 and 0.15 U cloned Pfu thermostable polymerases. Amplification was carried out as follows: denaturation (94° C., nine minutes); 45 cycles of denaturation (94° C., 30 seconds), annealing (55° C., 30 seconds), and polymerization (72° C., 1.5 minutes), followed by a final extension at 72° C. for seven minutes. Following amplification, the samples were pooled and digested with restriction enzymes, generating overhangs compatible with the plasmids which had also been linearized using the same enzymes. Following restriction digestion, the PCR fragment and plasmids were purified (QIAquick™ PCR Purification kit; Qiagen Corp.), ligated, and transformed into *E. coli* DH5α cells (Novagen). The predicted amino terminal consisted of the vector-encoded sequence MGTTTTTTSLHM (SEQ ID NO: 137) followed immediately by the sequence beginning at Glutamine-13 of OprF (SEQ ID NO. 120). The protein expressed from the second plasmid would consist only a vector-encoded Met followed by Glutamine-13 of OprF (SEQ ID NO: 120). Clones containing the appropriate plasmids were identified, and plasmids were isolated from small-scale broth cultures using QIAprep Spin Miniprep kits (Qiagen Corp.). These plasmids were transformed into *E. coli* BL21 cells, and separate clones were identified that contained the appropriate plasmids.

Expression and Purification of the Recombinant OprF Protein

Figure 5:
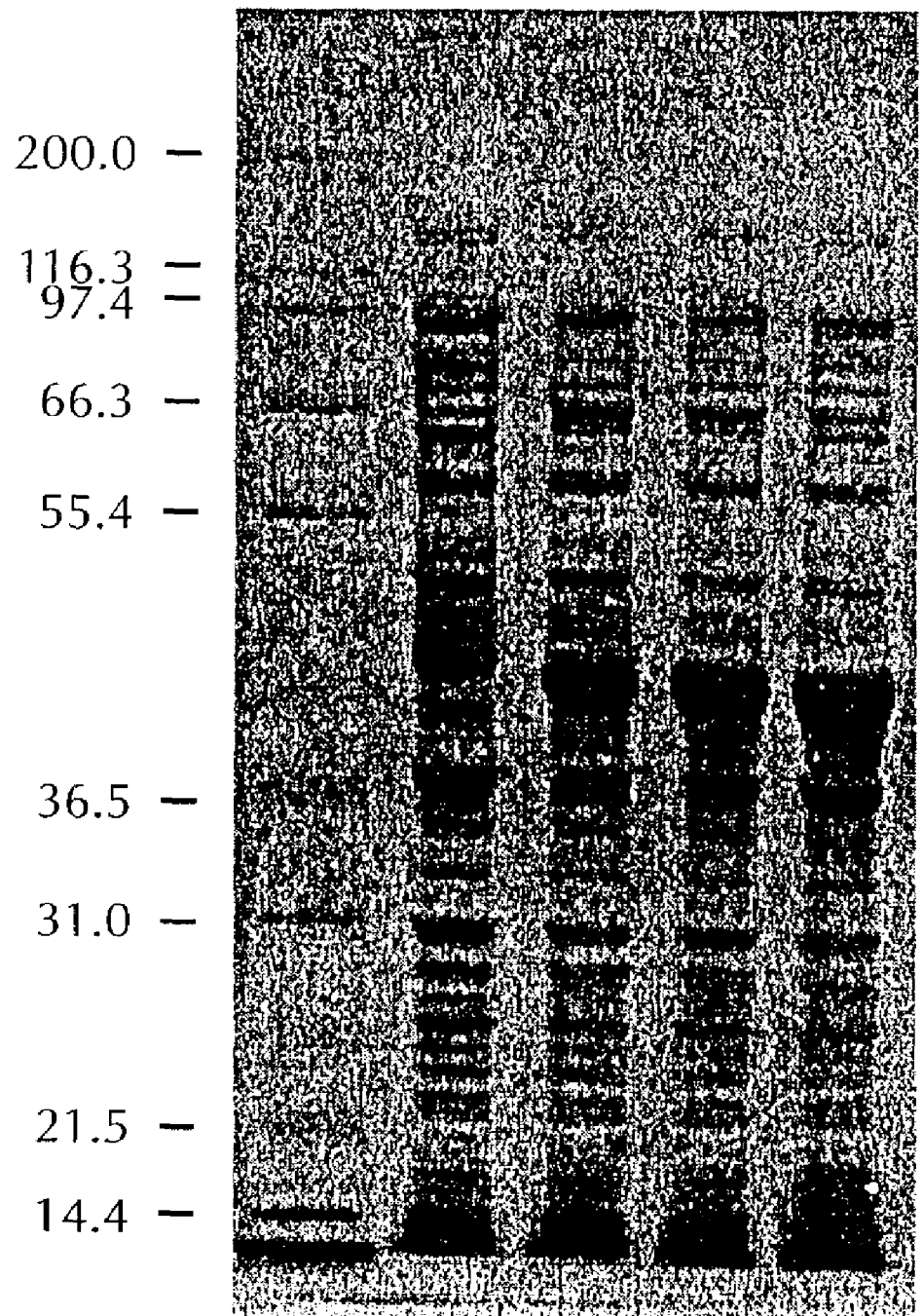
FIG. 5 is a photograph showing SDS-PAGE analysis of recombinant *P. gulae* B43 OprF expressed in *E. coli* BL21 cells from a lambda expression plasmid.

*E. coli* BL21 cells that express recombinant OprF (fused at its N-terminus to SEQ ID NO: 137) were utilized for expression studies. A frozen stock was thawed, seeded at a 1:5000 dilution into 2×YT medium containing 50 μg/ml kanamycin sulfate (1.6% tryptone, 1% yeast extract, 0.5 NaCL), and grown in a 5 liter working volume BioFlo 3000 Bioreactor (New Brunswick Scientific; Edison, N.J.) at 29° C. with a 100 rpm agitation rate until $A_{625}$ was 2.5-3.5. The cultures were then shifted to 42° C. to induce OprF expression. The culture was incubated for an additional 3 hours. Aliquots were removed at various time points, centrifuged, and re-suspended in reducing sample buffer. All samples were analyzed on a 10% NuPAGE gel (Invitrogen, USA) (FIG. 5).

Wet cells of the *E. coli* BL21 transformant expressing recombinant OprF from the 5 liter fermentation were harvested by centrifugation and re-suspended in phosphate-buffered saline. The cells were mechanically lysed. Following centrifugation, the pellet was discarded. The supernatant was passed over an ion exchange column, and eluted off using a NaCl gradient. Fractions containing the recombinant protein were pooled, dialyzed to remove the NaCl, and filter-sterilized using a 0.2 μm filter.

Whole Cell Bacterin Preparation

A 5 liter batch of *P. gulae* B43 was grown in a fermentor as described above and split into 1 liter portions. The cells in each 1 liter fraction ($4.4 \times 10^{12}$ total *P. gulae* B43 cells) were inactivated by the following treatments: exposure to 0.4% formalin for 24 hours at 23° C., exposure to 10 mM binary ethylene-imine (BEI) at pH 8.5 for 48 hours at 37° C., heating to 60° C. for 30 minutes on two consecutive days, and exposure to air for 48 hours. Following the BEI treatment, the BEI was inactivated by treatment with 50 mM sodium thiosulfate. The cells were collected by centrifugation. The resultant cells pellets were re-suspended in 220 ml PBS yielding a final concentration of $2 \times 10^{10}$ cells per ml. Seven ml of each of the inactivated cells was mixed with 7 ml of MPL+TDM adjuvant (Sigma Corp.) yielding a final concentration of $1.0 \times 10^{10}$ cells per ml.

Whole cell bacterin preparations of the other eight top clinical isolates (*P. cansulci* B46, *P. circumdentaria* B52, *P. gulae* B69, *P. circumdentaria* B97, *P. cangingivalis* B98, *P. salivosa* B104, *P. denticanis* B106, and *P. endodontalis* B114) or other pigmented anaerobic bacteria can be prepared in an identical fashion.

Homologous Vaccine Efficacy

In homologous vaccine efficacy studies, mice were immunized with two injections of 0.2 ml each of the above mentioned inactivated P. gulae B43 cells in MPL+TDM adjuvant three weeks apart. The mice were infected as previously described with P. gulae B43 two weeks following the booster immunization. Forty-two days following the infection, the mice were sacrificed and processed as previously described. Table 5 shows the numerical results of bone loss measurements. Vaccines containing either formalin-, heat-, or air-inactivated P. gulae B43 and MPL+TDM adjuvant reduced the bone loss induced by infection with P. gulae B43 by approximately 45%, 35%, and 75%, respectively. Based on these data, it can be concluded that the formalin-, air-, and heat-inactivated P. gulae B43 vaccines were efficacious in their ability to reduce bone loss induced in this superinfection model. Extrapolating this data into the clinical setting, these three vaccines would likely be efficacious in the prophylactic prevention of periodontal disease and may well prove efficacious in the therapeutic treatment of periodontal disease.

TABLE 5

Mouse homologous vaccine efficacy study results.

| Group | Vaccinogen | Challenge | Mean bone loss | Std. Dev. | SEM | Net bone loss | % bone loss (a) | % bone loss (b) |
|---|---|---|---|---|---|---|---|---|
| A | PBS with RIBI MPL + TDM adjuvant | None | 0.0686 | 0.00862 | 0.00216 | 0 | NA (c) | NA |
| B | PBS with RIBI MPL + TDM adjuvant | Pg 53977 | 0.112 | 0.0107 | 0.00266 | 0.0434 | 100 | NA |
| C | PBS with RIBI MPL + TDM adjuvant | Pg B43 | 0.093 | 0.0188 | 0.00471 | 0.0244 | NA | 100 |
| D | Formalin inactivated P. gingivalis 53977 with Freunds adjuvant | Pg 53977 | 0.098 | 0.0146 | 0.00364 | 0.0294 | 67.7 | NA |
| E | Formalin inactivated P. gingivalis 53977 with RIBI MPL + TDM adjuvant | Pg 53977 | 0.0932 | 0.0109 | 0.00271 | 0.0246 | 56.7 | NA |
| F | Formalin inactivated P. gulae B43 with RIBI MPL + TDM adjuvant | Pg B43 | 0.082 | 0.0128 | 0.00319 | 0.0134 | NA | 54.9 |
| G | BEI inactivated P. gulae B43 with RIBI MPL + TDM adjuvant | Pg B43 | 0.107 | 0.0151 | 0.0039 | 0.0384 | NA | 157.4 |
| H | Heat inactivated P. gulae B43 with RIBI MPL + TDM adjuvant | Pg B43 | 0.0845 | 0.0113 | 0.00281 | 0.0159 | NA | 65.2 |
| I | aeration inactivated P. gulae B43 with RIBI MPL + TDM adjuvant | Pg B43 | 0.0746 | 0.00691 | 0.00173 | 0.006 | NA | 24.6 |

(a) Percentage calculated based on group B as the positive control group.
(b) Percentage calculated based on group C as the positive control group.
(c) NA = Not applicable.

Figure 6:
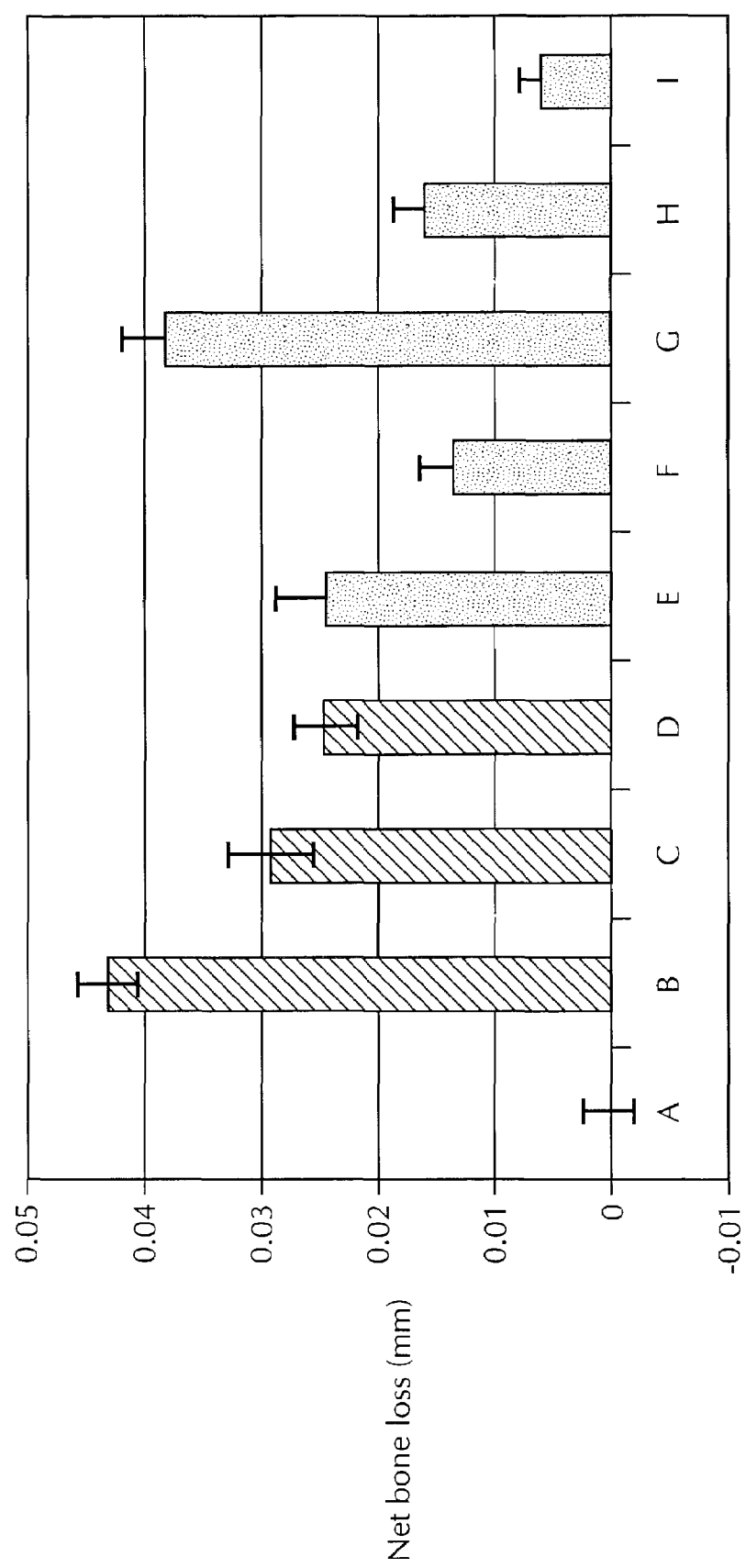
FIG. 6 is a graph showing the results of a homologous vaccine efficacy study based upon net bone loss.
Figure 7:
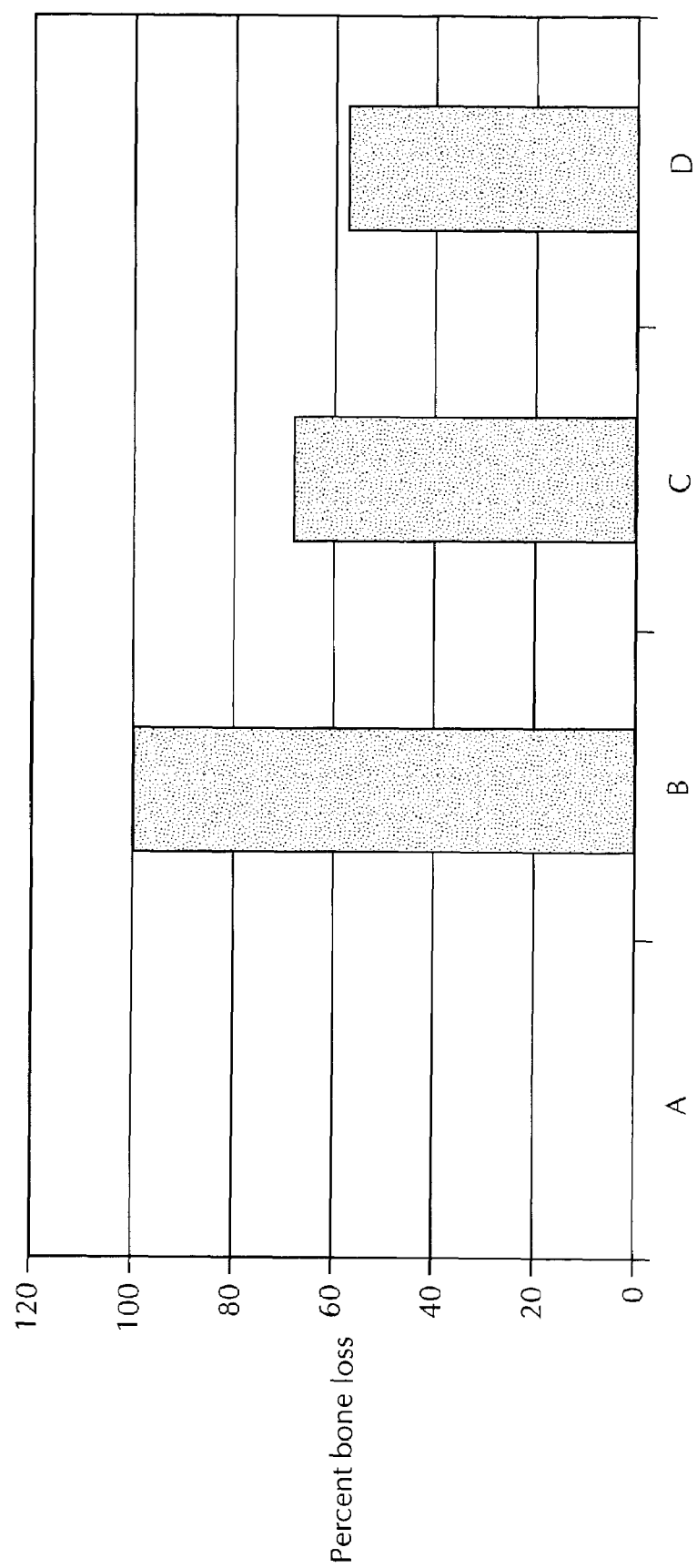
FIG. 7 is a graph showing a *P. gingivalis* 53977 homologous vaccine efficacy study based upon percent bone loss.
Figure 8:
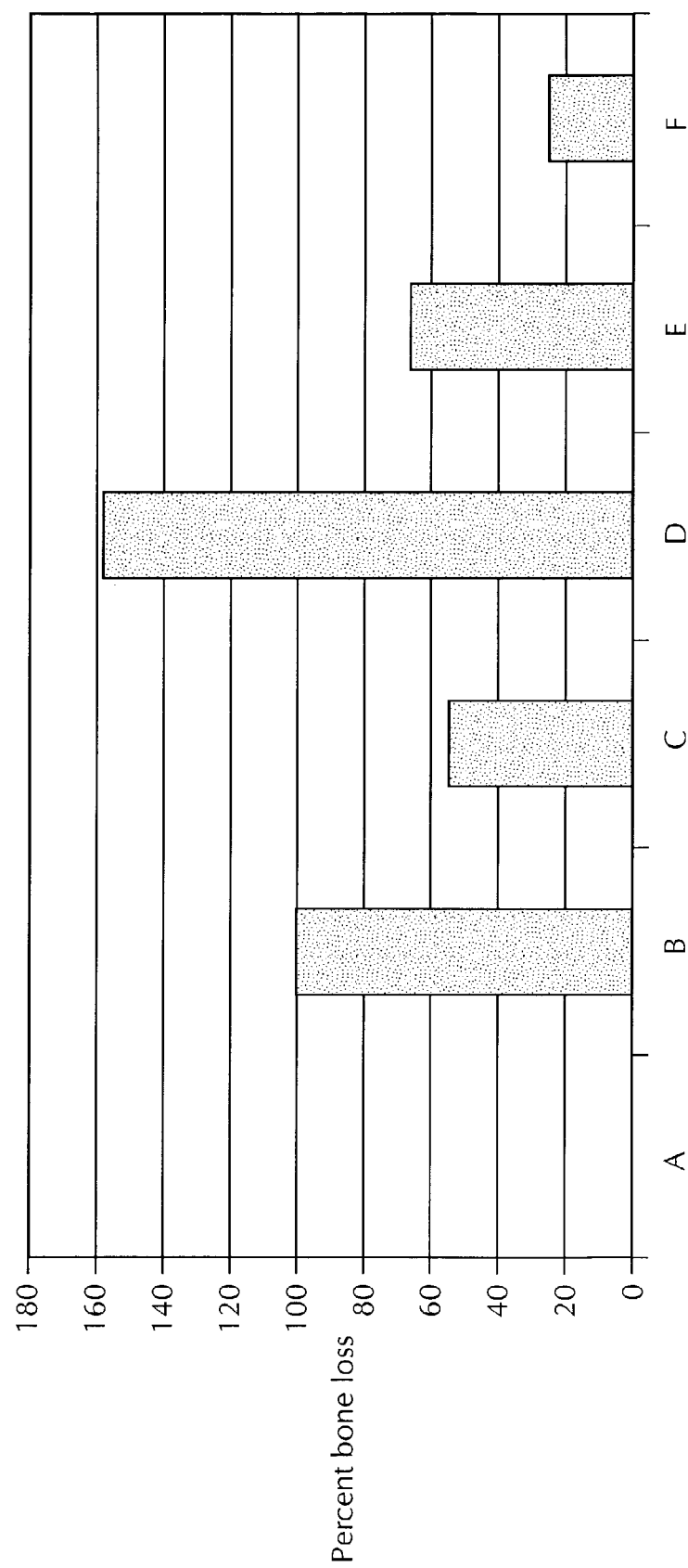
FIG. 8 is a graph showing a *P. gulae* B43 homologous vaccine efficacy study based upon percent bone loss.

FIGS. 6, 7, and 8 graphically display these results. FIG. 7 shows the percent bone loss for the control experiment. Vaccines containing formalin-inactivated P. gingivalis 53977 and either Freund's complete/incomplete or MPL+TDM adjuvants reduced the bone loss induced by infection with P. gingivalis 53977 by approximately 32% and 43%, respectively. FIG. 8 shows the percent bone loss for the test experi- Heterologous Vaccine Efficacy Study In heterologous vaccine efficacy studies, mice were immunized with two injections of 0.2 ml each of either formalin-inactivated P. gulae B43 or formalin-inactivated P. salivosa B104 and P. denticanis B106 cells in MPL+TDM adjuvant three weeks apart. The mice were infected as previously described with either *P. gulae* B43, *P. gulae* B69, *P. salivosa* B104, or *P. denticanis* B106 two weeks following the booster immunization. Forty-two days following the infection, the mice were sacrificed and processed as previously described. Table 6 shows the numerical results of bone loss measurements.

of providing protection not only from homologous challenge, but also from heterologous challenge with *P. gulae* B69. Moreover, protection was observed between two *Porphyromonas* species as the *P. gulae* B43 vaccine protected against *P. salivosa* B104 challenge. Extrapolating this data into the clinical setting, a multi-valent vaccine would likely be effi-

TABLE 6

Mouse heterologous vaccine efficacy study results.

| Group | Vaccinogen | Inactivation method | Challenge | Mean bone loss | Std. Dev. | SEM | Net bone loss | % bone loss[a] | % bone loss[b] | % bone loss[c] | % bone loss[d] |
|---|---|---|---|---|---|---|---|---|---|---|---|
| A | PBS | NA | None | 0.088 | 0.0112 | 0.00299 | 0 | 0 | 0 | 0 | 0 |
| B | PBS | NA | *P. gulae* B43 | 0.101 | 0.0103 | 0.00266 | 0.013 | 100 | NA[e] | NA | NA |
| C | PBS | NA | *P. gulae* B69 | 0.115 | 0.0112 | 0.00289 | 0.027 | NA | 100 | NA | NA |
| D | PBS | NA | *P. salivosa* B104 | 0.101 | 0.0132 | 0.00352 | 0.013 | NA | NA | 100 | NA |
| E | PBS | NA | *P. pfizerii* B106 | 0.0994 | 0.0135 | 0.0035 | 0.0114 | NA | NA | NA | 100 |
| F | *P. gulae* B43 | Formalin | *P. gulae* B43 | 0.0901 | 0.016 | 0.00412 | 0.0021 | 16.15 | NA | NA | NA |
| G | *P. gulae* B43 | Formalin | *P. gulae* B69 | 0.104 | 0.0166 | 0.00443 | 0.016 | NA | 59.26 | NA | NA |
| H | *P. gulae* B43 | Formalin | *P. salivosa* B104 | 0.0926 | 0.0119 | 0.00319 | 0.0046 | NA | NA | 35.38 | NA |
| I | *P. gulae* B43 | Formalin | *P. pfizerii* B106 | 0.102 | 0.0124 | 0.00333 | 0.014 | NA | NA | NA | 122.8 |
| J | *P. salivosa* B104/ *P. denticanis* B106 | Formalin | *P. gulae* B69 | 0.102 | 0.0124 | 0.00333 | 0.014 | NA | 51.85 | NA | NA |

[a]Percentage bone loss is calculated for the *P. gulae* B43 infected mice.
[b]Percentage bone loss is calculated for the *P. gulae* B69 infected mice.
[c]Percentage bone loss is calculated for the *P. salivosa* B104 infected mice.
[d]Percentage bone loss is calculated for the *P. denticanis* B106 infected mice.
[e]NA, not applicable.

Figure 9:
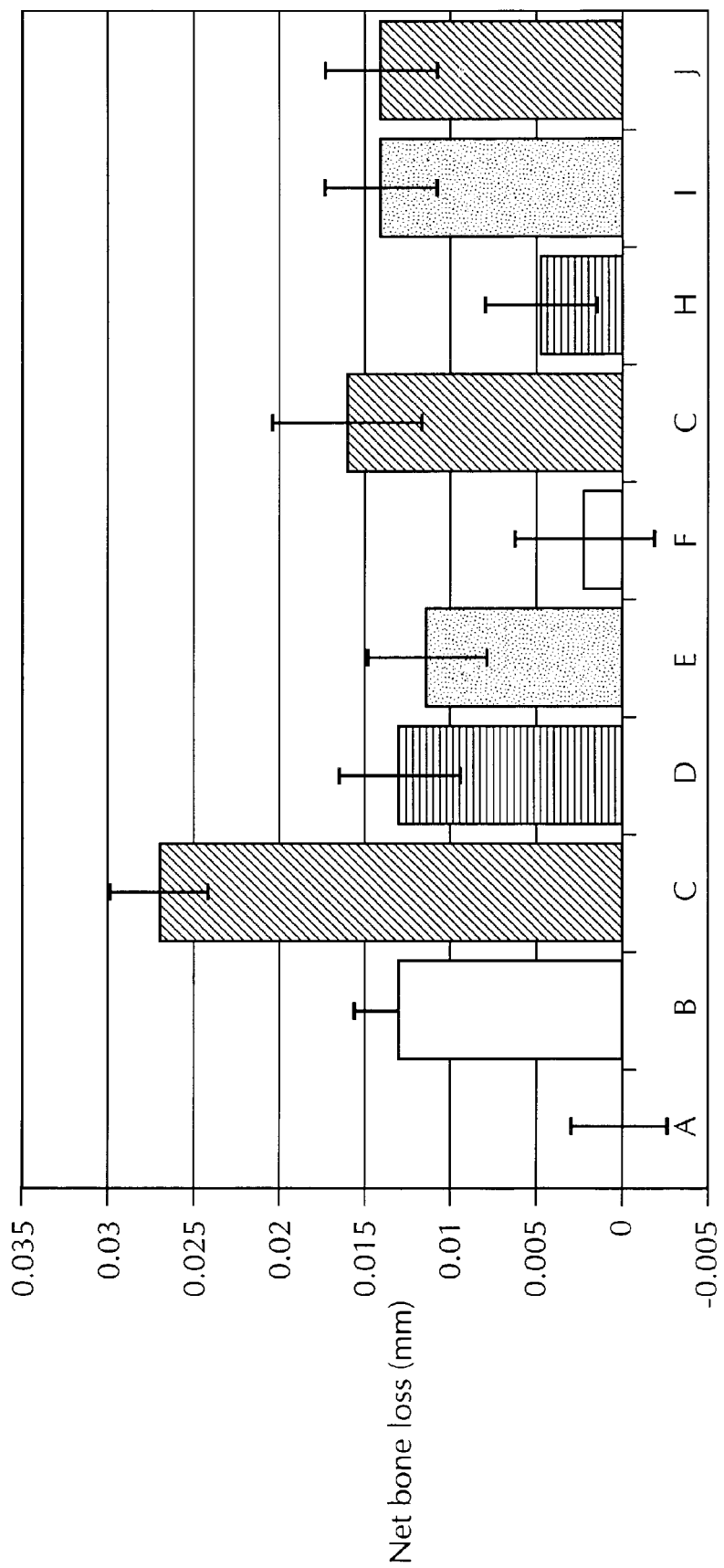
FIG. 9 is a graph showing the results of a heterologous vaccine efficacy study based upon net bone loss.
Figure 10:
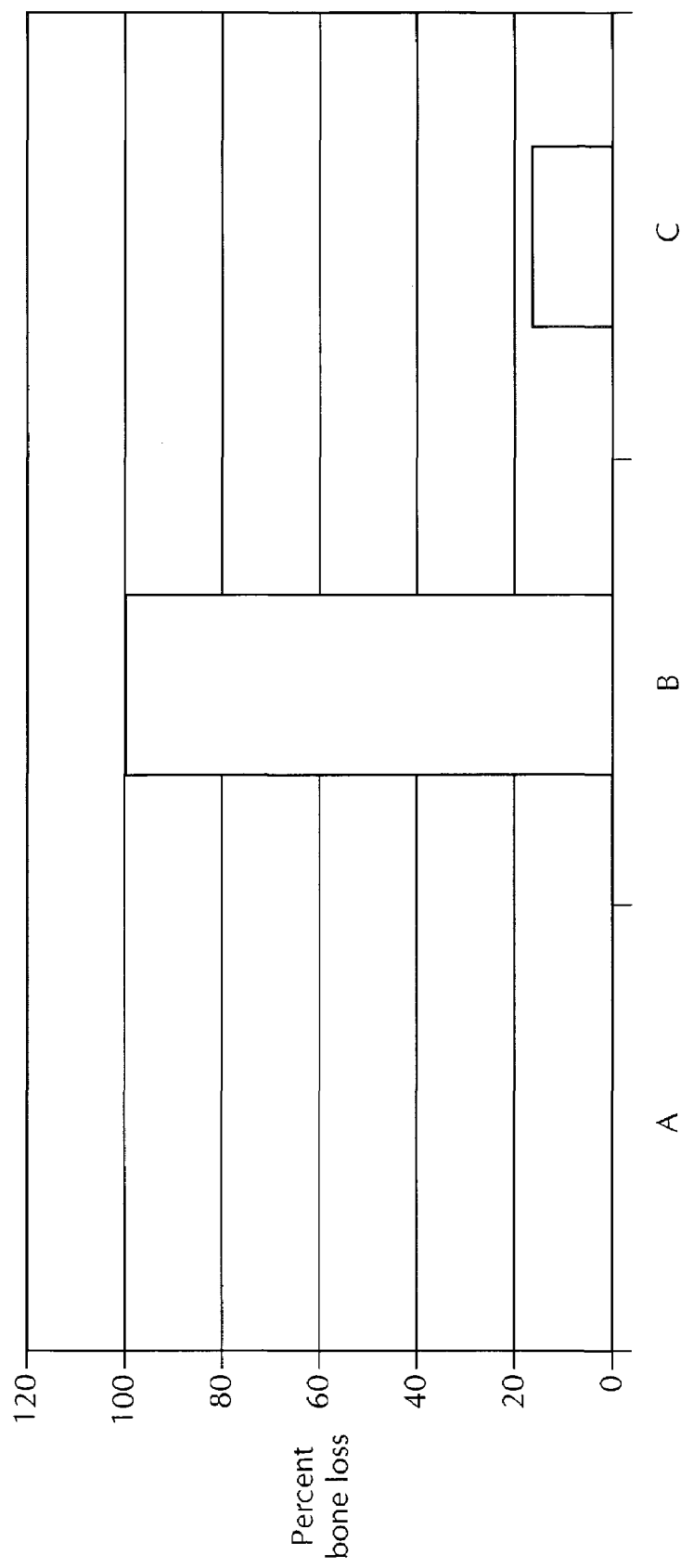
FIG. 10 is a graph showing the results for *P. gulae* B43 challenge groups of the heterologous vaccine efficacy study based upon percent bone loss.
Figure 11:
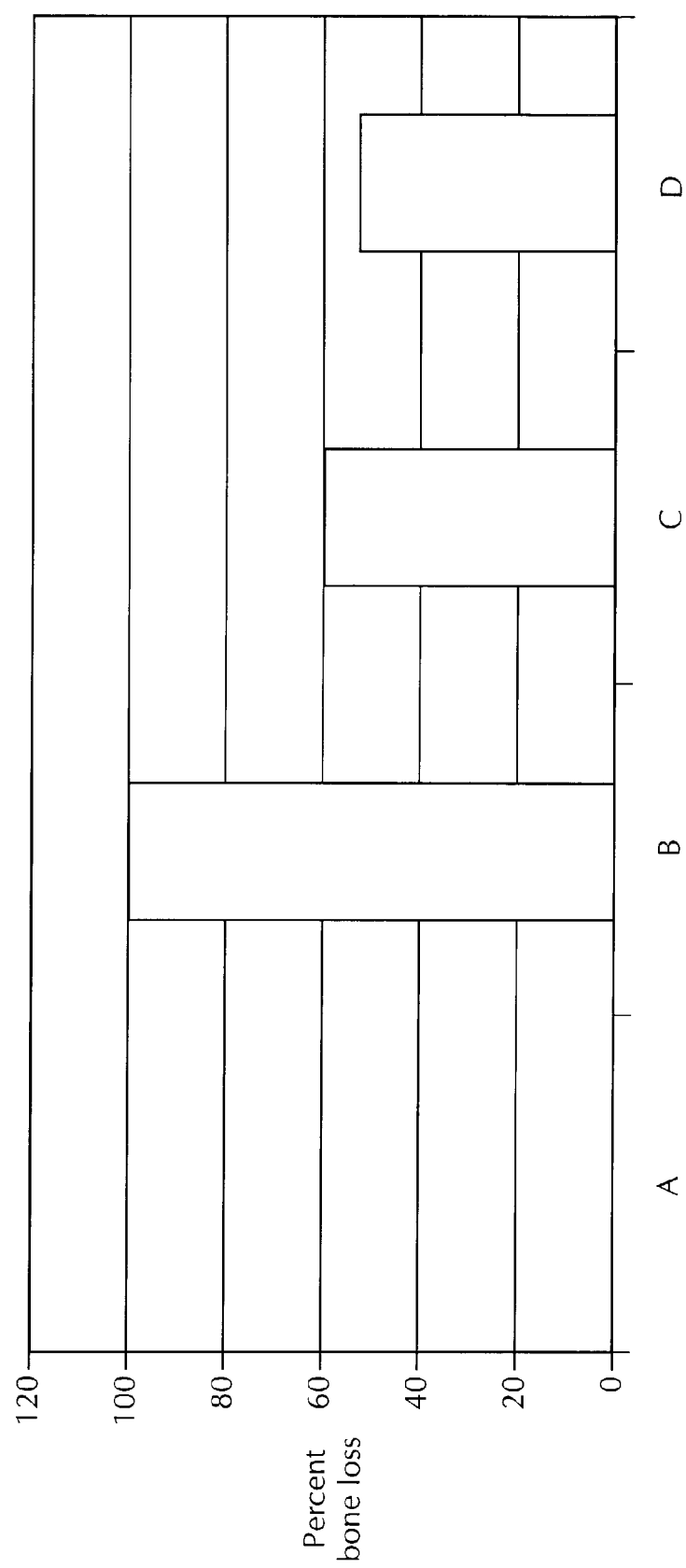
FIG. 11 is a graph showing the results for *P. gulae* B69 challenge groups of the heterologous vaccine efficacy study based upon percent bone loss.
Figure 12:
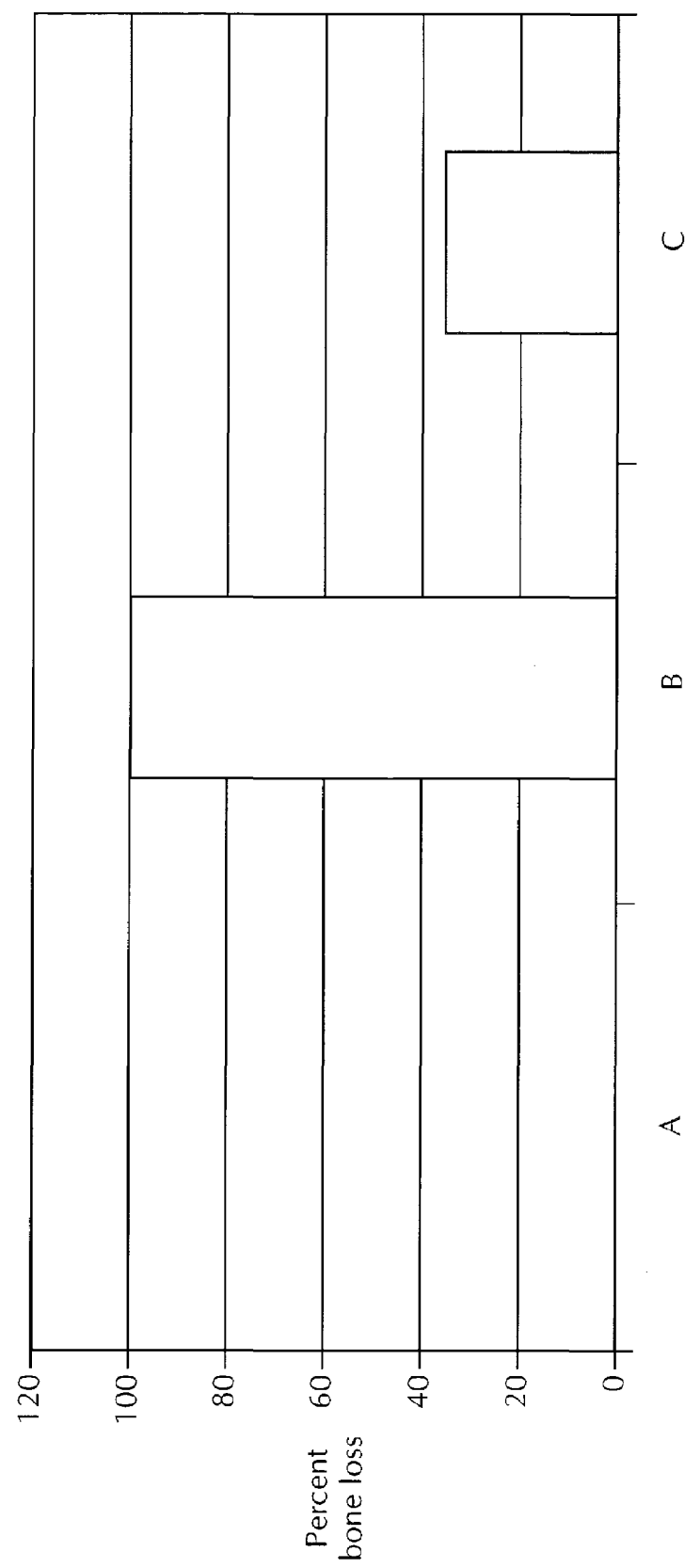
FIG. 12 is a graph showing the results for *P. salivosa* B104 challenge groups of the heterologous vaccine efficacy study based upon percent bone loss.
Figure 13:
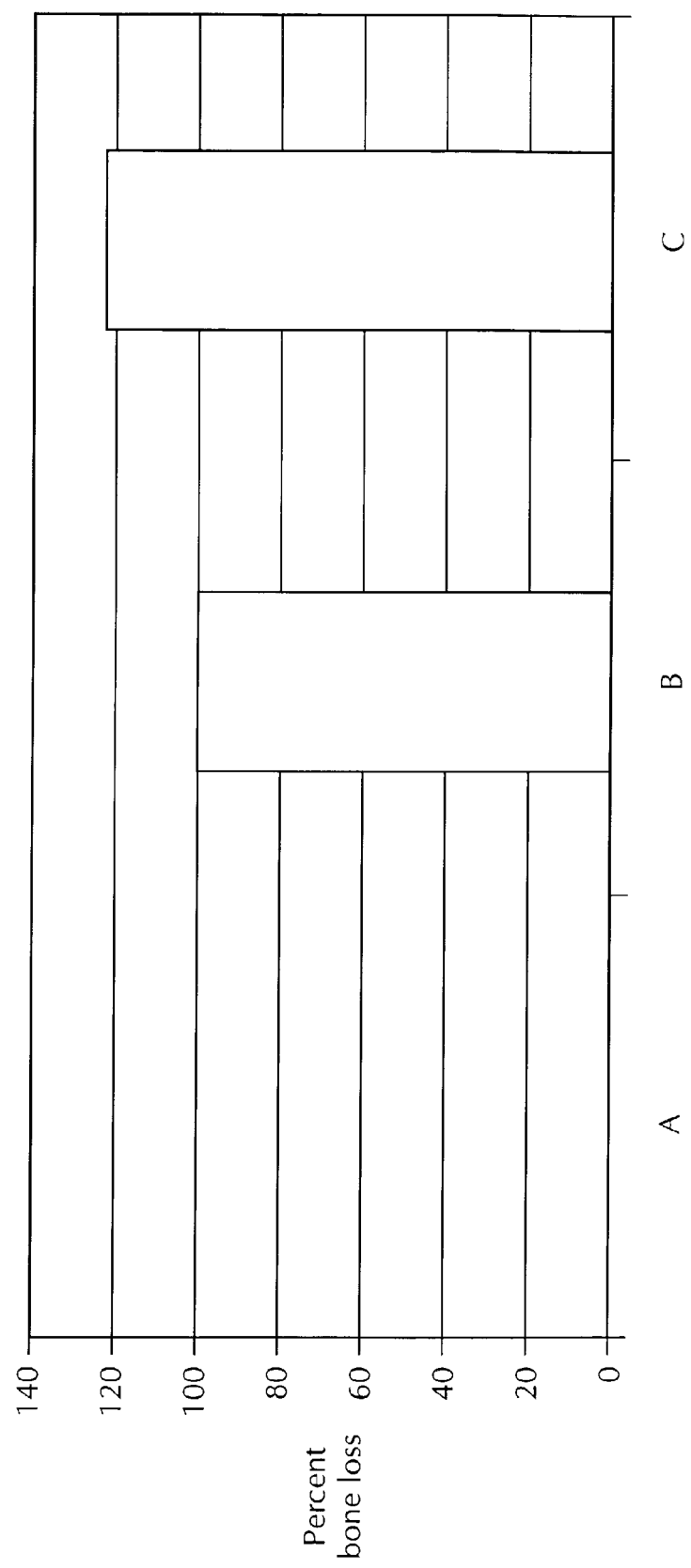
FIG. 13 is a graph showing the results for *P. denticanis* B106 challenge groups of the heterologous vaccine efficacy study based upon percent bone loss.

FIGS. 9, 10, 11, 12, and 13 graphically display these results. FIG. 9 shows the net bone loss for these experiments. FIG. 10 shows the percent bone loss for the *P. gulae* B43 infected groups. (Columns A, B and C represent Groups A, B and F from Table 6, respectively.) Formalin-inactivated *P. gulae* B43 and MPL+TDM adjuvant reduced the bone loss induced by infection with *P. gulae* B43 by approximately 84%. FIG. 11 shows the percent bone loss for the *P. gulae* B69 infected groups. (Columns A, B, C and D represent Groups A, C, G and J from Table 6, respectively.) The formalin-inactivated *P. gulae* B43 and formalin-inactivated *P. salivosa* B104/ *P. denticanis* B106 vaccines containing MPL+TDM adjuvant reduced the bone loss induced by infection with *P. gulae* B69 by approximately 40% and 49%, respectively. FIG. 12 shows the percent bone loss for the *P. salivosa* B104 infected groups. Formalin-inactivated *P. gulae* B43 and MPL+TDM adjuvant reduced the bone loss induced by *P. salivosa* B104 by approximately 65%. FIG. 13 shows the percent bone loss for the *P. denticanis* B106 infected groups. Formalin-inactivated *P. gulae* B43 with MPL+TDM adjuvant failed to cross protect against challenge with *P. denticanis* B106. Based on these data, it can be concluded that the formalin-inactivated *P. gulae* B43 vaccine adjuvanted with MPL+TDM was capable cacious in the prophylactic prevention of periodontal disease and may well prove efficacious in the therapeutic treatment of periodontal disease.

Recombinant FimA and OprF Mouse Serological Study

Figure 14:
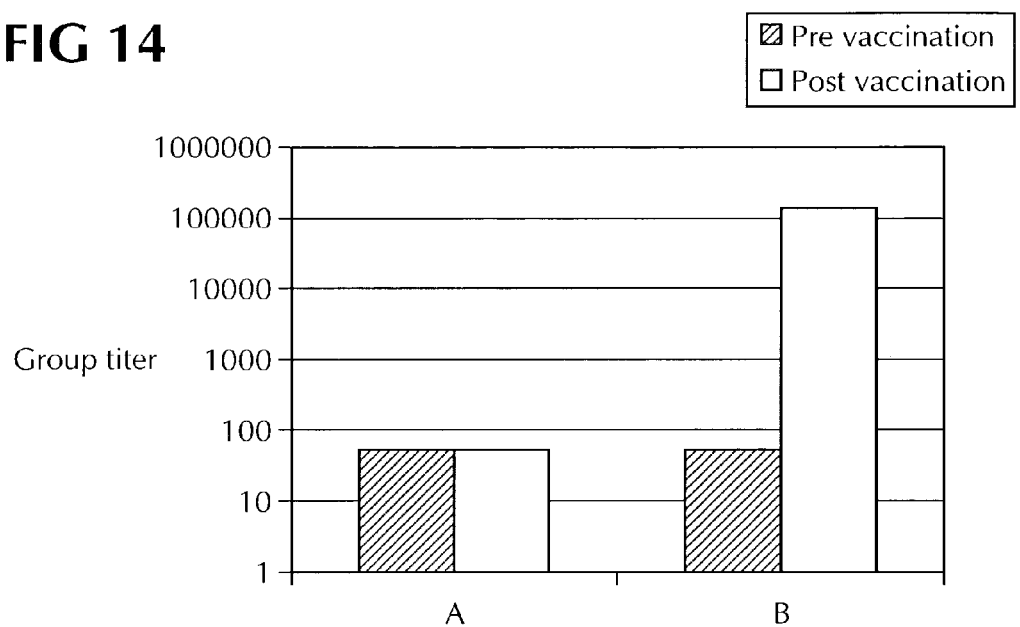
FIG. 14 is a graph showing the serological results of mice vaccinated with recombinant *P. gulae* B43 FimA or saline utilizing a FimA specific ELISA.
Figure 15:
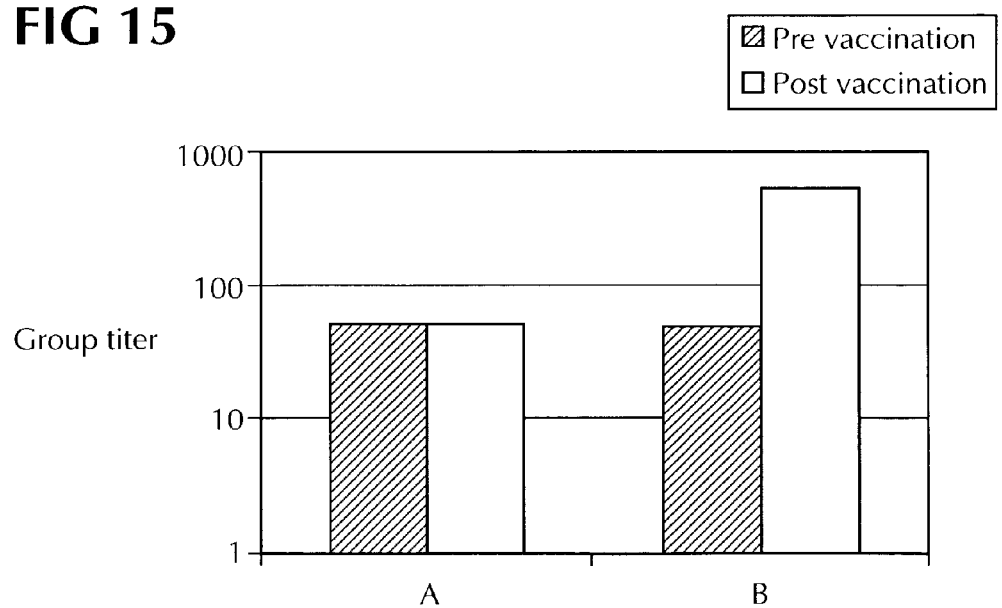
FIG. 15 is a graph showing the serological results of mice vaccinated with recombinant *P. gulae* B43 OprF or saline utilizing an OprF specific ELISA.

In subunit vaccine serology studies, mice were immunized with two injections of 0.2 ml each of either recombinantly expressed, purified *P. gulae* B43 FimA or recombinantly expressed, purified *P. gulae* B43 OprF in QuilA/Cholesterol adjuvant three weeks apart. The mice were bled prior to the first vaccination and two weeks following the booster immunization. Table 7 shows the numerical results while FIGS. 14 and 15 show the results graphically.

TABLE 7

Mouse subunit vaccine serology study.

| | | rFimA ELISA | | rOprF ELISA | |
|---|---|---|---|---|---|
| Group | Vaccinogen | Pre-vaccination | Post-vaccination | Pre-vaccination | Post-vaccination |
| A | Saline | 50 | 50 | 50 | 50 |
| B | rFimA + QAC | 50 | 138889 | NA | NA |
| C | rOprF + QAC | NA | NA | 50 | 118 |

Throughout this application, various patent and scientific publications, including United States patents, are referenced by author and year and patents by number. The disclosures of these publications and patents are hereby incorporated by reference in their entireties into this application in order to more fully describe the state of the art to which this invention pertains.

What is claimed is:

1. A vaccine for treating or preventing periodontal disease in dogs or cats comprising an immunologically effective amount of an inactivated pigmented anaerobic bacteria and a pharmaceutically acceptable carrier, wherein said pigmented anaerobic bacteria is *Porphyromonas. gulae* and said bacteria is capable of colonizing the oral cavity of dogs or cats and causes, either directly or in combination with other pathogenic agents, periodontal disease in dogs or cats and wherein its 16S rRNA DNA comprises the nucleic acid sequence, SEQ ID NO: 86.

2. A kit comprising, in at least one container, a composition for treating or preventing periodontal disease in dogs or cats comprising an effective amount of at least one inactivated isolated pigmented anaerobic bacteria and a pharmaceutically acceptable carrier, wherein said pigmented anaerobic bacteria is *Porpnhyromonas. gulae* and said bacteria is capable of colonizing the oral cavity of dogs or cats and causes, either directly or in combination with other pathogenic agents, periodontal disease in dogs or cats, and wherein its 16S rRNA DNA comprises the nucleic acid sequence, SEQ ID NO: 86; and wherein the kit further comprises a set of printed instructions indicating that the kit is useful for treating or preventing periodontal disease in dogs or cats.

3. The kit according to claim 2, wherein said kit further comprises a dispenser for dispensing said composition.

4. The vaccine according to claim 1, further comprising an adjuvant.

* * * * *

SEQUENCE LISTING

<160> NUMBER OF SEQ ID NOS: 137

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: D0056

<400> SEQUENCE: 1
ggattagata ccctggtagt c                                             21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: D0057

<400> SEQUENCE: 2
cccgggaacg tattcaccg                                                19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PFZ175-AP1

<400> SEQUENCE: 3
ggcttaagtg ccataacgag                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PFZ175-AP2

<400> SEQUENCE: 4
ctggcgtctt acgacggctg                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PFZ175-AP3

<400> SEQUENCE: 5
tgtcgtcagc tcgtgccgtg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:D0067

<400> SEQUENCE: 6
gcgcagcaag gccagcccgg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:D0068

<400> SEQUENCE: 7
gagcgaaccc cgctccctgt                                               20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:D0078

<400> SEQUENCE: 8
gcgacgctat atgcaagaca atc                                           23

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:D0097

<400> SEQUENCE: 9
ggcctcgaga acaaagacaa cgaagcagaa ccc                                33

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:D0098

<400> SEQUENCE: 10
ggcaagctta ccaaataaca ttttgtacaa cacc                               34

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:PFZ185-AP1

<400> SEQUENCE: 11
tcatccgaca atcctgtgtg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:PFZ185-AP2

<400> SEQUENCE: 12
agcagctgct aaatcggctc                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:PFZ185-AP3

```
<400> SEQUENCE: 13
ttggcaagac tcttgcagag                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PFZ185-AP4

<400> SEQUENCE: 14
ctgcagtcag ttcagttgtc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PFZ186-AP1

<400> SEQUENCE: 15
tacgtcaaca ggctctgctg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:PFZ186-AP2

<400> SEQUENCE: 16
gacaactgaa ctaactgcag                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:PFZ186-AP3

<400> SEQUENCE: 17
aacatagaaa ccttgtggag                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:PFZ186-AP4

<400> SEQUENCE: 18
tgtcgtctgg ttgggaagag                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:PFZ186-AP5

<400> SEQUENCE: 19
aatctgattg cctccctgag                                              20

<210> SEQ ID NO 20
<211> LENGTH: 20
```

```
<212> TYPE: DNA
<213> ORGANISM: Artificial Sequence
<220> FEATURE:
<223> OTHER INFORMATION: Description of Artificial Sequence:PFZ187-AP1

<400> SEQUENCE: 20
gggaaccgat ttagcagcag                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PFZ187-AP2

<400> SEQUENCE: 21
ccaatacagg gtaataggtc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:PFZ187-AP3

<400> SEQUENCE: 22
gttgtcaatg cttttacctc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:PFZ187-AP4

<400> SEQUENCE: 23
gattgagaat atcaaatgtg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:PFZ187-AP5

<400> SEQUENCE: 24
ttaggcgtat aaccattgtc                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:PFZ187-AP6

<400> SEQUENCE: 25
atttaacggt gcttacacac                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:PFZ187-AP7

<400> SEQUENCE: 26
```
ccaattggcg gcctgagctg                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:PFZ187-AP8

<400> SEQUENCE: 27
tggcatagtt ggtaggtgtg                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:PFZ187-AP9

<400> SEQUENCE: 28
tgtaagcacc gttaaatgtg                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:PFZ187-AP11

<400> SEQUENCE: 29
ctgacaggtt ctttgaccac                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:PFZ187-AP12

<400> SEQUENCE: 30
tgttccttgg ttgagccgtg                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:PFZ187-AP13

<400> SEQUENCE: 31
gtggtcaaag aacctgtcag                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:PFZ187-AP14

<400> SEQUENCE: 32
cataaacaca caggattgtc                                                   20

<210> SEQ ID NO 33
<211> LENGTH: 20
<212> TYPE: DNA
<213> ORGANISM: Artificial Sequence

```
<220> FEATURE:
<223> OTHER INFORMATION: Description of Artificial Sequence:PFZ187-AP15

<400> SEQUENCE: 33 ttgcttctttgcaatgagac                                                  20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:PFZ187-AP16

<400> SEQUENCE: 34 agccatgcgagcatgtacac                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:PFZ187-AP17

<400> SEQUENCE: 35 ctgtcatgatcaaacctgtg                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:PFZ187-AP18

<400> SEQUENCE: 36 accgtctgcattcacgagtg                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:PFZ188-AP1

<400> SEQUENCE: 37 gccttccaatgatgctccac                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:PFZ188-AP2

<400> SEQUENCE: 38 ggacgtagacctgcattctg                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:PFZ188-AP3

<400> SEQUENCE: 39 cgcaatacgggcatgaacac                                                  20
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:PFZ188-AP4

<400> SEQUENCE: 40
ttatggttat gatggacctc                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:PFZ188-AP5

<400> SEQUENCE: 41
tggtactcct ttgagttctg                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:PFZ188-AP6

<400> SEQUENCE: 42
cacacttgcg cggtaaccac                                              20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence:D0086

<400> SEQUENCE: 43
atgaaggtaa agtacttaat gc                                           22

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence:D0087

<400> SEQUENCE: 44
agatgaatta cttggagcga acgat                                        25

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:KWK-Pg-03

<400> SEQUENCE: 45
ttacttggag cgaacgatta caacacg                                      27

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:PFZ209-AP1

<400> SEQUENCE: 46
ttggtgcagc tcacttcgac        20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:PFZ209-AP2

<400> SEQUENCE: 47
accacatcaa acataaagtc        20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:PFZ209-AP3

<400> SEQUENCE: 48
acattcgggg catgatacag        20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:PFZ209-AP4

<400> SEQUENCE: 49
atgccattga gccaatggac        20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:PFZ210-AP1

<400> SEQUENCE: 50
ttgacttcat gttcgatgtg        20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:PFZ210-AP2

<400> SEQUENCE: 51
tgccaatgaa ttttatgctg        20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:PFZ210-AP3

<400> SEQUENCE: 52
cgcttggaga gttcttcgac        20

<210> SEQ ID NO 53

```
<211> LENGTH: 20
<212> TYPE: DNA
<213> ORGANISM: Artificial Sequence
<220> FEATURE:
<223> OTHER INFORMATION: Description of Artificial Sequence:PFZ210-AP4

<400> SEQUENCE: 53
tatcaacgat ctgaatggtc                                                20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:PFZ211-AP1

<400> SEQUENCE: 54
aactacttca agccctacag                                                20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:PFZ211-AP2

<400> SEQUENCE: 55
cgtaacccaa acctacccac                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:PFZ211-AP3

<400> SEQUENCE: 56
acgggacgct tgctcaactc                                                20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:PFZ211-AP4

<400> SEQUENCE: 57
attggggctt ggtaaatgac                                                20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:PFZ211-AP5

<400> SEQUENCE: 58
atacgctcta cacgaggctc                                                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:PFZ212-AP1

<400> SEQUENCE: 59
```

-continued

```
ccgccatggc tggagctcac                                          20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:PFZ212-AP2

<400> SEQUENCE: 60
tttgaaacca tatcccacac                                          20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:PFZ212-AP3

<400> SEQUENCE: 61
agtaacttca ggacattctg                                          20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:PFZ212-AP4

<400> SEQUENCE: 62
acgtccagtt tcttgcccag                                          20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:PFZ213-AP1

<400> SEQUENCE: 63
ttgacttcat gttcgatgtg                                          20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:PFZ213-AP2

<400> SEQUENCE: 64
tttgtgttgg taaccaacac                                          20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:PFZ213-AP3

<400> SEQUENCE: 65
acaggacgct tagagagctc                                          20

<210> SEQ ID NO 66
<211> LENGTH: 20
<212> TYPE: DNA
```

```
<213> ORGANISM: Artificial Sequence
<220> FEATURE:
<223> OTHER INFORMATION: Description of Artificial Sequence:PFZ213-AP4

<400> SEQUENCE: 66
acgcgcttat caacgatctg                                            20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:PFZ213-AP5

<400> SEQUENCE: 67
cttcccaagg aacgtgtgtg                                            20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:PFZ214-AP1

<400> SEQUENCE: 68
actttatgtt tgatgttgtg                                            20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:PFZ214-AP2

<400> SEQUENCE: 69
ccaacaccga accaaggcac                                            20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:PFZ214-AP3

<400> SEQUENCE: 70
tctcaactca gtattctcag                                            20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:PFZ214-AP4

<400> SEQUENCE: 71
taaccttaat tttggtcgtg                                            20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:PFZ215-AP1

<400> SEQUENCE: 72
cacacctaca acactgccac                                            20
```

```
<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:PFZ215-AP2

<400> SEQUENCE: 73
tcaaacatga aatcatagtg                                            20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:PFZ215-AP3

<400> SEQUENCE: 74
ctcggggcag aaagcaggac                                            20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:PFZ215-AP4

<400> SEQUENCE: 75
gacttgaact ctcagatcag                                            20

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence:KWK-Pg-06

<400> SEQUENCE: 76
atgcaggaaa atactgtacc ggcaacg                                    27

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence:KWK-Pgu-14

<400> SEQUENCE: 77
gtgtgtcata tgcaggaaaa tactgtacc                                  29

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence:KWK-Pgu-15

<400> SEQUENCE: 78
gtgtgttcta gattattact tggagcgaac g                               31

<210> SEQ ID NO 79
<211> LENGTH: 22
<212> TYPE: DNA
<213> ORGANISM: Artificial Sequence
<220> FEATURE:
```

```
<223> OTHER INFORMATION: Description of Artificial Sequence:KWK-Ps-02

<400> SEQUENCE: 79
acacctgaga ctcagacatt gc                                              22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:KWK-Ps-02

<400> SEQUENCE: 80
catgcgcgag cctcaaaaag c                                               21

<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence:KWK-Ps-04b

<400> SEQUENCE: 81
cctgccactc aacagaaatc atatcagaag gaactcc                              37

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence:KWK-Ps-05b

<400> SEQUENCE: 82
ctgctcataa gacggctttt gaccgttctg cagg                                 34

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence:KWK-Ps-06b

<400> SEQUENCE: 83
cttttgaccg ttctgcagga cattggttct tgactctcc                            39

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence:D122

<400> SEQUENCE: 84
tggctaaryt gacygtaatg gtyta                                           25

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence:D123

<400> SEQUENCE: 85
agttyacyaa tacaggrtaa taggt                                           25
```

<210> SEQ ID NO 86
<211> LENGTH: 572
<212> TYPE: DNA
<213> ORGANISM: Artificial Sequence
<220> FEATURE:
<223> OTHER INFORMATION: Description of Artificial Sequence:P. gulae B43
    16S rRNA polynucleotide sequence

<400> SEQUENCE: 86
cacgcagtaa acgatgatta ctaggagttt gcgatatacc gtcaagcttc cacagcgaaa     60
gcgttaagta atccacctgg ggagtacgcc ggcaacggtg aaactcaaag gaattgacgg    120
gggcccgcac aagcggagga acatgtggtt taattcgatg atacgcgagg aaccttaccc    180
gggattgaaa tgtagacgac ggatggtgaa agccgtcttc ccttcggggc gtctatgtag    240
gtgctgcatg gttgtcgtca gctcgtgccg tgaggtgtcg gcttaagtgc cataacgagc    300
gcaacccaca tcggtagttg ctaacaggtt tagctgagga ctctaccgag actgccgtcg    360
taaggcgcga ggaaggtgtg gatgacgtca aatcagcacg gcccttacat ccggggcgac    420
acacgtgtta caatgggagg gacaaagggc agctaccggg cgaccgggtg cgaatctcga    480
aacccttccc cagttcggat cggagtctgc aactcgactc cgtgaagctg gattcgctag    540
taatcgcgca tcagccatgg cgcggtgaat ac                                  572

<210> SEQ ID NO 87
<211> LENGTH: 571
<212> TYPE: DNA
<213> ORGANISM: Artificial Sequence
<220> FEATURE:
<223> OTHER INFORMATION: Description of Artificial Sequence:P. cansulci
    B46 16S rRNA polynucleotide sequence

<400> SEQUENCE: 87
cacgccgtaa acgatgatta ctcggagtat gcgatatgag tgtatgcttc ttagcgaaag     60
cgttaagtaa tccacctggg gagtacgtcg gcaacgatga aactcaaagg aattgacggg    120
ggcccgcaca agcggaggaa catgtggttt aattcgatga tacgcgagga accttacccg    180
ggattgaaat atagatgaca ggcagcgaga gttgttatcc cttcggggca tctatgtagg    240
tgctgcatgg ttgtcgtcag ctcgtgccgt gaggtgtcgg cttaagtgcc taacgagcg    300 caacccacat tattagttac taacaggtta agctgaggac tctaataaga ctgccggcgt    360
aagccgtgag gaaggtgtgg atgacgtcaa atcagcacgg cccttacatc ggggcgaca    420 cacgtgttac aatggtaggg acaaagggca gctaccgggc gaccggatgc gaatctccaa    480
accctatccc agttcggatc ggagtctgca actcgactct gtgaagctgg attcgctagt    540
aatcgcgcat cagccatggc gcggtgaata c                                    571

<210> SEQ ID NO 88
<211> LENGTH: 573
<212> TYPE: DNA
<213> ORGANISM: Artificial Sequence
<220> FEATURE:
<223> OTHER INFORMATION: Description of Artificial Sequence:P.
    circumdentaria B52 16S rRNA polynucleotide
    sequence

<400> SEQUENCE: 88
cacgctgtaa acgatgaata ctagatttt gcgatataca gtaagagtct aagcgaaagc     60
gataagtatt ccacctgggg agtacgccgg caacggtgaa actcaaagga attgacgggg    120
gcccgcacaa gcggaggaac atgtggttta attcgatgat acgcgaggaa ccttacctgg    180

```
gattgaaatt taggagaacg atttatgaaa gtagatttc ccttcggggc tcctaagtag    240
gtgctgcatg gttgtcgtca gctcgtgccg tgaggtgtcg gcttaagtgc cataacgagc    300
gcaacccgcg ttgatagtta ctaacagata aagctgagga ctctatcgag acagccgtcg    360
taagacgcga ggaaggggcg gatgacgtca aatcagcacg gcccttacat ccagggcgac    420
acacgtgtta caatggcaag gacaaaggga agccacatag cgatatggag cagatcctca    480
aaccttgtcc cagttcggat cggagtctgc aactcgactc cgtgaagctg gattcgctag    540
taatcgcgca tcagccatgg cgcggtgaat acc                                573

<210> SEQ ID NO 89
<211> LENGTH: 573
<212> TYPE: DNA
<213> ORGANISM: Artificial Sequence
<220> FEATURE:
<223> OTHER INFORMATION: Description of Artificial Sequence:P. gulae B69
      16S rRNA polynucleotide sequence

<400> SEQUENCE: 89
cacgcagtaa acgatgatta ctaggagttt gcgatatacc gataagcttc cacagcgaaa    60
gcgttaagta atccacctgg ggagtacgcc ggcaacggtg aaactcaaag gaattgacgg    120
gggcccgcac aagcggagga acatgtggtt taattcgatg atacgcgagg aaccttaccc    180
gggattgaaa tgtagatgac agatggtgaa agccgtcttc ccttcggggc gtctatgtag    240
gtgctgcatg gttgtcgtca gctcgtgccg tgaggtgtcg gcttaagtgc cataacgagc    300
gcaacccata tcggtagttg ctaacaggtc aagctgagga ctctaccgag actgccgtcg    360
taaggcgaga ggaaggtgtg gatgacgtca aatcagcacg gcccttacat ccggggcgac    420
acacgtgtta caatgggagg gacaaagggc agctaccggg cgaccggatg cgaatctcga    480
aacccttccc cagttcggat cggagtctgc aactcgactc cgtgaagctg gattcgctag    540
taatcgcgca tcagccatgg cgcggtgaat acc                                573

<210> SEQ ID NO 90
<211> LENGTH: 572
<212> TYPE: DNA
<213> ORGANISM: Artificial Sequence
<220> FEATURE:
<223> OTHER INFORMATION: Description of Artificial Sequence:P.
      circumdentaria B97 16S rRNA polynucleotide
      sequence

<400> SEQUENCE: 90
cacgctgtaa acgatgaata ctagatttt gcgatataca gtaagagtct aagcgaaagc    60
gataagtatt ccacctgggg agtacgccgg caacggtgaa actcaaagga attgacgggg    120
gcccgcacaa gcggaggaac atgtggttta attcgatgat acgcgaggaa ccttacctgg    180
gattgaaatt taggagaacg atttatgaaa gtagattttc ccttcggggc tcctaagtag    240
gtgctgcatg gttgtcgtca gctcgtgccg tgaggtgtcg gcttaagtgc cataacgagc    300
gcaacccgcg tcgatagtta ctaacaggta atgctgagga ctctatcgag acagccgtcg    360
taagacgaga ggaaggggcg gatgacgtca aatcagcacg gcccttacat ccagggcgac    420
acacgtgtta caatggcaag gacaaaggga agccacatag cgatatggag cagatcctca    480
aaccttgtcc cagttcggat cggagtctgc aactcgactc cgtgaagctg gattcgctag    540
taatcgcgca tcagccatgg cgcggtgaat ac                                 572

<210> SEQ ID NO 91
```

<211> LENGTH: 571
<212> TYPE: DNA
<213> ORGANISM: Artificial Sequence
<220> FEATURE:
<223> OTHER INFORMATION: Description of Artificial Sequence:P.
      cangingivalis B98 16S rRNA polynucleotide sequence

<400> SEQUENCE: 91

| | |
|---|---|
| cagtaaacga tgattactcg gagtatgcga tatatggtat gctcccaagg gaaaccgata | 60 |
| agtaatccac ctggggagta cgccggcaac ggtgaaactc aaaggaattg acggggccc | 120 |
| gcacaagcgg aggaacatgt ggtttaattc gatgatacgc gaggaacctt acccgggatt | 180 |
| gaaatgtaca tgacggttgg gcgagagcct gacttcccct cggggcatgt atgtaggtgc | 240 |
| tgcatggttg tcgtcagctc gtgccgtgag gtgtcggctt aagtgccata acgagcgcaa | 300 |
| cccacatcgt cagttactaa caggtagagc tgaggactct gacgagactg ccgtcgtaag | 360 |
| gcgcgaggaa ggtgtggatg acgtcaaatc agcacggccc ttacatccgg ggcgacacac | 420 |
| gtgttacaat ggtagggaca aagggcagct acctggcgac aggatgcgaa tctccaaacc | 480 |
| ctatctcagt tcggatcgga gtctgcaact cgactccgtg aagctggatt cgctagtaat | 540 |
| cgcgcatcag ccatggcgcg gtgaatacgt t | 571 |

<210> SEQ ID NO 92
<211> LENGTH: 384
<212> TYPE: DNA
<213> ORGANISM: Artificial Sequence
<220> FEATURE:
<223> OTHER INFORMATION: Description of Artificial Sequence:P. salivosa
      B104 16S rRNA polynucleotide sequence

<400> SEQUENCE: 92

| | |
|---|---|
| cagtaaacga tgataactgg gcgtatgcga tatacagtat gctcctgagc gaaagcgtta | 60 |
| agttatccac ctggggagta cgccggcaac ggtgaaactc aaaggaattg acggggccc | 120 |
| gcacaagcgg aggaacatgt ggtttaattc gatgatacgc gaggaacctt acccgggatt | 180 |
| gaaatttagc ggactatgta tgaaagtaca tatcctgtca caaggccgct aagtaggtgc | 240 |
| tgcatggttg tcgtcagctc gtgccgtgag gtgtcggctt aagtgccata acgagcgcaa | 300 |
| cccacgttgt cagttactat cgggtaaagc cgaggactct gacaagactg ccgtcgtaag | 360 |
| gcgcgaggaa ggtgtggatg acgt | 384 |

<210> SEQ ID NO 93
<211> LENGTH: 571
<212> TYPE: DNA
<213> ORGANISM: Artificial Sequence
<220> FEATURE:
<223> OTHER INFORMATION: Description of Artificial Sequence:P.
      denticanis B106 16S rRNA polynucleotide sequence

<400> SEQUENCE: 93

| | |
|---|---|
| cacgccgtaa acgatgctca ccggctctat gcgataagac agtatggggc taatagaaat | 60 |
| aattaagtga gccacctggg gagtacgtcg gcaacgatga aactcaaagg aattgacggg | 120 |
| ggcccgcaca agcggaggaa catgtggttt aattcgatga tacgcgagga accttacccg | 180 |
| ggtttaaatg tatgttgcat tatgtagaaa tacgtatttt cttcggaact gcatacaagg | 240 |
| tgctgcatgg ttgtcgtcag ctcgtgccgt gaggtgtcgg gttaagtccc ataacgagcg | 300 |
| caacccttat gattagttgc taacggttca agccgagcac tctattcaca ctgccaccgt | 360 |
| aaggtgcgag gaaggagggg atgatgtcaa atcagcacgg cccttatatc cggggctaca | 420 |

```
cacgtgttac aatggtcggt acagcgggtt gcatttacgt gagtaacagc taatcccaaa    480
aatcggtctc agttcggatt ggagtctgca actcgactcc atgaagttgg attcgctagt    540
aatcgcacat cagccatggt gcggtgaata c                                   571
```

<210> SEQ ID NO 94
<211> LENGTH: 571
<212> TYPE: DNA
<213> ORGANISM: Artificial Sequence
<220> FEATURE:
<223> OTHER INFORMATION: Description of Artificial Sequence:P.
      endodontalis B114 16S rRNA polynucleotide sequence

<400> SEQUENCE: 94

```
caccgcagta aacgatgaat actagatctt tgcgatatac ggtaagggtc taagcgaaag     60
cgataagtat tccacctggg gagtacgtcg gcaacgatga aactcaaagg aattgacggg    120
ggcccgcaca agcggaggaa catgtggttt aattcgatga tacgcgagga accttacccg    180
ggattgaaat ttagcgggcg ggctatgaga gtagcctttc ctacgggact gctaagtagg    240
tgctgcatgg ttgtcgtcag ctcgtgccgt gaggtgttgg cttaagtgcc ataacgagcg    300
caacccacgt tgatagttac taacagttaa agctgaggac tctatcgaga cagccggcgt    360
aagccgtgag gaaggtgtgg atgacgtcaa atcagcacgg cccttacatc cggggcgaca    420
cacgtgttac aatggtgagg acagcgggaa gcggcctggt gacaggtagc agatccccaa    480
acctcatccc agttcggatt ggagtctgca actcgactct atgaagctgg attcgctagt    540
aatcgcgcat cagccatggc gcggtgaata c                                   571
```

<210> SEQ ID NO 95
<211> LENGTH: 1024
<212> TYPE: DNA
<213> ORGANISM: Artificial Sequence
<220> FEATURE:
<223> OTHER INFORMATION: Description of Artificial Sequence:P. gulae B43
      fimA polynucleotide sequence

<400> SEQUENCE: 95

```
tctaaatcga aaagatcct aataaaacaa tattcacttt taaaacaaaa acgagatgaa      60
aaagactaag ttttcttgt tgggacttgc tgcccttgct atgacagctt gtaacaaaga    120
caacgaagca gaacccgttg tagaaggtaa cgctaccatt agcgtagtat tgaagaccag    180
caatccgaat cgtgctttcg gggttgcaga tgacgaagca aaagtggcta aactgactgt    240
aatggtctac aagggtgagc agcaggaagc catcaaatca gccgaaaatg caattaaggt    300
tgagaacatc aaatgtggtg caggctcacg tacgctggtc gtaatggcca atacgggtgg    360
aatggaattg gctggcaaga ctcttgcaga ggtaaaagca ttgacaactg aactaactgc    420
agaaaaccaa gaggctacag gtttgatcat gacagcagag cctgttgacg taacacttgt    480
cgccggcaat aactattatg gttatgatgg aactcaggga ggcaatcaga tttcgcaagg    540
tactcctctt gaaatcaaac gtgttcatgc ccgtattgcg ttcaccaaga ttgaagtgaa    600
gatgagcgag tctatgtga acaaatacaa ctttaccccc gaaaacatct atgcacttgt    660
ggctaagaag aagtctaatc tattcggtac ttcattggca aatagtgatg atgcttattt    720
gaccggttct ttgacgactt tcaacggtgc ttatacccct gcaaactata ctcatgtcgt    780
ctggttggga agaggctaca cagcgccttc caatgatgct ccacaaggtt tctatgttt     840 ggagagtgca tacgctcaga atgcaggtct acgtcctacc attctatgtg taaagggtaa    900
gctgacaaag catgatggta ctccttttgag ttctgaggaa atgacagctg cattcaatgc    960
```

```
cggctggatt gttgcaaaca atgatcctac gacctattat cctgtattag tgaactttga    1020
gagc                                                                 1024
```

<210> SEQ ID NO 96
<211> LENGTH: 733
<212> TYPE: DNA
<213> ORGANISM: Artificial Sequence
<220> FEATURE:
<223> OTHER INFORMATION: Description of Artificial Sequence:P.
      circumdentaria B52 fimA polynucleotide sequence

<400> SEQUENCE: 96

```
taatggagaa cagcaggaag ccatcgaatc agccgaaaat gcgactaaga ttgagaatat      60
caaatgtggt gcaggccaac gtacgctggt cgtaatggcc aatacgggtg aatggaatt     120 ggctggcaag actcttgcag aggtaaaagc attgacaact gtactgactg aagaaaacca    180
agaggccaca ggtttgatca tgacagcaga gccaaaagca atcgttttga aggcaggcaa    240
gaactatatt ggatacgatg gagccggaga gggcaaccac attgagaatg ctcctcttga    300
aatcaaacgt gtacatgctc gcatggcttt caccgaaatt aaagtacaga tgagcgcagc    360
ctacgataac atttacacat ttaccccctga aaagatttat ggtctcattg caaagaagca    420
atctaatttg ttcggggcaa cactcgtgaa tgcagacgct aattatctga caggttcttt    480
gaccacattt aacggtgctt acacacctac caactatgcc aatgttcctt ggttgagccg    540
tgattacgtt gcacctaccg ctggtgctcc tcagggcttc tacgtattag aaaatgacta    600
ctcagctaac agtggaacta ttcatccgac aatcctgtgt gtttatggca aacttcagaa    660
aaacggagcc gacctgacgg gaaccgattt agcagcagct caggccgcca attgggtgga    720
tgcagaaggc aag                                                       733
```

<210> SEQ ID NO 97
<211> LENGTH: 1024
<212> TYPE: DNA
<213> ORGANISM: Artificial Sequence
<220> FEATURE:
<223> OTHER INFORMATION: Description of Artificial Sequence:P. gulae B69
      fimA polynucleotide sequence

<400> SEQUENCE: 97

```
ggcgcagcat aacctcgacg aactgcgaca ctatatgcag gacaatctct aaatcgaata     60
aagattctaa taaacaata ttcacttta aacaaaaac aagatgaaaa agactaagtt      120
tttcttgttg ggacttgctg cccttgctat gacagcttgt aacaaagaca acgaagcaga    180
acccgttgta gaaggtaacg ctaccattag cgtagtattg aagaccagca atccgaatcg    240
tgttttcggg gttgcagatg acgaagcaaa agtggctaag ttgaccgtaa tggttttataa    300 tggagaacag caggaagcca tcgaatcagc cgaaaatgcg actaagattg agaatatcaa    360
atgtggtgca ggccaacgta cgctggtcgt aatggccaat acgggtggaa tggaattggc    420
tggcaagact cttgcagagg taaaagcatt gacaactgta ctgactgaag aaaaccaagg    480
ggccacaggt ttgatcatga cagcagagcc aaaagcaatc gttttgaagg caggcaagaa    540
ctatattgga tacgatggag ccggagaggg caaccacatt gagaatgctc tcttgaaat    600 caaacgtgta catgctcgca tggctttcac cgaaattaaa gtacagatga gcgcagccta    660
cgataacatt tacacattta cccctgaaaa gatttatggt ctcattgcaa agaagcaatc    720
taatttgttc ggggcaacac tcgtgaatgc agacgctaat tatctgacag gttctttgac    780
```

```
cacatttaac ggtgcttaca cacctaccaa ctatgccaat gttccttggt tgagccgtga    840
ttacgttgca cctaccgctg gtgctcctca gggcttctac gtattagaaa atgactactc    900
agctaacagt ggaactattc atccgacaat cctgtgtgtt tatggcaaac ttcagaaaaa    960
cggagccgac ctgacgggaa ccgatttagc agcagctcag gccgccaatt gggtggatgc   1020
agaa                                                                1024

<210> SEQ ID NO 98
<211> LENGTH: 733
<212> TYPE: DNA
<213> ORGANISM: Artificial Sequence
<220> FEATURE:
<223> OTHER INFORMATION: Description of Artificial Sequence:P.
      circumdentaria B97 fimA polynucleotide sequence

<400> SEQUENCE: 98
taatggagaa cagcaggaag ccatcgaatc agccgaaaat gcgactaaga ttgagaatat     60
caaatgtggt gcaggccaac gtacgctggt cgtaatggcc aatacgggtg aatggaatt    120 ggctggcaag actcttgcag aggtaaaagc attgacaact gtactgactg aagaaaacca   180
agaggccaca ggtttgatca tgacagcaga gccaaaagca atcgttttga aggcaggcaa   240
gaactatatt ggatacgatg gagccggaga gggcaaccac attgagaatg ctcctcttga   300
aatcaaacgt gtacatgctc gcatggcttt caccgaaatt aaagtacaga tgagcgcagc   360
ctacgataac atttacacat ttaccccctga aaagatttat ggtctcattg caaagaagca   420
atctaatttg ttcggggcaa cactcgtgaa tgcagacgct aattatctga caggttcttt   480
gaccacattt aacggtgctt acacacctac caactatgcc aatgttcctt ggttgagccg   540
tgattacgtt gcacctaccg ctggtgctcc tcagggcttc tacgtattag aaaatgacta   600
ctcagctaac agtggaacta ttcatccgac aatcctgtgt gtttatggca aacttcagaa   660
aaacggagcc gacctgacgg gaaccgattt agcagcagct caggccgcca attgggtgga   720
tgcagaaggc aag                                                      733

<210> SEQ ID NO 99
<211> LENGTH: 1024
<212> TYPE: DNA
<213> ORGANISM: Artificial Sequence
<220> FEATURE:
<223> OTHER INFORMATION: Description of Artificial Sequence:P.
      cangingivalis B98 fimA polynucleotide sequence

<400> SEQUENCE: 99
ggcctcgaga acaaagacaa cgaagcagaa cccgttgtag aaggtaacgc taccattagc     60
gtagtattga agaccagcaa tccgaatcgt gctttcgggg ttgcagatga cgaagcaaaa    120
gtggctaaac tgactgtaat ggtctacaag ggtgagcagc aggaagccat caaatcagcc    180
gaaaatgcaa ttaaggttga aacatcaaa tgtggtgcag gctcacgtac gctggtcgta    240
atggccaata cgggtggaat ggaattggct ggcaagactc ttgcagaggt aaaagcattg    300
acaactgaac taactgcaga aaaccaagag gctacaggtt tgatcatgac agcagagcct   360
gttgacgtaa cacttgtcgc cggcaataac tattatggtt atgatggaac tcagggaggc   420
aatcagattt cgcaaggtac tcctcttgaa atcaaacgtg ttcatgcccg tattgcgttc   480
accaagattg aagtgaagat gagcgagtct tatgtgaaca atacaacctt taccccccgaa   540 aacatctatg cacttgtggc taagaagaag tctaatctat tcggtacttc attggcaaat   600
agtgatgatg cttatttgac cggttctttg acgactttca acggtgctta taccccctgca   660
```

-continued

```
aactatactc atgtcgtctg gttgggaaga ggctacacag cgccttccaa tgatgctcca      720
caaggtttct atgttttgga gagtgcatac gctcagaatg caggtctacg tcctaccatt      780
ctatgtgtaa agggtaagct gacaaagcat gatggtactc ctttgagttc tgaggaaatg      840
acagctgcat tcaatgccgg ctggattgtt gcaaacaatg atcctacgac ctattatcct      900
gtattagtga actttgagag caataattac acctacacag gtgatgctgt tgagaaaggg      960
aaaatcgttc gtaaccacaa gtttgacatc aatctgacga tcaccggtcc tggtacgaat     1020
aatc                                                                  1024
```

<210> SEQ ID NO 100
<211> LENGTH: 783
<212> TYPE: DNA
<213> ORGANISM: Artificial Sequence
<220> FEATURE:
<223> OTHER INFORMATION: Description of Artificial Sequence:P. salivosa
      B104 fimA polynucleotide sequence

<400> SEQUENCE: 100

```
tggctaartt gactgtaatg gtttataatg gagaacagca ggaagccatc raatcagccg       60
aaaatgcgac taagrttgar rayatcaaat gtrgtgcagg ccaacgtacg ctggtcgtaa      120
tggccaatac gggtgsaatg gaaytggytg gcaagactct tgcagaggta aaagcattga      180
caactgwact gactgmagaa accaagagg cyrcaggktt gatcatgaca gcagagccaa       240
aarcaatcgt tttgaaggca ggcaagaact ayattggata crrtggaarcc ggagaggya      300 aycacattga gaatgmtcct cttraratca arcgtgtwca tgctcgcatg gctttcaccg      360
aaattaaagt rcaratgagc gcagcctacg ataacattta cacattyryc cctgaaaaga      420
tttatggtct cattgcaaag aagcaatcta atttgttcgg ggcaacactc gtraatgcag      480
acgctaatta tctgacaggt tcttttgacca catttaacgg tgcttacaca cctrccaact      540
atgccaatgt kccttggytg agccgtratt acgttgcacc trccgcygrt gctcctcagg      600
gyttctacgt attagaaaat gactactcag ctaacrgtgg aactattcat ccgacaatcc      660
tgtgtgttta tggcaaactt cagaaaaacg gagccgacyt grcgggarcc gatttagcar      720
cwgctcaggc cgccaattgg gtggatgcag aaggcaagac ctattaccct gtattrgtra      780
act                                                                   783
```

<210> SEQ ID NO 101
<211> LENGTH: 733
<212> TYPE: DNA
<213> ORGANISM: Artificial Sequence
<220> FEATURE:
<223> OTHER INFORMATION: Description of Artificial Sequence:P.
      denticanis B106 fimA polynucleotide sequence

<400> SEQUENCE: 101

```
taatggagaa cagcaggaag ccatcgaatc agccgaaaat gcgactaaga ttgagaatat       60
caaatgtggt gcaggccaac gtacgctggt cgtaatggcc aatacgggtg aatggaattt      120
ggctggcaag actcttgcag aggtaaaagc attgacaact gtactgactg aagaaaacca      180
agaggccaca ggtttgatca tgacagcaga gccaaaagca atcgttttga aggcaggcaa      240
gaactatatt ggatacgatg gagccggaga gggcaaccac attgagaatg ctcctcttga      300
aatcaaacgt gtacatgctc gcatggcttt caccgaaatt aaagtacaga tgagcgcagc      360
ctacgataac atttacacat ttaccccctga aaagatttat ggtctcattg caaagaagca      420
```

```
atctaatttg ttcggggcaa cactcgtgaa tgcagacgct aattatctga caggttcttt       480
gaccacattt aacggtgctt acacacctac caactatgcc aatgttcctt ggttgagccg       540
tgattacgtt gcacctaccg ctggtgctcc tcagggcttc tacgtattag aaaatgacta       600
ctcagctaac agtggaacta ttcatccgac aatcctgtgt gtttatggca aacttcagaa       660
aaacggagcc gacctgacgg gaaccgattt agcagcagct caggccgcca attgggtgga       720
tgcagaaggc aag                                                         733

<210> SEQ ID NO 102
<211> LENGTH: 742
<212> TYPE: DNA
<213> ORGANISM: Artificial Sequence
<220> FEATURE:
<223> OTHER INFORMATION: Description of Artificial Sequence:P.
      endodontalis B114 fimA polynucleotide sequence

<400> SEQUENCE: 102
caagggtgag cagcaggaag ccatcaaatc agccgaaaat gcaattaagg ttgagaacat        60
caaatgtggt gcaggctcac gtacgctggt cgtaatggcc aatacgggtg gaatggaatt       120
ggctggcaag actcttgcag aggtaaaagc attgacaact gaactaactg cagaaaacca       180
agaggctaca ggtttgatca tgacagcaga gcctgttgac gtaacacttg tcgccggcaa       240
taactattat ggttatgatg gaactcaggg aggcaatcag atttcgcaag gtactcctct       300
tgaaatcaaa cgtgttcatg cccgtattgc gttcaccaag attgaagtga agatgagcga       360
gtcttatgtg aacaaataca actttacccc cgaaaacatc tatgcacttg tggctaagaa       420
gaagtctaat ctattcggta cttcattggc aaatagtgat gatgcttatt tgaccggttc       480
tttgacgact ttcaacggtg cttataccc tgcaaactat actcatgtcg tctggttggg       540
aagaggctac acagcgcctt ccaatgatgc tccacaaggt ttctatgttt tggagagtgc       600
atacgctcag aatgcaggtc tacgtcctac cattctatgt gtaaagggta agctgacaaa       660
gcatgatggt actcctttga gttctgagga aatgacagct gcattcaatg ccggctggat       720
tgttgcaaac aatgatccta cg                                               742

<210> SEQ ID NO 103
<211> LENGTH: 281
<212> TYPE: PRT
<213> ORGANISM: Artificial Sequence
<220> FEATURE:
<223> OTHER INFORMATION: P. gulae B43 FimA polypeptide sequence

<400> SEQUENCE: 103

Met Lys Lys Thr Lys Gly Ala Ala Ala Met Thr Ala Cys Asn Lys Asp
1               5                   10                  15

Asn Ala Val Val Gly Asn Ala Thr Ser Val Val Lys Thr Ser Asn Asn
                20                  25                  30

Arg Ala Gly Val Ala Asp Asp Ala Lys Val Ala Lys Thr Val Met Val
            35                  40                  45

Tyr Lys Gly Ala Lys Ser Ala Asn Ala Lys Val Asn Lys Cys Gly Ala
        50                  55                  60

Gly Ser Arg Thr Val Val Met Ala Asn Thr Gly Met Ala Gly Lys
65                  70                  75                  80

Thr Ala Val Lys Ala Thr Thr Thr Ala Asn Ala Thr Gly Met Thr Ala
                85                  90                  95

Val Asp Val Thr Val Ala Gly Asn Asn Tyr Tyr Gly Tyr Asp Gly Thr
            100                 105                 110
```

Gly Gly Asn Ser Gly Thr Lys Arg Val His Ala Arg Ala Thr Lys Val
            115                 120                 125

Lys Met Ser Ser Tyr Val Asn Lys Tyr Asn Thr Asn Tyr Ala Val Ala
        130                 135                 140

Lys Lys Lys Ser Asn Gly Thr Ser Ala Asn Ser Asp Asp Ala Tyr Thr
145                 150                 155                 160

Gly Ser Thr Thr Asn Gly Ala Tyr Thr Ala Asn Tyr Thr His Val Val
                165                 170                 175

Trp Gly Arg Gly Tyr Thr Ala Ser Asn Asp Ala Gly Tyr Val Ser Ala
            180                 185                 190

Tyr Ala Asn Ala Gly Arg Thr Cys Val Lys Gly Lys Thr Lys His Asp
            195                 200                 205

Gly Thr Ser Ser Met Thr Ala Ala Asn Ala Gly Trp Val Ala Asn Asn
            210                 215                 220

Asp Thr Thr Tyr Tyr Val Val Asn Ser Asn Asn Tyr Thr Tyr Thr Gly
225                 230                 235                 240

Asp Ala Val Lys Gly Lys Val Arg Asn His Lys Asp Asn Thr Thr Gly
            245                 250                 255

Gly Thr Asn Asn Asn Thr Ser Ala Asn Asn Val Asn Cys Val Val Ala
            260                 265                 270

Ala Trp Lys Gly Val Val Asn Val Trp
            275                 280

<210> SEQ ID NO 104
<211> LENGTH: 170
<212> TYPE: PRT
<213> ORGANISM: Artificial Sequence
<220> FEATURE:
<223> OTHER INFORMATION: P. circumdentaria B52 FimA polypeptide sequence

<400> SEQUENCE: 104

Asn Gly Ala Ser Ala Asn Ala Thr Lys Asn Lys Cys Gly Ala Gly Arg
1               5                   10                  15

Thr Val Val Met Ala Asn Thr Gly Gly Met Ala Gly Lys Thr Ala Val
            20                  25                  30

Lys Ala Thr Thr Val Thr Asn Ala Thr Gly Met Thr Ala Lys Ala Val
        35                  40                  45

Lys Ala Gly Lys Asn Tyr Gly Tyr Asp Gly Ala Gly Gly Asn His Asn
    50                  55                  60

Ala Lys Arg Val His Ala Arg Met Ala Thr Lys Val Met Ser Ala Ala
65                  70                  75                  80

Tyr Asp Asn Tyr Thr Thr Lys Tyr Gly Ala Lys Lys Ser Asn Gly Ala
                85                  90                  95

Thr Val Asn Ala Asp Ala Asn Tyr Thr Gly Ser Thr Thr Asn Gly Ala
            100                 105                 110

Tyr Thr Thr Asn Tyr Ala Asn Val Trp Ser Arg Asp Tyr Val Ala Thr
        115                 120                 125

Ala Gly Ala Gly Tyr Val Asn Asp Tyr Ser Ala Asn Ser Gly Thr His
    130                 135                 140

Thr Cys Val Tyr Gly Lys Lys Asn Gly Ala Asp Thr Gly Thr Asp Ala
145                 150                 155                 160

Ala Ala Ala Ala Asn Trp Val Asp Ala Gly
                165                 170

<210> SEQ ID NO 105

<211> LENGTH: 275
<212> TYPE: PRT
<213> ORGANISM: Artificial Sequence
<220> FEATURE:
<223> OTHER INFORMATION: P. gulae B69 FimA AA

<400> SEQUENCE: 105

```
Met Lys Lys Thr Lys Gly Ala Ala Met Thr Ala Cys Asn Lys Asp
1               5                   10                  15

Asn Ala Val Val Gly Asn Ala Thr Ser Val Val Lys Thr Ser Asn Asn
                20                  25                  30

Arg Val Gly Val Ala Asp Asp Ala Lys Val Ala Lys Thr Val Met Val
            35                  40                  45

Tyr Asn Gly Ala Ser Ala Asn Ala Thr Lys Asn Lys Cys Gly Ala Gly
        50                  55                  60

Arg Thr Val Val Met Ala Asn Thr Gly Gly Met Ala Gly Lys Thr Ala
65                  70                  75                  80

Val Lys Ala Thr Thr Val Thr Asn Gly Ala Thr Gly Met Thr Ala Lys
                85                  90                  95

Ala Val Lys Ala Gly Lys Asn Tyr Gly Tyr Asp Gly Ala Gly Gly Asn
            100                 105                 110

His Asn Ala Lys Arg Val His Ala Arg Met Ala Thr Lys Val Met Ser
        115                 120                 125

Ala Ala Tyr Asp Asn Tyr Thr Thr Lys Tyr Gly Ala Lys Lys Ser Asn
    130                 135                 140

Gly Ala Thr Val Asn Ala Asp Ala Asn Tyr Thr Gly Ser Thr Thr Asn
145                 150                 155                 160

Gly Ala Tyr Thr Thr Asn Tyr Ala Asn Val Trp Ser Arg Asp Tyr Val
                165                 170                 175

Ala Thr Ala Gly Ala Gly Tyr Val Asn Asp Tyr Ser Ala Asn Ser Gly
            180                 185                 190

Thr His Thr Cys Val Tyr Gly Lys Lys Asn Gly Ala Asp Thr Gly Thr
        195                 200                 205

Asp Ala Ala Ala Ala Asn Trp Val Asp Ala Gly Lys Thr Tyr Tyr
    210                 215                 220

Val Val Asn Asn Ser Asn Asn Tyr Thr Tyr Asp Asn Gly Tyr Thr Lys
225                 230                 235                 240

Asn Lys Arg Asn His Lys Tyr Asp Lys Thr Thr Gly Gly Thr Asn Asn
                245                 250                 255

Asn Thr Ser Ala His Asn Val Cys Thr Val Ala Trp Val Val Gly Asn
            260                 265                 270

Ala Thr Trp
        275
```

<210> SEQ ID NO 106
<211> LENGTH: 170
<212> TYPE: PRT
<213> ORGANISM: Artificial Sequence
<220> FEATURE:
<223> OTHER INFORMATION: P. circumdentaria B97 FimA polypeptide sequence

<400> SEQUENCE: 106

```
Asn Gly Ala Ser Ala Asn Ala Thr Lys Asn Lys Cys Gly Ala Gly Arg
1               5                   10                  15

Thr Val Val Met Ala Asn Thr Gly Gly Met Ala Gly Lys Thr Ala Val
                20                  25                  30

Lys Ala Thr Thr Val Thr Asn Ala Thr Gly Met Thr Ala Lys Ala Val
```

```
                    35                  40                  45
Lys Ala Gly Lys Asn Tyr Gly Tyr Asp Gly Ala Gly Asn His Asn
             50                  55                  60

Ala Lys Arg Val His Ala Arg Met Ala Thr Lys Val Met Ser Ala Ala
 65                  70                  75                  80

Tyr Asp Asn Tyr Thr Thr Lys Tyr Gly Ala Lys Lys Ser Asn Gly Ala
                 85                  90                  95

Thr Val Asn Ala Asp Ala Asn Tyr Thr Gly Ser Thr Asn Gly Ala
                100                 105                 110

Tyr Thr Thr Asn Tyr Ala Asn Val Trp Ser Arg Asp Tyr Val Ala Thr
                115                 120                 125

Ala Gly Ala Gly Tyr Val Asn Asp Tyr Ser Ala Asn Ser Gly Thr His
            130                 135                 140

Thr Cys Val Tyr Gly Lys Lys Asn Gly Ala Asp Thr Gly Thr Asp Ala
145                 150                 155                 160

Ala Ala Ala Ala Asn Trp Val Asp Ala Gly
                165                 170

<210> SEQ ID NO 107
<211> LENGTH: 257
<212> TYPE: PRT
<213> ORGANISM: Artificial Sequence
<220> FEATURE:
<223> OTHER INFORMATION: P. cangingivalis B98 FimA AA

<400> SEQUENCE: 107

Val Val Gly Asn Ala Thr Ser Val Val Lys Thr Ser Asn Asn Arg Ala
 1               5                  10                  15

Gly Val Ala Asp Asp Ala Lys Val Ala Lys Thr Val Met Val Tyr Lys
                20                  25                  30

Gly Ala Lys Ser Ala Asn Ala Lys Val Asn Lys Cys Gly Ala Gly Ser
             35                  40                  45

Arg Thr Val Val Met Ala Asn Thr Gly Gly Met Ala Gly Lys Thr Ala
 50                  55                  60

Val Lys Ala Thr Thr Thr Ala Asn Ala Thr Gly Met Thr Ala Val Asp
 65                  70                  75                  80

Val Thr Val Ala Gly Asn Asn Tyr Tyr Gly Tyr Asp Gly Thr Gly
                 85                  90                  95

Asn Ser Gly Thr Lys Arg Val His Ala Arg Ala Thr Lys Val Lys Met
                100                 105                 110

Ser Ser Tyr Val Asn Lys Tyr Asn Thr Asn Tyr Ala Val Ala Lys Lys
            115                 120                 125

Lys Ser Asn Gly Thr Ser Ala Asn Ser Asp Asp Ala Tyr Thr Gly Ser
            130                 135                 140

Thr Thr Asn Gly Ala Tyr Thr Ala Asn Tyr Thr His Val Val Trp Gly
145                 150                 155                 160

Arg Gly Tyr Thr Ala Ser Asn Asp Ala Gly Tyr Val Ser Ala Tyr Ala
                165                 170                 175

Asn Ala Gly Arg Thr Cys Val Lys Gly Lys Thr Lys His Asp Gly Thr
            180                 185                 190

Ser Ser Met Thr Ala Ala Asn Ala Gly Trp Val Ala Asn Asn Asp Thr
        195                 200                 205

Thr Tyr Tyr Val Val Asn Ser Asn Asn Tyr Tyr Thr Gly Asp Ala
            210                 215                 220

Val Lys Gly Lys Val Arg Asn His Lys Asp Asn Thr Thr Gly Gly Thr
```

```
                225                 230                 235                 240
Asn Asn Asn Thr Ser Ala Asn Asn Val Asn Cys Val Val Ala Ala Trp
                    245                 250                 255

Lys

<210> SEQ ID NO 108
<211> LENGTH: 161
<212> TYPE: PRT
<213> ORGANISM: Artificial Sequence
<220> FEATURE:
<223> OTHER INFORMATION: P. salivosa B104 FimA polypeptide sequence

<400> SEQUENCE: 108

Ala Thr Val Met Val Tyr Asn Gly Ala Ser Ala Asn Ala Thr Lys Lys
1               5                   10                  15

Cys Ala Gly Arg Thr Val Val Met Ala Asn Thr Gly Met Gly Lys Thr
                20                  25                  30

Ala Val Lys Ala Thr Thr Thr Asn Ala Gly Met Thr Ala Lys Val Lys
            35                  40                  45

Ala Gly Lys Asn Gly Tyr Gly Gly Gly His Asn Arg Val His Ala Arg
        50                  55                  60

Met Ala Thr Lys Val Met Ser Ala Ala Tyr Asp Asn Tyr Thr Lys Tyr
65                  70                  75                  80

Gly Ala Lys Lys Ser Asn Gly Ala Thr Val Asn Ala Asp Ala Asn Tyr
                85                  90                  95

Thr Gly Ser Thr Thr Asn Gly Ala Tyr Thr Asn Tyr Ala Asn Val Trp
            100                 105                 110

Ser Arg Tyr Val Ala Ala Gly Tyr Val Asn Asp Tyr Ser Ala Asn
        115                 120                 125

Gly Thr His Thr Cys Val Tyr Gly Lys Lys Asn Gly Ala Asp Gly Asp
    130                 135                 140

Ala Ala Ala Ala Asn Trp Val Asp Ala Gly Lys Thr Tyr Tyr Val Val
145                 150                 155                 160

Asn

<210> SEQ ID NO 109
<211> LENGTH: 170
<212> TYPE: PRT
<213> ORGANISM: Artificial Sequence
<220> FEATURE:
<223> OTHER INFORMATION: P. denticanis B106 FimA polypeptide sequence

<400> SEQUENCE: 109

Asn Gly Ala Ser Ala Asn Ala Thr Lys Asn Lys Cys Gly Ala Gly Arg
1               5                   10                  15

Thr Val Val Met Ala Asn Thr Gly Gly Met Ala Gly Lys Thr Ala Val
                20                  25                  30

Lys Ala Thr Thr Val Thr Asn Ala Thr Gly Met Thr Ala Lys Ala Val
            35                  40                  45

Lys Ala Gly Lys Asn Tyr Gly Tyr Asp Gly Ala Gly Asn His Asn
        50                  55                  60

Ala Lys Arg Val His Ala Arg Met Ala Thr Lys Val Met Ser Ala Ala
65                  70                  75                  80

Tyr Asp Asn Tyr Thr Thr Lys Tyr Gly Ala Lys Lys Ser Asn Gly Ala
                85                  90                  95

Thr Val Asn Ala Asp Ala Asn Tyr Thr Gly Ser Thr Thr Asn Gly Ala
            100                 105                 110
```

```
Tyr Thr Thr Asn Tyr Ala Asn Val Trp Ser Arg Asp Tyr Val Ala Thr
        115                 120                 125

Ala Gly Ala Gly Tyr Val Asn Asp Tyr Ser Ala Asn Ser Gly Thr His
    130                 135                 140

Thr Cys Val Tyr Gly Lys Lys Asn Gly Ala Asp Thr Gly Thr Asp Ala
145                 150                 155                 160

Ala Ala Ala Ala Asn Trp Val Asp Ala Gly
                165                 170

<210> SEQ ID NO 110
<211> LENGTH: 177
<212> TYPE: PRT
<213> ORGANISM: Artificial Sequence
<220> FEATURE:
<223> OTHER INFORMATION: P. endodontalis B114 FimA polypeptide sequence

<400> SEQUENCE: 110

Lys Gly Ala Lys Ser Ala Asn Ala Lys Val Asn Lys Cys Gly Ala Gly
1               5                   10                  15

Ser Arg Thr Val Val Met Ala Asn Thr Gly Gly Met Ala Gly Lys Thr
            20                  25                  30

Ala Val Lys Ala Thr Thr Thr Ala Asn Ala Thr Gly Met Thr Ala Val
        35                  40                  45

Asp Val Thr Val Ala Gly Asn Asn Tyr Tyr Gly Tyr Asp Gly Thr Gly
    50                  55                  60

Gly Asn Ser Gly Thr Lys Arg Val His Ala Arg Ala Thr Lys Val Lys
65                  70                  75                  80

Met Ser Ser Tyr Val Asn Lys Tyr Asn Thr Asn Tyr Ala Val Ala Lys
                85                  90                  95

Lys Lys Ser Asn Gly Thr Ser Ala Asn Ser Asp Asp Ala Tyr Thr Gly
            100                 105                 110

Ser Thr Thr Asn Gly Ala Tyr Thr Ala Asn Tyr Thr His Val Val Trp
        115                 120                 125

Gly Arg Gly Tyr Thr Ala Ser Asn Asp Ala Gly Tyr Val Ser Ala Tyr
    130                 135                 140

Ala Asn Ala Gly Arg Thr Cys Val Lys Gly Lys Thr Lys His Asp Gly
145                 150                 155                 160

Thr Ser Ser Met Thr Ala Ala Asn Ala Gly Trp Val Ala Asn Asn Asp
                165                 170                 175

Thr

<210> SEQ ID NO 111
<211> LENGTH: 1024
<212> TYPE: DNA
<213> ORGANISM: Artificial Sequence
<220> FEATURE:
<223> OTHER INFORMATION: Description of Artificial Sequence:P. gulae B43
      oprF polynucleotide sequence

<400> SEQUENCE: 111
acattcgttg gagctattgc actgaatgca agtgcacagg aaaatactgt accggcaacg      60
ggtcagttac ccgccaaaaa tgttgctttc gctcgcaaca agcaggcag caattggttc     120 gtaacactgc agggcggtgt tgcagcgcag ttcctcaatg acaacaacaa caaagatttt    180
gtagaccgct gggtgctgc cggctctatt tcagttggaa aatatcacaa tccattcttt    240
gcaacccgtt tgcaaattaa cggagctcag gcacacacgt tccttggaaa aaatgcggaa    300
```

```
caagaaatta agaccaattt tggcgcagct cactttgact tcatgttcga tgtggttaat    360
tactttgcgc catatcgcga aaatcgtttc ttccatttaa ttccatgggt aggtgttggt    420
taccagcata aattcattgg cagcaaatgg agtaaagaca atgtcgagtc tctgactgcc    480
aatctgggtg ttatgatggc tttcagatta ggaaaacgtg tagactttgt gatcgaagca    540
caagcagcac actccaatct caacttaagc cgtgctttca atgccaagcc gactcctatt    600
ttccaggatc aggaaggacg ttattacaat ggattccaag gaatggcgac agcaggtctt    660
aacttccgct tgggtgctgt aggcttcaat gccatcgagc ccatggacta cgcgcttatc    720
aacgatctga atggtcagat taatcgcctg cgcagagaag tcgaagaact ctccaagcgt    780
cctgtatcat gtcccgaatg ccccgacgtt acacccgtta ccaagacaga aaacaagcta    840
accgagaagg ctgtactctt ccgtttcgac agctatgttg tagacaaaga ccagcttatc    900
aatctgtatg acgtagctca gtttgtaaaa gaaaccaacg agccgattac tgttgtaggc    960
tatgctgatc ctacgggtga cactcagtac aacgaaagat tgtctgagcg tcgcgcaaaa    1020
gccg                                                                 1024
```

<210> SEQ ID NO 112
<211> LENGTH: 1024
<212> TYPE: DNA
<213> ORGANISM: Artificial Sequence
<220> FEATURE:
<223> OTHER INFORMATION: Description of Artificial Sequence:P. cansulci
      B46 oprF polynucleotide sequence

<400> SEQUENCE: 112

```
acattggccg gggtttacgc cctttcagcc tctgctcagc aggagaatat gccacgaatg     60
gggcagactc ccgccaagaa taccgcttac gctcgctctg aagccggtga caattggttt    120
gtgactttgc aaggaggtgc tgctatgcag tttgggaaag gtaacgagga tgccgacttc    180
ttcgaccgcc aaactgttgc tcccactttt gccgtaggta atggcacaa tcctttcttc    240 gggaccagat tgcaaatggg cttgggggta tctcacgact ctcgaacaa cgaagcgaaa    300 tccaagttgg agatgaacca cgctcgctat gctaacgcac actttgactt tatgtttgat    360
gtgattaact acttcaagcc ctacagtgag gaccgcgtat tccaccttat tccgtgggta    420
ggtttgggtt acgatcacaa gtttgagaaa acagcaact tcaaggtgga tgctcttaca    480
gccaacgccg gtttgatgtt tgctttccgt gtgatggagc gtatggacat tgtgttggaa    540
agccaggtaa tgtattctga cttcaacctc aacacagctc tgcccgagcc tcgctacaca    600
gcttgctccg gcatgctcac tgccggtttg aacttccgta taggaaatat cggatggagc    660
gagatcctac caatggattg gggcttggta aatgacctga acggacaaat caacgccatg    720
cgtgctaaga acgcagagtt gagcaagcgt cccgtttctt gccccgaatg cccggaagtt    780
gagcctcgtg tagagcgtat caatatgctt tcggacaagt ctgttctttt ccgtgccggc    840
aagacaactg tagacagcga tcaaatggta acgatcttcg acgtagctca gtttgcaaag    900
aagaatggca cacagatcac cgttacaggc tatgcagaca agaagggcaa agaaagcgat    960
cgcacctctg aacttcgtgc aaaagccgta gccaagattc tcaccgacaa gtacggtgta    1020
cctt                                                                1024
```

<210> SEQ ID NO 113
<211> LENGTH: 1024
<212> TYPE: DNA
<213> ORGANISM: Artificial Sequence
<220> FEATURE:

<223> OTHER INFORMATION: Description of Artificial Sequence:P.
circumdentaria B52 oprF polynucleotide sequence

<400> SEQUENCE: 113

```
tctataatgg gagctacagc actctccgcg agtgctcaac aatctacgac acctgagact      60
caaactttgc cagctcgcaa gacggctttt gaccgttccg cgggtcactg gttcttgact     120
ctacagggtg gtgtaaatgc acagttttg gaagaaaacg agtctcaaga catcgtaaat      180
cgtctccgtg tgatgccaac tctttcttta ggaaagtggc acaatcccta ttttgcaacc     240
cgtttgcaag tttttggggg gccaacccct acttactaca aggaggtttc tggggaggtt     300
aagaccctaa ataccgccat ggctggagct cactttgatt ttatgtttga tgtagtaaac     360
ttctatgcaa agtataatcc taaacgagta ttccatttga ttccttggtt cggtgtggga    420
tatggtttca aatactataa cgattttgct gatttagctg atatgattca gtttaatgaa    480
cccttccgtc actcagcaac tgcgaatgct ggttttgatga tgagttttcg cttggcaaaa    540
cgtttggatt tggttctgga agggcaggct atatattcta acttgaatat tgtaaagcaa    600
gagatagatt ataaagcccc cattatgccc tattcaaata tctacaacgg attgacaggt    660
gtcgttactg caggtctcaa ctttaatctc ggtcgtgttg cttgggagtc cgtaactcct    720
atggatatgg atcttattaa tgacctaaac ggacaaatta accgtttgcg ttctgagaat    780
acagagttga gaaaacgtcc agtttcttgc ccagaatgtc ctgaagttac tgcagagacg    840
gaagtagtta ctgaaaacgt tttaggtgat aaggcgattg ttttcaagtt taatagcgca    900
actattgaca aagatcaaca cattgttttg caggatatcg ctgactttgt taaagatggc    960
aacaaagcta ttgttgtaat aggcttcgca gatacaacag gtgatattaa ttacaatatg   1020
catt                                                                1024
```

<210> SEQ ID NO 114
<211> LENGTH: 1024
<212> TYPE: DNA
<213> ORGANISM: Artificial Sequence
<220> FEATURE:
<223> OTHER INFORMATION: Description of Artificial Sequence:P. gulae B69
oprF polynucleotide sequence

<400> SEQUENCE: 114

```
acattcgttg gagctattgc actgaatgca agtgcacagg aaaatactgt accggcaacg      60
ggtcagttac cgccaaaaaa tgttgctttt gcccgcaata aagcaggcgg caattggttt    120
gtaacactgc aaggtggtgt tgcagcacag ttccttaatg acaacaacaa caaagatcta    180
gtagaccgct taggagctac cggatctatc tccgttggaa aatatcacaa tccattcttt    240
gcgactcgtt tgcaaattaa cggaggtcaa gcacacacgt tccttgggaa gaatgcggaa    300
caagaaatta acaccaattt tggagcagct cactttgact tcatgttcga tgtggttaac    360
tactttgcgc catatcgcga aaaccgtttc ttccatttaa ttccatgggt aggtgttggt    420
taccaacaca aattcatcgg tagcgaatgg agtaaagaca acgtcgagtc gctgaccgca    480
aacatgggtg ttatgatggc tttcagatta gggaagcgcg tggactttgt gatcgaagca    540
caagctgctc actccaatct taatttaagt cgcgcattca atgccaagaa aactcctatt    600
ttccacgatc aagaaggtcg ctattacaat ggattccaag gaatggctac agcgggtctt    660
aacttccgct taggtgctgt tggcttcaat gccatcgagc caatggacta cgcgcttatc    720
aacgatctga atggtcagat taaccgtttg cgcagagaag ttgaagagct ctctaagcgt    780
cctgtatcat gccccgaatg tcccgatgta acacccgtta ctaagacaga aaacaagcta    840
```

| | |
|---|---:|
| accgagaagg ctgtactctt ccgcttcgac agctatgttg tagacaaaga ccagctgatc | 900 |
| aatctgtatg acgttgctca gttcgtaaaa gaaactaacg aaccgattac cgttgtaggt | 960 |
| tatgccgatc ctacgggcag cactcagtac aacgaaagat tgtctgagcg tcgcgcaaaa | 1020 |
| gccg | 1024 |

<210> SEQ ID NO 115
<211> LENGTH: 1024
<212> TYPE: DNA
<213> ORGANISM: Artificial Sequence
<220> FEATURE:
<223> OTHER INFORMATION: Description of Artificial Sequence:P.
circumdentaria B97 oprF polynucleotide sequence

<400> SEQUENCE: 115

| | |
|---|---:|
| tctgttatgg gagctacagc actcacagtt agtgctcagc aacctactac acctgagact | 60 |
| cagacattgc ctgctcataa gacggctttt gaccgttctg caggacattg gttcttgact | 120 |
| ctccaaggtg gagttagtgc tcaattttta gaagaaaatg aaagtcaaga aatcttgaat | 180 |
| cgtcttcatg ttatgcctac aatctcttta ggcaagtggc acaatcctta ttttgcaact | 240 |
| cgtttgcaag tgttcggagg tcctactcct acttttttata agaatgctgc tggtaaggtg | 300 |
| atgaaggaaa atgcggctat ggctggggct cactttgact ttatgtttga tgttgtgaac | 360 |
| tactttggta agtataatcc aaagagagtc tttcatcttg tgccttggtt cggtgttgga | 420 |
| tatggcttta ataccataa tgatttcgcc gaaatgagtg atatcattaa gtttaatgag | 480 |
| ccttatcgcc attcagcaac agcgaatgca gggttgatga tgagtttccg cttagcaaaa | 540 |
| cgtcttgatt tagtgcttga aggacaggct atatattcta atttgaatat tgttaagcaa | 600 |
| gaaattgatt ataaagctcc ttctactcct tattctccaa attataatgg cttttggga | 660 |
| gttgttacag caggtcttaa cttaatctt ggtcgtgttg cttgggagac tgttactccc | 720 |
| atggatatgg atttgattaa tgatcttaat ggtcaaatca atcgtttgcg ttctgagaat | 780 |
| actgagttga gaaaacgtcc tgtttcttgt cctgaatgcc cagaagtttc taaagaaaca | 840 |
| actgtagtta cagaaaatgt attgggagac aaagctattg ttttcaaatt taatagtgca | 900 |
| actatcagca agatcaaca tattgttttg caagacattg cggactttgt taagaatgga | 960 |
| aataaggggg ttgccgtgat aggtttcgca gatgtaacag gagatgccaa ttacaatatg | 1020 |
| caac | 1024 |

<210> SEQ ID NO 116
<211> LENGTH: 948
<212> TYPE: DNA
<213> ORGANISM: Artificial Sequence
<220> FEATURE:
<223> OTHER INFORMATION: Description of Artificial Sequence:P.
cangingivalis B98 oprF polynucleotide sequence

<400> SEQUENCE: 116

| | |
|---|---:|
| ggtggagtta gtgctcaatt tttagaagaa aatgaaagtc aagaaatctt gaatcgtctt | 60 |
| catgttatgc ctacaatctc tttaggcaag tggcacaatc cttatttgc aactcgtttg | 120 |
| caagtgttcg gaggtcctac tcctactttt tataagaatg ctgctggtaa ggtgatgaag | 180 |
| gaaaatgcgg ctatggctgg ggctcacttt gactttatgt ttgatgttgt gaactacttt | 240 |
| ggtaagtata atccaaagag agtctttcat cttgtgcctt ggttcggtgt tggatatggc | 300 |
| tttaaatacc ataatgattt cgccgaaatg agtgatatca ttaagtttaa tgagccttat | 360 |

```
cgccattcag caacagcgaa tgcagggttg atgatgagtt tccgcttagc aaaacgtctt    420
gatttagtgc ttgaaggaca ggctatatat tctaatttga atattgttaa gcaagaaatt    480
gattataaag ctccttctac tccttattct ccaaattata atgggctttt gggagttgtt    540
acagcaggtc ttaactttaa tcttggtcgt gttgcttggg agactgttac tcccatggat    600
atggatttga ttaatgatct taatggtcaa atcaatcgtt tgcgttctga aatactgag     660 ttgagaaaac gtcctgtttc ttgtcctgaa tgcccagaag tttctaaaga aacaactgta    720
gttacagaaa atgtattggg agacaaagct attgttttca aatttaatag tgcaactatc    780
agcaaagatc aacatattgt tttgcaagac attgcggact tgttaagaa tggaaataag     840 ggggttgccg tgataggttt cgcagatgta acaggagatg ccaattacaa tatgcaactt    900
tctgaacgtc gtgctaaggc tgttgcggaa gctcttgtga atcaattc                 948
```

```
<210> SEQ ID NO 117
<211> LENGTH: 969
<212> TYPE: DNA
<213> ORGANISM: Artificial Sequence
<220> FEATURE:
<223> OTHER INFORMATION: Description of Artificial Sequence:P. salivosa
      B104 oprF polynucleotide sequence

<400> SEQUENCE: 117
cattggttct tgactctcca aggtggagtt agtgctcaat ttttagaaga aaatgaaagt     60
caagaaatct tgaatcgtct tcatgttatg cctacaatct ctttaggcaa gtggcacaat    120
ccttattttg caactcgttt gcaagtgttc ggaggtccta ctcctacttt ttataagaat    180
gctgctggta aggtgatgaa ggaaaatgcg gctatggctg ggctcactt tgactttatg     240 tttgatgttg tgaactactt tggtaagtat aatccaaaga gagtctttca tcttgtgcct    300
tggttcggtg ttggatatgg ctttaaatac cataatgatt tcgccgaaat gagtgatatc    360
attaagttta tgagcccta tcgccattca gcaacagcga atgcagggtt gatgatgagt    420
ttccgcttag caaaacgtct tgatttagtg cttgaaggac aggctatata ttctaatttg    480
aatattgtta agcaagaaat tgattataaa gctccttcta ctccttattc tccaaattat    540
aatgggcttt tgggagttgt tacagcaggt cttaactta atcttggtcg tgttgcctgg    600
gagactatta ctcccatgga tatggatttg attaatgatc ttaatggtca aatcaatcgt    660
ttgcgttctg agaatactga gttgagaaaa cgtcctgttt cttgtcctga atgcccagaa    720
gtttctaaag aaacaactgt agttacagaa atgtattgg agacaaagc tattgttttc     780 aaatttaata gtgcaactat cagcaaagat caacatattg ttttgcaaga cattgcggac    840
tttgttaaga atgaaataa ggggttgcc gtgataggtt tcgcagatgt aacaggagat     900
gccaattaca atatgcaact ttctgaacgt cgtgctaagg ctgttgcgga agctcttgtg    960
aatcaattc                                                             969
```

```
<210> SEQ ID NO 118
<211> LENGTH: 1024
<212> TYPE: DNA
<213> ORGANISM: Artificial Sequence
<220> FEATURE:
<223> OTHER INFORMATION: Description of Artificial Sequence:P.
      denticanis B106 oprF polynucleotide sequence

<400> SEQUENCE: 118
gctcataaga cggcttttga ccgttctgca ggacattggt tcttgactct ccaaggtgga     60
gttagtgctc aatttttaga agaaaatgaa agtcaagaaa tcttgaatcg tcttcatgtt    120
```

```
atgcctacaa tctctttagg caagtggcac aatccttatt ttgcaactcg tttgcaagtg    180
ttcggaggtc ctactcctac tttttataag aatgctgctg gtaaggtgat gaaggaaaat    240
gcggctatgg ctgggctca cttttgacttt atgtttgatg ttgtgaacta ctttggtaag    300
tataatccaa agagagtctt tcatcttgtg ccttggttcg gtgttggata tggctttaaa    360
taccataatg atttcgccga aatgagtgat atcattaagt ttaatgagcc ttatcgccat    420
tcagcaacag cgaatgcagg gttgatgatg agtttccgct agcaaaacg tcttgattta    480 gtgcttgaag gacaggctat atattctaat ttgaatattg ttaagcaaga aattgattat    540
aaagctcctt ctactcctta ttctccaaat tataatgggc ttttgggagt tgttacagca    600
ggtcttaact ttaatcttgg tcgtgttgct tgggagactg ttactcccat ggatatggat    660
ttgattaatg atcttaatgg tcaaatcaat cgtttgcgtt ctgagaatac tgagttgaga    720
aaacgtcctg tttcttgtcc tgaatgccca gaagtttcta agaaacaac tgtagttaca    780 gaaaatgtat tgggagacaa agctattgtt ttcaaattta atagtgcaac tatcagcaaa    840
gatcaacata ttgttttgca agacattgcg gactttgtta agaatggaaa taaggggtt    900 gccgtgatag gtttcgcaga tgtaacagga gatgccaatt acaatatgca actttctgaa    960
cgtcgtgcta aggctgttgc ggaagctctt gtgaatcaat tcggagttcc ttctgatatg   1020
attt                                                                1024

<210> SEQ ID NO 119
<211> LENGTH: 1024
<212> TYPE: DNA
<213> ORGANISM: Artificial Sequence
<220> FEATURE:
<223> OTHER INFORMATION: Description of Artificial Sequence:P.
      endodontalis B114 oprF polynucleotide sequence

<400> SEQUENCE: 119
tcagcactgg gggctttggc acttacagct agtgctcaac aaaactacgaa accagcgaat    60 agtatgcccg cattcaagac tgcatttgaa cgcagcggcg gtcattggtt tctgacaatt    120
cagggtggcc tgagtgctca acttttgggt gaaaatgaaa agatggactt tggcaagcgt    180 ctgctcacatg ctgccaaggc cagtgacaac acccaaacag aggctagcta cctacgcatc    240
atgcccacgc tctctgtagg taaatggcat aatccctact ttgctactcg tgtacagctc    300
ttcggtggtc tcactcctct ctacaatact gagggtggcg ttaatgtaca cacctacaac    360
actgccacga tcggtgccca ctatgatttc atgtttgatg tagtaaacta tttcgccaag    420
tacaacccca aacgtttctt ccacgtaatt ccttgggtgg gtcttggtta caacttcaag    480
tatcatgatg tatttggatt caaggagccc tatcgtcact ctgtcacagg taacgcaggc    540
atggagtttg ctttccgcct cggtaagcgt gtagaccttg tactcgaagc tcaggtagtg    600
tacaacaacc tgaacctgat caagcaggaa gtcgactacg atgtagtcac tactccctat    660
gtacctgctg atacatacgc tggtcttatg accatgttta ctgctggtct taacttcaat    720
ctgggcaagg ttgagtggga aactgttgag ccgatggact accagctcat aaacgacttg    780
aactctcaga tcagccgtct acgtagcgaa aacgcagagc tttccaagcg tcctgctttc    840
tgccccgagt gtcccgaagt agaggaagta gaagatgttg ttgttgacca gtatgtcctc    900
accgacaagg ctatcctctt cgactttgac aagagcaaca tccgcaagga ccaacaagct    960
cagcttggta tgattgctga attcgtgaag aagtacaata cgcctatcgt ggtagtaggc   1020
tatg                                                               1024
```

<210> SEQ ID NO 120
<211> LENGTH: 375
<212> TYPE: PRT
<213> ORGANISM: Artificial Sequence
<220> FEATURE:
<223> OTHER INFORMATION: Description of Artificial Sequence:P. gulae B43 OprF polypeptide sequence

<400> SEQUENCE: 120

```
Thr Phe Val Gly Ala Ile Ala Leu Asn Ala Ser Ala Gln Glu Asn Thr
 1               5                  10                  15

Val Pro Ala Thr Gly Gln Leu Pro Ala Lys Asn Val Ala Phe Ala Arg
                20                  25                  30

Asn Lys Ala Gly Ser Asn Trp Phe Val Thr Leu Gln Gly Gly Val Ala
            35                  40                  45

Ala Gln Phe Leu Asn Asp Asn Asn Lys Asp Phe Val Asp Arg Leu
        50                  55                  60

Gly Ala Ala Gly Ser Ile Ser Val Gly Lys Tyr His Asn Pro Phe Phe
 65                 70                  75                  80

Ala Thr Arg Leu Gln Ile Asn Gly Ala Gln Ala His Thr Phe Leu Gly
                85                  90                  95

Lys Asn Ala Glu Gln Glu Ile Lys Thr Asn Phe Gly Ala Ala His Phe
           100                 105                 110

Asp Phe Met Phe Asp Val Val Asn Tyr Phe Ala Pro Tyr Arg Glu Asn
       115                 120                 125

Arg Phe Phe His Leu Ile Pro Trp Val Gly Val Gly Tyr Gln His Lys
   130                 135                 140

Phe Ile Gly Ser Lys Trp Ser Lys Asp Asn Val Glu Ser Leu Thr Ala
145                 150                 155                 160

Asn Leu Gly Val Met Met Ala Phe Arg Leu Gly Lys Arg Val Asp Phe
                165                 170                 175

Val Ile Glu Ala Gln Ala Ala His Ser Asn Leu Asn Leu Ser Arg Ala
            180                 185                 190

Phe Asn Ala Lys Pro Thr Pro Ile Phe Gln Asp Gln Glu Gly Arg Tyr
        195                 200                 205

Tyr Asn Gly Phe Gln Gly Met Ala Thr Ala Gly Leu Asn Phe Arg Leu
    210                 215                 220

Gly Ala Val Gly Phe Asn Ala Ile Glu Pro Met Asp Tyr Ala Leu Ile
225                 230                 235                 240

Asn Asp Leu Asn Gly Gln Ile Asn Arg Leu Arg Arg Glu Val Glu Glu
                245                 250                 255

Leu Ser Lys Arg Pro Val Ser Cys Pro Glu Cys Pro Asp Val Thr Pro
            260                 265                 270

Val Thr Lys Thr Glu Asn Lys Leu Thr Glu Lys Ala Val Leu Phe Arg
        275                 280                 285

Phe Asp Ser Tyr Val Val Asp Lys Asp Gln Leu Ile Asn Leu Tyr Asp
    290                 295                 300

Val Ala Gln Phe Val Lys Glu Thr Asn Glu Pro Ile Thr Val Val Gly
305                 310                 315                 320

Tyr Ala Asp Pro Thr Gly Asp Thr Gln Tyr Asn Glu Arg Leu Ser Glu
                325                 330                 335

Arg Arg Ala Lys Ala Val Val Asp Val Leu Thr Gly Lys Tyr Gly Val
            340                 345                 350

Pro Ser Glu Leu Ile Ser Val Glu Trp Lys Gly Asp Thr Thr Gln Pro
```

```
            355                 360                 365
Phe Asn Lys Lys Ala Trp Asn
    370                 375

<210> SEQ ID NO 121
<211> LENGTH: 366
<212> TYPE: PRT
<213> ORGANISM: Artificial Sequence
<220> FEATURE:
<223> OTHER INFORMATION: Description of Artificial Sequence:P. cansulci
      B46 OprF polypeptide sequence

<400> SEQUENCE: 121

Thr Leu Ala Gly Val Tyr Ala Leu Ser Ala Ser Ala Gln Gln Glu Asn
  1               5                  10                  15

Met Pro Arg Met Gly Gln Thr Pro Ala Lys Asn Thr Ala Tyr Ala Arg
                 20                  25                  30

Ser Glu Ala Gly Asp Asn Trp Phe Val Thr Leu Gln Gly Gly Ala Ala
             35                  40                  45

Met Gln Phe Gly Lys Gly Asn Glu Asp Ala Asp Phe Phe Asp Arg Gln
 50                  55                  60

Thr Val Ala Pro Thr Phe Ala Val Gly Lys Trp His Asn Pro Phe Phe
 65                  70                  75                  80

Gly Thr Arg Leu Gln Met Gly Leu Gly Val Ser His Asp Phe Ser Asn
                 85                  90                  95

Asn Glu Ala Lys Ser Lys Leu Glu Met Asn His Ala Arg Tyr Ala Asn
            100                 105                 110

Ala His Phe Asp Phe Met Phe Asp Val Ile Asn Tyr Phe Lys Pro Tyr
        115                 120                 125

Ser Glu Asp Arg Val Phe His Leu Ile Pro Trp Val Gly Leu Gly Tyr
    130                 135                 140

Asp His Lys Phe Glu Lys Asn Ser Asn Phe Lys Val Asp Ala Leu Thr
145                 150                 155                 160

Ala Asn Ala Gly Leu Met Phe Ala Phe Arg Val Met Glu Arg Met Asp
                165                 170                 175

Ile Val Leu Glu Ser Gln Val Met Tyr Ser Asp Phe Asn Leu Asn Thr
            180                 185                 190

Ala Leu Pro Glu Pro Arg Tyr Thr Ala Cys Ser Gly Met Leu Thr Ala
        195                 200                 205

Gly Leu Asn Phe Arg Ile Gly Asn Ile Gly Trp Ser Glu Ile Leu Pro
    210                 215                 220

Met Asp Trp Gly Leu Val Asn Asp Leu Asn Gly Gln Ile Asn Ala Met
225                 230                 235                 240

Arg Ala Lys Asn Ala Glu Leu Ser Lys Arg Pro Val Ser Cys Pro Glu
                245                 250                 255

Cys Pro Glu Val Glu Pro Arg Val Glu Arg Ile Asn Met Leu Ser Asp
            260                 265                 270

Lys Ser Val Leu Phe Arg Ala Gly Lys Thr Thr Val Asp Ser Asp Gln
        275                 280                 285

Met Val Thr Ile Phe Asp Val Ala Gln Phe Ala Lys Lys Asn Gly Thr
    290                 295                 300

Gln Ile Thr Val Thr Gly Tyr Ala Asp Lys Lys Gly Lys Glu Ser Asp
305                 310                 315                 320

Arg Thr Ser Glu Leu Arg Ala Lys Ala Val Ala Lys Ile Leu Thr Asp
                325                 330                 335
```

```
Lys Tyr Gly Val Pro Ser Asp Arg Ile Ser Ile Glu Trp Lys Gly Val
            340                 345                 350

Ser Glu Gln Val Tyr Asp Asn Arg Asp Trp Asn Arg Val Val
        355                 360                 365

<210> SEQ ID NO 122
<211> LENGTH: 382
<212> TYPE: PRT
<213> ORGANISM: Artificial Sequence
<220> FEATURE:
<223> OTHER INFORMATION: Description of Artificial Sequence:P.
      circumdentaria B52 OprF polypeptide sequence

<400> SEQUENCE: 122

Ser Ile Met Gly Ala Thr Ala Leu Ser Ala Ser Ala Gln Gln Ser Thr
  1               5                  10                  15

Thr Pro Glu Thr Gln Thr Leu Pro Ala Arg Lys Thr Ala Phe Asp Arg
             20                  25                  30

Ser Ala Gly His Trp Phe Leu Thr Leu Gln Gly Gly Val Asn Ala Gln
         35                  40                  45

Phe Leu Glu Glu Asn Glu Ser Gln Asp Ile Val Asn Arg Leu Arg Val
 50                  55                  60

Met Pro Thr Leu Ser Leu Gly Lys Trp His Asn Pro Tyr Phe Ala Thr
 65                  70                  75                  80

Arg Leu Gln Val Phe Gly Pro Thr Pro Thr Tyr Tyr Lys Glu Val
                 85                  90                  95

Ser Gly Glu Val Lys Thr Leu Asn Thr Ala Met Ala Gly Ala His Phe
                100                 105                 110

Asp Phe Met Phe Asp Val Val Asn Phe Tyr Ala Lys Tyr Asn Pro Lys
            115                 120                 125

Arg Val Phe His Leu Ile Pro Trp Phe Gly Val Gly Tyr Gly Phe Lys
        130                 135                 140

Tyr Tyr Asn Asp Phe Ala Asp Leu Ala Asp Met Ile Gln Phe Asn Glu
145                 150                 155                 160

Pro Phe Arg His Ser Ala Thr Ala Asn Ala Gly Leu Met Met Ser Phe
                165                 170                 175

Arg Leu Ala Lys Arg Leu Asp Leu Val Leu Glu Gly Gln Ala Ile Tyr
            180                 185                 190

Ser Asn Leu Asn Ile Val Lys Gln Glu Ile Asp Tyr Lys Ala Pro Ile
        195                 200                 205

Met Pro Tyr Ser Asn Ile Tyr Asn Gly Leu Thr Gly Val Val Thr Ala
210                 215                 220

Gly Leu Asn Phe Asn Leu Gly Arg Val Ala Trp Glu Ser Val Thr Pro
225                 230                 235                 240

Met Asp Met Asp Leu Ile Asn Asp Leu Asn Gly Gln Ile Asn Arg Leu
                245                 250                 255

Arg Ser Glu Asn Thr Glu Leu Arg Lys Arg Pro Val Ser Cys Pro Glu
            260                 265                 270

Cys Pro Glu Val Thr Ala Glu Thr Glu Val Val Thr Glu Asn Val Leu
        275                 280                 285

Gly Asp Lys Ala Ile Val Phe Lys Phe Asn Ser Ala Thr Ile Asp Lys
    290                 295                 300

Asp Gln His Ile Val Leu Gln Asp Ile Ala Asp Phe Val Lys Asp Gly
305                 310                 315                 320

Asn Lys Ala Ile Val Val Ile Gly Phe Ala Asp Thr Thr Gly Asp Ile
                325                 330                 335
```

-continued

```
Asn Tyr Asn Met His Leu Ser Glu Arg Arg Ala Lys Ala Val Ala Glu
            340                 345                 350

Ala Leu Val Asn Lys Phe Gly Val Ser Ser Asp Met Ile Ser Val Glu
        355                 360                 365

Trp Gln Gly Glu Thr Glu Gln Phe Asn Pro Arg Ala Trp Asn
    370                 375                 380

<210> SEQ ID NO 123
<211> LENGTH: 375
<212> TYPE: PRT
<213> ORGANISM: Artificial Sequence
<220> FEATURE:
<223> OTHER INFORMATION: Description of Artificial Sequence:P. gulae B69
      OprF polypeptide sequence

<400> SEQUENCE: 123

Thr Phe Val Gly Ala Ile Ala Leu Asn Ala Ser Ala Gln Glu Asn Thr
  1               5                  10                  15

Val Pro Ala Thr Gly Gln Leu Pro Ala Lys Asn Val Ala Phe Ala Arg
             20                  25                  30

Asn Lys Ala Gly Gly Asn Trp Phe Val Thr Leu Gln Gly Gly Val Ala
         35                  40                  45

Ala Gln Phe Leu Asn Asp Asn Asn Lys Asp Leu Val Asp Arg Leu
     50                  55                  60

Gly Ala Thr Gly Ser Ile Ser Val Gly Lys Tyr His Asn Pro Phe Phe
 65                  70                  75                  80

Ala Thr Arg Leu Gln Ile Asn Gly Gly Gln Ala His Thr Phe Leu Gly
             85                  90                  95

Lys Asn Ala Glu Gln Glu Ile Asn Thr Asn Phe Gly Ala Ala His Phe
            100                 105                 110

Asp Phe Met Phe Asp Val Val Asn Tyr Phe Ala Pro Tyr Arg Glu Asn
        115                 120                 125

Arg Phe Phe His Leu Ile Pro Trp Val Gly Val Gly Tyr Gln His Lys
    130                 135                 140

Phe Ile Gly Ser Glu Trp Ser Lys Asp Asn Val Glu Ser Leu Thr Ala
145                 150                 155                 160

Asn Met Gly Val Met Met Ala Phe Arg Leu Gly Lys Arg Val Asp Phe
                165                 170                 175

Val Ile Glu Ala Gln Ala Ala His Ser Asn Leu Asn Leu Ser Arg Ala
            180                 185                 190

Phe Asn Ala Lys Lys Thr Pro Ile Phe His Asp Gln Glu Gly Arg Tyr
        195                 200                 205

Tyr Asn Gly Phe Gln Gly Met Ala Thr Ala Gly Leu Asn Phe Arg Leu
    210                 215                 220

Gly Ala Val Gly Phe Asn Ala Ile Glu Pro Met Asp Tyr Ala Leu Ile
225                 230                 235                 240

Asn Asp Leu Asn Gly Gln Ile Asn Arg Leu Arg Arg Glu Val Glu Glu
                245                 250                 255

Leu Ser Lys Arg Pro Val Ser Cys Pro Glu Cys Pro Asp Val Thr Pro
            260                 265                 270

Val Thr Lys Thr Glu Asn Lys Leu Thr Glu Lys Ala Val Leu Phe Arg
        275                 280                 285

Phe Asp Ser Tyr Val Val Asp Lys Asp Gln Leu Ile Asn Leu Tyr Asp
    290                 295                 300

Val Ala Gln Phe Val Lys Glu Thr Asn Glu Pro Ile Thr Val Val Gly
```

```
                305                 310                 315                 320
Tyr Ala Asp Pro Thr Gly Ser Thr Gln Tyr Asn Glu Arg Leu Ser Glu
                    325                 330                 335

Arg Arg Ala Lys Ala Val Val Asp Val Leu Thr Gly Lys Tyr Gly Val
                340                 345                 350

Pro Ser Glu Leu Ile Ser Val Glu Trp Lys Gly Asp Ser Thr Gln Pro
            355                 360                 365

Phe Asn Lys Lys Ala Trp Asn
        370                 375

<210> SEQ ID NO 124
<211> LENGTH: 382
<212> TYPE: PRT
<213> ORGANISM: Artificial Sequence
<220> FEATURE:
<223> OTHER INFORMATION: Description of Artificial Sequence:P.
      circumdentaria B97 OprF polypeptide sequence

<400> SEQUENCE: 124

Ser Val Met Gly Ala Thr Ala Leu Thr Val Ser Ala Gln Gln Pro Thr
  1               5                  10                  15

Thr Pro Glu Thr Gln Thr Leu Pro Ala His Lys Thr Ala Phe Asp Arg
                20                  25                  30

Ser Ala Gly His Trp Phe Leu Thr Leu Gln Gly Gly Val Ser Ala Gln
            35                  40                  45

Phe Leu Glu Glu Asn Glu Ser Gln Glu Ile Leu Asn Arg Leu His Val
        50                  55                  60

Met Pro Thr Ile Ser Leu Gly Lys Trp His Asn Pro Tyr Phe Ala Thr
 65                  70                  75                  80

Arg Leu Gln Val Phe Gly Gly Pro Thr Pro Thr Phe Tyr Lys Asn Ala
                85                  90                  95

Ala Gly Lys Val Met Lys Glu Asn Ala Ala Met Ala Gly Ala His Phe
            100                 105                 110

Asp Phe Met Phe Asp Val Val Asn Tyr Phe Gly Lys Tyr Asn Pro Lys
        115                 120                 125

Arg Val Phe His Leu Val Pro Trp Phe Gly Val Gly Tyr Gly Phe Lys
    130                 135                 140

Tyr His Asn Asp Phe Ala Glu Met Ser Asp Ile Ile Lys Phe Asn Glu
145                 150                 155                 160

Pro Tyr Arg His Ser Ala Thr Ala Asn Ala Gly Leu Met Met Ser Phe
                165                 170                 175

Arg Leu Ala Lys Arg Leu Asp Leu Val Leu Glu Gly Gln Ala Ile Tyr
            180                 185                 190

Ser Asn Leu Asn Ile Val Lys Gln Glu Ile Asp Tyr Lys Ala Pro Ser
        195                 200                 205

Thr Pro Tyr Ser Pro Asn Tyr Asn Gly Leu Leu Gly Val Val Thr Ala
    210                 215                 220

Gly Leu Asn Phe Asn Leu Gly Arg Val Ala Trp Glu Thr Val Thr Pro
225                 230                 235                 240

Met Asp Met Asp Leu Ile Asn Asp Leu Asn Gly Gln Ile Asn Arg Leu
                245                 250                 255

Arg Ser Glu Asn Thr Glu Leu Arg Lys Arg Pro Val Ser Cys Pro Glu
            260                 265                 270

Cys Pro Glu Val Ser Lys Glu Thr Thr Val Val Thr Glu Asn Val Leu
        275                 280                 285
```

```
Gly Asp Lys Ala Ile Val Phe Lys Phe Asn Ser Ala Thr Ile Ser Lys
290                 295                 300

Asp Gln His Ile Val Leu Gln Asp Ile Ala Asp Phe Val Lys Asn Gly
305                 310                 315                 320

Asn Lys Gly Val Ala Val Ile Gly Phe Ala Asp Val Thr Gly Asp Ala
                325                 330                 335

Asn Tyr Asn Met Gln Leu Ser Glu Arg Arg Ala Lys Ala Val Ala Glu
                340                 345                 350

Ala Leu Val Asn Gln Phe Gly Val Pro Ser Asp Met Ile Ser Val Glu
            355                 360                 365

Trp Gln Gly Glu Thr Glu Leu Phe Glu Ala Arg Ala Trp Asn
370                 375                 380
```

```
<210> SEQ ID NO 125
<211> LENGTH: 316
<212> TYPE: PRT
<213> ORGANISM: Artificial Sequence
<220> FEATURE:
<223> OTHER INFORMATION: Description of Artificial Sequence:P.
      cangingivalis B98 OprF polypeptide sequence

<400> SEQUENCE: 125

Gly Gly Val Ser Ala Gln Phe Leu Glu Glu Asn Glu Ser Gln Glu Ile
1               5                   10                  15

Leu Asn Arg Leu His Val Met Pro Thr Ile Ser Leu Gly Lys Trp His
                20                  25                  30

Asn Pro Tyr Phe Ala Thr Arg Leu Gln Val Phe Gly Gly Pro Thr Pro
            35                  40                  45

Thr Phe Tyr Lys Asn Ala Ala Gly Lys Val Met Lys Glu Asn Ala Ala
50                  55                  60

Met Ala Gly Ala His Phe Asp Phe Met Phe Asp Val Val Asn Tyr Phe
65                  70                  75                  80

Gly Lys Tyr Asn Pro Lys Arg Val Phe His Leu Val Pro Trp Phe Gly
                85                  90                  95

Val Gly Tyr Gly Phe Lys Tyr His Asn Asp Phe Ala Glu Met Ser Asp
            100                 105                 110

Ile Ile Lys Phe Asn Glu Pro Tyr Arg His Ser Ala Thr Ala Asn Ala
        115                 120                 125

Gly Leu Met Met Ser Phe Arg Leu Ala Lys Arg Leu Asp Leu Val Leu
130                 135                 140

Glu Gly Gln Ala Ile Tyr Ser Asn Leu Asn Ile Val Lys Gln Glu Ile
145                 150                 155                 160

Asp Tyr Lys Ala Pro Ser Thr Pro Tyr Ser Pro Asn Tyr Asn Gly Leu
                165                 170                 175

Leu Gly Val Val Thr Ala Gly Leu Asn Phe Asn Leu Gly Arg Val Ala
            180                 185                 190

Trp Glu Thr Val Thr Pro Met Asp Met Asp Leu Ile Asn Asp Leu Asn
        195                 200                 205

Gly Gln Ile Asn Arg Leu Arg Ser Glu Asn Thr Glu Leu Arg Lys Arg
210                 215                 220

Pro Val Ser Cys Pro Glu Cys Pro Glu Val Ser Lys Glu Thr Thr Val
225                 230                 235                 240

Val Thr Glu Asn Val Leu Gly Asp Lys Ala Ile Val Phe Lys Phe Asn
                245                 250                 255

Ser Ala Thr Ile Ser Lys Asp Gln His Ile Val Leu Gln Asp Ile Ala
            260                 265                 270
```

```
Asp Phe Val Lys Asn Gly Asn Lys Gly Val Ala Val Ile Gly Phe Ala
        275                 280                 285

Asp Val Thr Gly Asp Ala Asn Tyr Asn Met Gln Leu Ser Glu Arg Arg
    290                 295                 300

Ala Lys Ala Val Ala Glu Ala Leu Val Asn Gln Phe
305                 310                 315

<210> SEQ ID NO 126
<211> LENGTH: 323
<212> TYPE: PRT
<213> ORGANISM: Artificial Sequence
<220> FEATURE:
<223> OTHER INFORMATION: Description of Artificial Sequence:P. salivosa
      B104 OprF polypeptide sequence

<400> SEQUENCE: 126

His Trp Phe Leu Thr Leu Gln Gly Gly Val Ser Ala Gln Phe Leu Glu
  1               5                  10                  15

Glu Asn Glu Ser Gln Glu Ile Leu Asn Arg Leu His Val Met Pro Thr
             20                  25                  30

Ile Ser Leu Gly Lys Trp His Asn Pro Tyr Phe Ala Thr Arg Leu Gln
         35                  40                  45

Val Phe Gly Gly Pro Thr Pro Thr Phe Tyr Lys Asn Ala Ala Gly Lys
     50                  55                  60

Val Met Lys Glu Asn Ala Ala Met Ala Gly Ala His Phe Asp Phe Met
 65                  70                  75                  80

Phe Asp Val Val Asn Tyr Phe Gly Lys Tyr Asn Pro Lys Arg Val Phe
                 85                  90                  95

His Leu Val Pro Trp Phe Gly Val Gly Tyr Gly Phe Lys Tyr His Asn
            100                 105                 110

Asp Phe Ala Glu Met Ser Asp Ile Ile Lys Phe Asn Glu Pro Tyr Arg
        115                 120                 125

His Ser Ala Thr Ala Asn Ala Gly Leu Met Met Ser Phe Arg Leu Ala
    130                 135                 140

Lys Arg Leu Asp Leu Val Leu Glu Gly Gln Ala Ile Tyr Ser Asn Leu
145                 150                 155                 160

Asn Ile Val Lys Gln Glu Ile Asp Tyr Lys Ala Pro Ser Thr Pro Tyr
                165                 170                 175

Ser Pro Asn Tyr Asn Gly Leu Leu Gly Val Val Thr Ala Gly Leu Asn
            180                 185                 190

Phe Asn Leu Gly Arg Val Ala Trp Glu Thr Ile Thr Pro Met Asp Met
        195                 200                 205

Asp Leu Ile Asn Asp Leu Asn Gly Gln Ile Asn Arg Leu Arg Ser Glu
    210                 215                 220

Asn Thr Glu Leu Arg Lys Arg Pro Val Ser Cys Pro Glu Cys Pro Glu
225                 230                 235                 240

Val Ser Lys Glu Thr Thr Val Val Thr Glu Asn Val Leu Gly Asp Lys
                245                 250                 255

Ala Ile Val Phe Lys Phe Asn Ser Ala Thr Ile Ser Lys Asp Gln His
            260                 265                 270

Ile Val Leu Gln Asp Ile Ala Asp Phe Val Lys Asn Gly Asn Lys Gly
        275                 280                 285

Val Ala Val Ile Gly Phe Ala Asp Val Thr Gly Asp Ala Asn Tyr Asn
    290                 295                 300

Met Gln Leu Ser Glu Arg Arg Ala Lys Ala Val Ala Glu Ala Leu Val
```

305              310             315              320

Asn Gln Phe

<210> SEQ ID NO 127
<211> LENGTH: 349
<212> TYPE: PRT
<213> ORGANISM: Artificial Sequence
<220> FEATURE:
<223> OTHER INFORMATION: Description of Artificial Sequence:P.
      denticanis B106 OprF polypeptide sequence

<400> SEQUENCE: 127

Ala His Lys Thr Ala Phe Asp Arg Ser Ala Gly His Trp Phe Leu Thr
 1               5                  10                  15

Leu Gln Gly Gly Val Ser Ala Gln Phe Leu Glu Glu Asn Glu Ser Gln
            20                  25                  30

Glu Ile Leu Asn Arg Leu His Val Met Pro Thr Ile Ser Leu Gly Lys
        35                  40                  45

Trp His Asn Pro Tyr Phe Ala Thr Arg Leu Gln Val Phe Gly Gly Pro
    50                  55                  60

Thr Pro Thr Phe Tyr Lys Asn Ala Ala Gly Lys Val Met Lys Glu Asn
65                  70                  75                  80

Ala Ala Met Ala Gly Ala His Phe Asp Phe Met Phe Asp Val Val Asn
                85                  90                  95

Tyr Phe Gly Lys Tyr Asn Pro Lys Arg Val Phe His Leu Val Pro Trp
            100                 105                 110

Phe Gly Val Gly Tyr Gly Phe Lys Tyr His Asn Asp Phe Ala Glu Met
        115                 120                 125

Ser Asp Ile Ile Lys Phe Asn Glu Pro Tyr Arg His Ser Ala Thr Ala
    130                 135                 140

Asn Ala Gly Leu Met Met Ser Phe Arg Leu Ala Lys Arg Leu Asp Leu
145                 150                 155                 160

Val Leu Glu Gly Gln Ala Ile Tyr Ser Asn Leu Asn Ile Val Lys Gln
                165                 170                 175

Glu Ile Asp Tyr Lys Ala Pro Ser Thr Pro Tyr Ser Pro Asn Tyr Asn
            180                 185                 190

Gly Leu Leu Gly Val Val Thr Ala Gly Leu Asn Phe Asn Leu Gly Arg
        195                 200                 205

Val Ala Trp Glu Thr Val Thr Pro Met Asp Met Asp Leu Ile Asn Asp
    210                 215                 220

Leu Asn Gly Gln Ile Asn Arg Leu Arg Ser Glu Asn Thr Glu Leu Arg
225                 230                 235                 240

Lys Arg Pro Val Ser Cys Pro Glu Cys Pro Glu Val Ser Lys Glu Thr
                245                 250                 255

Thr Val Val Thr Glu Asn Val Leu Gly Asp Lys Ala Ile Val Phe Lys
            260                 265                 270

Phe Asn Ser Ala Thr Ile Ser Lys Asp Gln His Ile Val Leu Gln Asp
        275                 280                 285

Ile Ala Asp Phe Val Lys Asn Gly Asn Lys Gly Val Ala Val Ile Gly
    290                 295                 300

Phe Ala Asp Val Thr Gly Asp Ala Asn Tyr Asn Met Gln Leu Ser Glu
305                 310                 315                 320

Arg Arg Ala Lys Ala Val Ala Glu Ala Leu Val Asn Gln Phe Gly Val
                325                 330                 335

Pro Ser Asp Met Ile Ser Val Glu Trp Gln Gly Glu Thr

```
                340             345

<210> SEQ ID NO 128
<211> LENGTH: 395
<212> TYPE: PRT
<213> ORGANISM: Artificial Sequence
<220> FEATURE:
<223> OTHER INFORMATION: Description of Artificial Sequence:P.
      endodontalis B114 OprF polypeptide sequence

<400> SEQUENCE: 128

Ser Ala Leu Gly Ala Leu Ala Leu Thr Ala Ser Ala Gln Gln Thr Thr
 1               5                  10                  15

Lys Pro Ala Asn Ser Met Pro Ala Phe Lys Thr Ala Phe Glu Arg Ser
             20                  25                  30

Gly Gly His Trp Phe Leu Thr Ile Gln Gly Gly Leu Ser Ala Gln Leu
         35                  40                  45

Leu Gly Glu Asn Glu Lys Met Asp Phe Gly Lys Arg Leu Leu His Ala
     50                  55                  60

Ala Lys Ala Ser Asp Asn Thr Gln Thr Glu Ala Ser Tyr Leu Arg Ile
 65                  70                  75                  80

Met Pro Thr Leu Ser Val Gly Lys Trp His Asn Pro Tyr Phe Ala Thr
                 85                  90                  95

Arg Val Gln Leu Phe Gly Gly Leu Thr Pro Leu Tyr Asn Thr Glu Gly
            100                 105                 110

Gly Val Asn Val His Thr Tyr Asn Thr Ala Thr Ile Gly Ala His Tyr
        115                 120                 125

Asp Phe Met Phe Asp Val Val Asn Tyr Phe Ala Lys Tyr Asn Pro Lys
    130                 135                 140

Arg Phe Phe His Val Ile Pro Trp Val Gly Leu Gly Tyr Asn Phe Lys
145                 150                 155                 160

Tyr His Asp Val Phe Gly Phe Lys Glu Pro Tyr Arg His Ser Val Thr
                165                 170                 175

Gly Asn Ala Gly Met Glu Phe Ala Phe Arg Leu Gly Lys Arg Val Asp
            180                 185                 190

Leu Val Leu Glu Ala Gln Val Val Tyr Asn Asn Leu Asn Leu Ile Lys
        195                 200                 205

Gln Glu Val Asp Tyr Asp Val Val Thr Thr Pro Tyr Val Pro Ala Asp
    210                 215                 220

Thr Tyr Ala Gly Leu Met Thr Met Phe Thr Ala Gly Leu Asn Phe Asn
225                 230                 235                 240

Leu Gly Lys Val Glu Trp Glu Thr Val Glu Pro Met Asp Tyr Gln Leu
                245                 250                 255

Ile Asn Asp Leu Asn Ser Gln Ile Ser Arg Leu Arg Ser Glu Asn Ala
            260                 265                 270

Glu Leu Ser Lys Arg Pro Ala Phe Cys Pro Glu Cys Pro Glu Val Glu
        275                 280                 285

Glu Val Glu Asp Val Val Asp Gln Tyr Val Leu Thr Asp Lys Ala
    290                 295                 300

Ile Leu Phe Asp Phe Asp Lys Ser Asn Ile Arg Lys Asp Gln Gln Ala
305                 310                 315                 320

Gln Leu Gly Met Ile Ala Glu Phe Val Lys Lys Tyr Asn Thr Pro Ile
                325                 330                 335

Val Val Val Gly Tyr Ala Asp Pro Thr Gly Lys Ser Lys Tyr Asn Met
            340                 345                 350
```

Glu Leu Ser Lys Arg Arg Ala Gln Ala Val Val Asn Glu Leu Thr Asn
        355                 360                 365

Arg His Gly Val Pro Ala Asp Leu Ile Thr Met Glu Trp Glu Gly Ala
    370                 375                 380

Thr Asn Lys Phe Thr Pro Pro Thr Ala Trp Asn
385                 390                 395

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence:P. gulae B43
      FimA polypeptide fragment sequence #1

<400> SEQUENCE: 129

Ala Cys Asn Lys Asp Asn Glu Ala Glu Pro Val Val
 1               5                  10

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence:P. gulae B43
      FimA polypeptide fragment sequence #2

<400> SEQUENCE: 130

Tyr Pro Val Leu Val Asn Phe Glu Ser Asn Asn Tyr Thr Tyr Thr Gly
 1               5                  10                  15

Asp Ala Val Glu Lys
            20

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence:P. gulae B43
      FimA polypeptide fragment sequence #3

<400> SEQUENCE: 131

Thr Gly Pro Gly Thr Asn Asn Pro Glu Asn Pro Ile Thr Glu Ser Ala
 1               5                  10                  15

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence:P. gulae B43
      OprF polypeptide fragment sequence #1

<400> SEQUENCE: 132

Asn Asp Asn Asn Asn Lys Asp Phe Val Asp Arg Leu Gly Ala
 1               5                  10

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence:P. gulae B43
      OprF polypeptide fragment sequence #2

```
<400> SEQUENCE: 133

Asp Leu Asn Gly Gln Ile Asn Arg Leu Arg Arg Glu Val Glu Glu Leu
 1               5                  10                  15

Ser Lys Arg Pro Val Ser Cys Pro Glu Cys Pro Asp Val
            20                  25

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence:P. gulae B43
      OprF polypeptide fragment sequence #3

<400> SEQUENCE: 134

Ala Asp Pro Thr Gly Asp Thr Gln Tyr Asn Glu Arg Leu Ser Glu Arg
 1               5                  10                  15

Arg Ala Lys Ala Val
            20

<210> SEQ ID NO 135
<211> LENGTH: 47
<212> TYPE: PRT
<213> ORGANISM: Artificial Sequence
<220> FEATURE:
<223> OTHER INFORMATION: Description of Artificial Sequence:pBAD-HisA
      Amino-terminal polypeptide sequence

<400> SEQUENCE: 135

Met Gly Gly Ser His His His His His His Gly Met Ala Ser Met Thr
 1               5                  10                  15

Gly Gly Gln Met Gly Arg Asp Leu Tyr Asp Asp Asp Asp Lys Asp Arg
            20                  25                  30

Trp Gly Ser Glu Leu Glu Ile Cys Ser Gln Tyr His Met Gly Ile
        35                  40                  45

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence:pBAD-TOPO
      Amino-terminal polypeptide sequence

<400> SEQUENCE: 136

Met Gly Ser Gly Ser Gly Asp Asp Asp Asp Lys Leu Ala Leu Met
 1               5                  10                  15

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence:l vector
      Amino-terminal polypeptide sequence

<400> SEQUENCE: 137

Met Gly Thr Thr Thr Thr Thr Thr Ser Leu His Met
 1               5                  10
```